US006869960B2

(12) United States Patent
Ito et al.

(10) Patent No.: US 6,869,960 B2
(45) Date of Patent: Mar. 22, 2005

(54) N-SUBSTITUTED SPIROPIPERIDINE COMPOUNDS AS LIGANDS FOR ORL-1 RECEPTOR

(75) Inventors: Fumitaka Ito, Aichi-ken (JP); Hiroki Koike, Aichi-ken (JP); Asato Morita, Aichi-ken (JP)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/349,760

(22) Filed: Jan. 23, 2003

(65) Prior Publication Data

US 2003/0158219 A1 Aug. 21, 2003

Related U.S. Application Data

(60) Provisional application No. 60/352,437, filed on Jan. 28, 2002.

(51) Int. Cl.$^7$ ............... A61K 31/4709; C07D 47/10
(52) U.S. Cl. ........................... 514/278; 546/17
(58) Field of Search ............... 546/17; 514/278

(56) References Cited

FOREIGN PATENT DOCUMENTS

| WO | 9965494 | 12/1999 |
| WO | 0006545 | 2/2000 |
| WO | WO 2002085354 | * 10/2002 |
| WO | WO 03 000677 | 1/2003 |

OTHER PUBLICATIONS

Meunier et al., "Isolation and structure of the endogenous agonist of opioid receptor–like ORL, receptor", *Nature*, vol. 377, 1995, pp. 532–535.
Reinscheid et al., "Orphanin FQ: A Neuropeptide That Activates an Opioidlike G Protein–Coupled Receptor", *Science*, vol. 270, 1995, pp. 792–794.
S. Rover, et al., "Orl 1 Receptor Ligands Structure–Activity Relationships of 8–Cycloalkyl–1–phenyl–1,3,8–triaza–spiro [4.5]decan–4–ones", Bioogan & Med Chem Ltrs, vol. 10, pp 831–834 (2000).

D. Barlocco, et al., "The opioid receptor like 1 (ORL 1) as a potential target for new analgesics", Eur J of Med Chem, vol. 35, pp 275–282 (2000).

N. Zaveri, et al., "Characterization of opiates, neuroleptics, and synthetic analogs at ORL 1 and opioid receptors", Eur J of Pharma, vol. 428, pp 29–36 (2001).

S. Ronzoni, et al., "Lead generation and lead optimisation approaches in the discovery of selective, non–peptide ORL 1 receptor agonists and antagonists", Expert Opinion on Therap Patents, vol. 525, pp 525–546 (2001).

* cited by examiner

*Primary Examiner*—Rita Desai
(74) *Attorney, Agent, or Firm*—Suzanne M. Harvey; David R. Kurlandsky; Charles A. Ashbrook

(57) ABSTRACT

A compound of the formula:

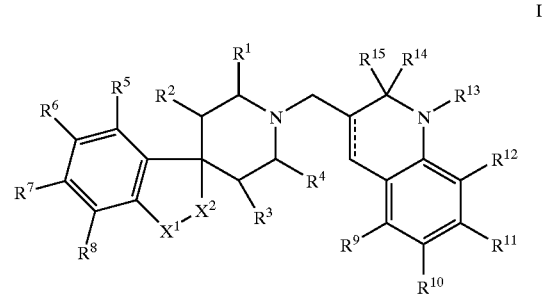

or a pharmaceutically acceptable salt, ester or ether thereof, wherein $R^1$ through $R^{12}$ are independently hydrogen or the like; $X^1$ and $X^2$ are independently $CH_2$ or the like; $R^{13}$ is hydrogen or the like; or $R^{12}$ and $R^{13}$ taken together with three ring atoms of the quinoline ring separating said substituents form a heterocyclic ring; $R^{14}$ and $R^{15}$ are hydrogen or the like or these groups taken together form oxo; and the dotted line represents a single or double bond. These compounds are ligands for ORL-1 receptor and especially are antagonists for said receptor.

11 Claims, No Drawings

N-SUBSTITUTED SPIROPIPERIDINE COMPOUNDS AS LIGANDS FOR ORL-1 RECEPTOR

This application claims benefit of U.S. Provisional Application No. 60/352,437, filed Jan. 28, 2002.

TECHNICAL FIELD

This invention relates to substituted spiropiperidine compounds and their salts, prodrugs and solvates, and a medical use thereof. Also, this invention relates to a pharmaceutical composition comprising said compound, or its salt, prodrug or solvate. The compounds of this invention have binding affinity for ORL-1 receptor. In particular, compounds of this invention have selective antagonist activity for said receptor. The compounds of this invention are useful in treating or preventing disorders or medical conditions selected from pain, a CNS disorder and the like, which is mediated by said receptor and its endogeneous ligand.

BACKGROUND ART

Three types of opioid receptors, $\mu$ (mu), $\delta$ (delta) and $\kappa$ (kappa) have been identified. These receptors may be indicated with combinations of OP (abbreviation for Opioid Peptides) and numeric subscripts as suggested by the International Union of Pharmacology (IUPHAR). Namely, $OP_1$, $OP_2$ and $OP_3$ respectively correspond to $\delta$-, $\kappa$- and $\mu$-receptors. It has been found out that they belong to G-protein-coupled receptors and distribute in the central nervous system (CNS), peripheries and organs in a mammal. As ligands for the receptors, endogeneous and synthetic opioids are known. It is believed that an endogeneous opioid peptide produces their effects through an interaction with the major classes of opioid receptors. For example, endorphins have been purified as endogeneous opioid peptides and bind to both $\delta$- and $\mu$-receptors. Morphine is a well-known non-peptide opioid analgesic and has binding affinity mainly for $\mu$-receptor. Opiates have been widely used as pharmacological agents, but drugs such as morphine and heroin induce some side effects such as drug addiction and euphoria.

Meunier et al. reported isolation of a seventeen-amino-acid-long peptide from rat brain as an endogeneous ligand for an orphan opioid receptor (Nature, Vol. 337, pp. 532–535, Oct. 12, 1995), and said receptor is now known as "opioid receptor-like 1 (abbreviated as ORL1-receptor)". In the same report, the endogeneous opioid ligand has been introduced as agonist for ORL-1 receptor and named as "nociceptine (abbreviated as NC)". Also, the same ligand was named as "orphanin FQ (abbreviated as OFQ or oFQ)" by Reinscheid et al. (Science, Vol. 270, pp. 792–794, 1995). This receptor may be indicated as $OP_4$ in line with a recommendation by IUPHAR in 1998 (British Journal of Pharmacology, Vol. 129, pp. 1261–1283, 2000).

Opioids and their affinity for these receptors have been researched in-vitro and in-vivo. It is possible to date to test whether an opioid has agonist or antagonist properties or a combination of both on the receptors.

Schering's WO 00/06545 discloses piperidine compounds as ligands for ORL1-receptor specifically as agonists for the receptor. The publication generally discloses the compounds of formula I wherein $X^1$ and $X^2$ taken together form a spiro ring; Q is —$CH_2$—; m is 1 and $Z^1$ is $R^{10}$—$(C_3$–$C_7)$ heteocycloalkyl, but the heterocycloalkyl is not fused with benzene ring.

Merck's WO 99/65494 generally discloses spiropiperidine compounds as inhibitors of prenyl-protein transferase and the working example compounds are spiropiperidine compounds substituted with imidazolylmethyl at the nitrogen atom.

BRIEF DISCLOSURE OF THE INVENSION

The present invention provides a compound of the following formula:

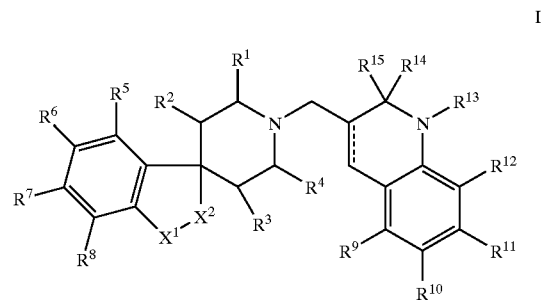

I or a pharmaceutically acceptable salt or solvate thereof, wherein $R^1$ through $R^{12}$ are independently selected from the group consisting of hydrogen; halo; hydroxy; cyano; $(C_1$–$C_6)$ alkyl; $(C_1$–$C_6)$alkyl substituted with one to five halo which may be same or different; $(C_1$–$C_6)$alkyl substituted with one to five substituents independently selected from the group consisting of hydroxy, amino, $[(C_1$–$C_6)$alkyl]NH—, $[(C_1$–$C_6)$alkyl]$_2$N—, $H_2$NC(=O)—, $[(C_1$–$C_6)$alkyl]NHC(=O)—, $[(C_1$–$C_6)$alkyl]$_2$NC(=O)—, $(C_1$–$C_6)$alkoxy and a fully saturated five to six membered heterocyclyl containing one to two hetero atoms independently selected from nitrogen and oxygen; $(C_1$–$C_6)$alkoxy; $(C_1$–$C_6)$alkoxy substituted with one to five halo which may be same or different; $(C_1$–$C_6)$alkoxy substituted with one to five substituents independently selected from the group consisting of hydroxy, amino, $[(C_1$–$C_6)$alkyl]NH—, $[(C_1$–$C_6)$alkyl]$_2$N—, $H_2$NC(=O)—, $[(C_1$–$C_6)$alkyl] NHC(=O)— and $[(C_1$–$C_6)$alkyl]$_2$NC(=O)—; amino; $[(C_1$–$C_6)$alkyl]NH—; $[(C_1$–$C_6)$alkyl]$_2$N—; carboxy; $[(C_1$–$C_6)$alkoxy]C(=O)—; $H_2$NC(=O)—; $[(C_1$–$C_6)$ alkyl]NHC(=O)—; $[(C_1$–$C_6)$alkyl]NHC(=O)— wherein said $(C_1$–$C_6)$alkyl is substituted with one hydroxy; $[(C_1$–$C_6)$alkyl]$_2$NC(=O)—; $[(C_1$–$C_6)$alkyl]$_2$ NC(=O)— wherein either or both of $(C_1$–$C_6)$alkyl is substituted with one hydroxy; aryl selected from phenyl and naphthyl; and four- to eight-membered heterocyclyl containing one to four hetero atoms in the ring independently selected from nitrogen, oxygen and sulfur; or two of $R^1$, $R^2$, $R^3$ and $R^4$ groups taken together form —$CH_2$— or —$(CH_2)_2$— and the remaining two groups are defined as above;

$X^1$ and $X^2$ are independently selected from $CH_2$; CH-hydroxy; O; NH; S; C(=O); $SO_2$; and $[(C_1$–$C_6)$ alkyl]N; or $X^1$ and $X_2$ taken together form CH=CH;

$R^{13}$ is selected from the group consisting of hydrogen; hydroxy; $(C_1$–$C_6)$alkyl; $(C_1$–$C_6)$alkyl substituted with one to five halo which may be same or different; and $(C_1$–$C_6)$alkyl substituted with one to five substituents independently selected from the group consisting of hydroxy, amino, $[(C_1$–$C_6)$alkyl]NH—, $[(C_1$–$C_6)$alkyl]$_2$ N—, $H_2$NC(=O)—, $[(C_1$–$C_6)$alkyl]NHC(=O)—, $[(C_1$–$C_6)$alkyl]$_2$NC(=O)—, $(C_1$–$C_6)$alkoxy and a fully saturated five to six membered heterocyclyl containing one to two hetero atoms independently selected from nitrogen and oxygen; or $R^{12}$ and $R^{13}$ taken together with the three ring atoms of the dihydro- or tetrahydro-quinoline ring separating said substituents form a five to seven membered ring which is partially or fully unsaturated, wherein the ring atom not shared with the dihydro- or tetrahydroquinoline ring and adjacent to the nitrogen atom in the dihydro- or tetrahydroquinoline ring is a carbon atom; the remaining one to three ring atoms not shared with the dihydro- or tetrahydroquinoline ring are carbon atoms, one of said carbon atoms being optionally replaced with a nitrogen, oxygen or sulfur atom; and one or two of the carbon and nitrogen atoms not shared with the dihydro- or tetrahydro-quinoline ring are optionally substituted with substituents independently selected from oxo; hydroxy; $(C_1-C_6)$alkyl; $(C_1-C_6)$alkyl substituted with one to five halo which may be same or different; $(C_1-C_6)$alkyl substituted with one to five substituents independently selected from the group consisting of hydroxy, amino, $[(C_1-C_6)$alkyl]NH—, $[(C_1-C_6)$alkyl]$_2$N—, $H_2$NC(=O)—, $[(C_1-C_6)$alkyl]NHC(=O)—, $[(C_1-C_6)$alkyl]$_2$NC(=O)—, $(C_1-C_6)$alkoxy and a fully saturated five to six membered heterocyclyl containing one to two hetero atoms independently selected from nitrogen and oxygen; $(C_1-C_6)$alkoxy; $(C_1-C_6)$alkoxy substituted with one to five halo which may be same or different; $(C_1-C_6)$alkoxy substituted with one to five substituents independently selected from the group consisting of hydroxy, amino, $[(C_1-C_6)$alkyl]NH—, $[(C_1-C_6)$alkyl]$_2$N—, $H_2$NC(=O)—, $[(C_1-C_6)$alkyl]NHC(=O)— and $[(C_1-C_6)$alkyl]$_2$NC(=O)—; amino; $[(C_1-C_6)$alkyl]NH—; and $[(C_1-C_6)$alkyl]$_2$N—;

both $R^{14}$ and $R^{15}$ are hydrogen or taken together form oxo; and the dotted line represents a single or double bond.

The compounds of the present invention have binding affinity for opioid receptor-like 1 (hereinafter referred to as "ORL-1 receptor").

It is therefore an object of the present invention to provide a compound of formula I which is useful as a lignad for ORL-1 receptor.

It is another object of the present invention to provide a compound of formula I which is a modulator of ORL-1 receptor.

It is another object of the present invention to provide a compound of formula I having selective affinity for ORL-1 receptor. Preferably, these compounds have selective affinity for ORL-1 receptor than $\mu$-receptor.

It is another object of the present invention to provide a compound of formula I having antagonist activity for ORL-1 receptor.

It is another object of the present invention to provide a compound of formula I having selectivity for ORL-1 receptor and antagonist effect for said receptor.

The present invention relates to use of a compound of formula I as a ligand or a modulator for ORL-1 receptor, preferably as a selective ligand for said receptor, more preferably as an antagonist for said receptor, and most preferably as a selective antagonist for said receptor.

DETAILED DESCRIPTION OF THE INVENTION

The term "pain" as used herein includes acute and chronic pain; neuropathic or inflammatory pain such as post herpetic neuralgia, neuralgia, diabetic neuropathy or post operative pain; osteoarthritis or back pain; pain in pregnancy labor and pains known to those skilled in the art (e.g., the pains described in Advances in Pain Research and Therapy, edited by C. R. Chapman et al., and published by Ravan Press (1989)).

The term "alkyl", as used herein, means a straight or branched saturated monovalent hydrocarbon radical including, but not limited to, methyl, ethyl, propyl, isopropyl, n-butyl, sec-butyl, tert-butyl and the like.

The term "cycloalkyl", as used herein, means a saturated carbocyclic radical including, but not limited to, cyclopropyl, cyclobutyl, cyclopentyl, cyclohexyl, cycloheptyl, cyclooctyl, cyclononyl, cyclodecyl and the like.

The term "alkoxy", as used herein, means an O-alkyl group wherein "alkyl" is defined above.

The term "halo", as used herein, refers to F, Cl, Br or I, preferably F or Cl.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

Examples of "a fully saturated five to six membered heterocyclyl containing one to two hetero atoms independently selected from nitrogen and oxygen" include pyrrolidinyl, piperidyl, piperazinyl, morpholinyl, tetrahydrofuranyll, tetrahydropyranyl and the like.

In this specification, the term "quinoline ring" may also mean "dihydro- or tetrahydro-quinoline ring".

A preferred group of compounds of formula (I) of this invention is that wherein both $R^{14}$ and $R^{15}$ are hydrogen.

A preferred group of compounds of formula (I) of this invention is that wherein $R^{14}$ and $R^{15}$ taken together form oxo.

A preferred group of compounds of formula (I) of this invention is that wherein $X^1$ and $X^2$ are independently selected from the group consisting of $CH_2$, O, NH and $[(C_1-C_6)$alkyl]N or taken together form CH=CH.

A preferred group of compounds of formula (I) of this invention is that wherein $R^1$, $R^2$, $R^3$ and $R^4$ are all hydrogen.

A preferred group of compounds of formula (I) of this invention is that wherein $R^5$, $R^6$, $R^7$ and $R^8$ are all hydrogen.

A more preferred group of compounds of formula I of this invention is that wherein $R^9$, $R^{10}$ and $R^{11}$ are independently selected from the group consisting of hydrogen; halo; hydroxy; cyano; $(C_1-C_6)$alkyl; $(C_1-C_6)$alkyl substituted with one to five halo which may be same or different; $(C_1-C_6)$alkyl substituted with one to five substituents independently selected from the group consisting of hydroxy, amino, $[(C_1-C_6)$alkyl]NH—, $[(C_1-C_6)$alkyl]$_2$N—, $H_2$NC(=O)—, $[(C_1-C_6)$alkyl]NHC(=O)—, $[(C_1-C_6)$alkyl]$_2$NC(=O)—, $(C_1-C_6)$alkoxy and a fully saturated five to six membered heterocyclyl containing one to two hetero atoms independently selected from nitrogen and oxygen; $H_2$NC(=O)—; $[(C_1-C_6)$alkyl]NHC(=O)— and $[(C_1-C_6)$alkyl]$_2$NC(=O)—.

A more preferred group of compounds of formula I of this invention is that wherein $R^{12}$ is selected from the group consisting of hydrogen; halo; hydroxy; cyano; $(C_1-C_6)$alkyl; $(C_1-C_6)$alkyl substituted with one to five halo which may be same or different; $(C_1-C_6)$alkyl substituted with one to five substituents independently selected from the group consisting of hydroxy, amino, $[(C_1-C_6)$alkyl]NH—, $[(C_1-C_6)$alkyl]$_2$N—, $H_2$NC(=O)—, $[(C_1-C_6)$alkyl]NHC(=O)—, $[(C_1-C_6)$alkyl]$_2$NC(=O)—, $(C_1-C_6)$alkoxy and a fully saturated five to six membered heterocyclyl containing one to two hetero atoms independently selected from nitrogen and oxygen; $H_2NC(=O)—$; $[(C_1-C_6)alkyl]NHC(=O)—$ and $[(C_1-C_6)alkyl]_2NC(=O)—$.

A more preferred group of compounds of formula I of this invention is that wherein $R^{13}$ is selected from a group consisting of hydrogen; hydroxy; $(C_1-C_6)alkyl$; $(C_1-C_6)$ alkyl substituted with one to five halo which may be same or different; and $(C_1-C_6)alkyl$ substituted with one to five substituents independently selected from the group consisting of hydroxy, amino, $[(C_1-C_6)alkyl]NH—$, $[(C_1-C_6)alkyl]_2N—$, $H_2NC(=O)—$, $[(C_1-C_6)alkyl]NHC(=O)—$, $[(C_1-C_6)alkyl]_2NC(=O)—$, $(C_1-C_6)alkoxy$ and a fully saturated five to six membered heterocyclyl containing one to two hetero atoms independently selected from nitrogen and oxygen.

A preferred individual compounds of formula I of this invention is selected from 2,3-dihydro-1'-[(2-oxo-1,2,3,4-tetrahydro-3-quinolinyl)methyl]spiro[1H-indene-1,4'-piperidine]; 3-(2,3-dihydro-1'H-spiro[indene-1,4'piperidin]-1'-ylmethyl)-8-methoxy-3,4-dihydroquinolin-2(1H)-one; 8-hydroxy-3-[(1-methyl-1,2-dihydro-1'H-spiro[indole-3,4'-piperidin]-1'-yl)methyl]-3,4-dihydroquinolin-2(1H)-one; 8-hydroxy-3-(1'H,3H-spiro[2-benzofuran-1,4'-piperidin]-1'-ylmethyl)-3,4-dihydroquinolin-2(1H)-one; 3-(2,3-dihydro-1'H-spiro[indene-1,4'-piperidin]-1'-ylmethyl)-8-(hydroxymethyl)-3,4-dihydroquinolin-2(1H)-one; 8-chloro-3-(2,3-dihydro-1'H-spiro[indene-1,4'-piperidin]-1'-ylmethyl)-3,4-dihydroquinolin-2(1H)-one; 5-chloro-3-(2,3-Dihydro-1'H-spiro[indene-1,4'-piperidin]-1'-ylmethyl)-3,4-dihydroquinolin-2(1H)-one; 8-(aminomethyl)-3-(2,3-dihydro-1'H-spiro[indene-1,4'-piperidin]-1'-ylmethyl)- -3,4-dihydroquinolin-2(1H)-one and a pharmaceutically acceptable salts and solvates thereof.

A preferred individual compound of formula I of this invention is selected from 6-(2,3-dihydro-1'H-spiro[indene-1,4'piperidin]-1'-ylmethyl)-6,7-dihydro-5H-[1,4]oxazino[2,3,4-ij]quinolin-3(2H)-one; 6-(2,3-dihydro-1'H-spiro [indene-1,4'-piperidin]-1'-ylmethyl)-1,2,6,7-tetrahydro-3H,5H-pyrido[3,2,1-ij]quinazolin-3-one and a pharmaceutically acceptable salts and solvates thereof.

A compound of formula I wherein $R^{12}$ and $R^{13}$ taken together with the three ring atoms of the dihydro- or tetrahydro-quinoline ring separating said substituents form a five to seven membered ring may be also represented by formula Ia:

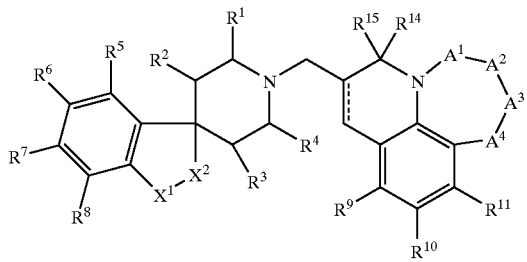

Ia wherein $A^1$—$A^2$—$A^3$—$A^4$ represents a fully saturated, partially unsaturated or fully unsaturated two to four membered carbon chain wherein $A^1$ must be a carbon atom, one or two of $A^2$ through $A^4$ are optionally absent, and one of $A^2$ through $A^4$ is optionally replaced with a nitrogen, oxygen or sulfur atom (preferably with a nitrogen or oxygen atom) and one or two of the carbon and nitrogen atoms in the chain are optionally substituted with substituents independently selected from oxo; hydroxy; $(C_1-C_6)alkyl$; $(C_1-C_6)alkyl$ substituted with one to five halo which may be same or different; $(C_1-C_6)alkyl$ substituted with one to five substituents independently selected from the group consisting of hydroxy, amino, $[(C_1-C_6)alkyl]NH—$, $[(C_1-C_6)alkyl]_2N—$, $H_2NC(=O)—$, $[(C_1-C_6)alkyl]NHC(=O)—$, $[(C_1-C_6) alkyl]_2NC(=O)—$, $(C_1-C_6)alkoxy$ and a fully saturated five to six membered heterocyclyl containing one to two hetero atoms independently selected from nitrogen and oxygen; $(C_1-C_6)alkoxy$; $(C_1-C_6)alkoxy$ substituted with one to five halo which may be same or different; $(C_1-C_6)alkoxy$ substituted with one to five substituents independently selected from the group consisting of hydroxy, amino, $[(C_1-C_6)alkyl]NH—$, $[(C_1-C_6)alkyl]_2N—$, $H_2NC(=O)—$, $[(C_1-C_6)alkyl]NHC(=O)—$ and $[(C_1-C_6)alkyl]_2NC(=O)—$; amino; $[(C_1-C_6)alkyl]NH—$; and $[(C_1-C_6)alkyl]_2N—$; and the bond between the nitrogen ring in the quinoline ring and $A^1$ is preferably a single bond, and $R^1$ through $R^{11}$, $R^{14}$, $R^{15}$, $X^1$ and $X^2$ are defined as above. The more preferred compounds of formula (Ia) of this invention are those compounds wherein $A^1$—$A^2$—$A^3$—$A^4$ represents a fully saturated two to four membered carbon chain and one or two of $A^2$ through $A^4$ are optionally absent, and one of $A^2$ through $A^4$ is optionally replaced with a nitrogen or oxygen atom and one of the carbon atom is optionally substituted with substituent selected from oxo and hydroxy.

Accordingly, this invention relates to a pharmaceutical composition comprising an effective amount of a compound of formula I defined as above and a pharmaceutically acceptable carrier for treating a disease or medical condition mediated by ORL1-receprot and its endogeneous ligand in a mammal including a human.

A preferred pharmaceutical composition of this invention comprises a compound of formula I defined as above having selectivity for ORL-1 receptor.

A further preferred pharmaceutical composition of this invention comprises a compound of formula I defined as above having antagonist effect for ORL-1 receptor.

A further preferred pharmaceutical composition of this invention comprises a compound of formula I defined as above which is a selective antagonist for ORL-1 receptor.

Therefore, a pharmaceutical composition of this invention comprising a compound of formula I defined as above is useful for treating or preventing a disease or medical condition selected from pain; eating disorders including anorexia and bulimia; anxiety and stress conditions; immune system diseases; locomotor disorder; eating disorder; memory loss, cognitive disorders and dementia including senile dementia and those diseases caused by Alzheimer's disease, Perkinson's disease or other neurodegenerative pathologies; epilepsy or convulsion and symptoms associated therewith; a central nervous system disorder related to gulutamate release action, anti-epileotic action, disruption of spatial memory, serotonin release, anxiolytic action, mesolimbic dopaminergic transmission, rewarding propaerties of drug of abuse, modulation of striatal and glutamate effects on locomotor activity; cardiovascular disorders hypotension, bradycardia and stroke; renal disorders including water excretion, sodium ion excretion and syndrome of inappropriate secretion of antidiuretic hormone (SIADH); gastrointestinal disoders; airway disorders including adult respiratory distress syndrome (ARDS); autonomic disorders including suppression of micturition reflex; metabolic disorders including obesity; cirrhosis with ascites; sexsual dysfunctions; and altered pulmonary function including obstructive pulmonary disease.

This invention also relates to a method for treating or preventing a disease or condition in a mammal including a human, which disease or condition is mediated by ORL-1 receptor and its endogeneous ligand, comprising administering an effective amount of a compound of formula I defined as above to a mammal including a human, which suffered from such disease or condition.

More specifically, this invention relates to a method for treating or preventing the aforementioned disease or medical condition, wherein said compound has selectivity for ORL-1 receptor.

More specifically, this invention relates to a method of treating or preventing the aforementioned disease or medical condition, wherein said compound has antagonist effect for ORL-1 receptor.

More specifically, this invention relates to a method for treating or preventing the aforementioned disease or medical condition, wherein said compound is a selective antagonist for ORL-1 receptor.

Accordingly, this invention relates to a method for treating or preventing the aforementioned disease or medical condition wherein said disease or condition is selected from pain; eating disorders including anorexia and bulimia; anxiety and stress conditions; immune system diseases; locomotor disorder; eating disorder; memory loss, cognitive disorders and dementia including senile dementia and those diseases caused by Alzheimer's disease, Perkinson's disease or other neurodegenerative pathologies; epilepsy or convulsion and symptoms associated therewith; a central nervous system disorder related to gulutamate release action, antiepileotic action, disruption of spatial memory, serotonin release, anxiolytic action, mesolimbic dopaminergic transmission, rewarding propaerties of drug of abuse, modulation of striatal and glutamate effects on locomotor activity; cardiovascular disorders hypotension, bradycardia and stroke; renal disorders including water excretion, sodium ion excretion and syndrome of inappropriate secretion of antidiuretic hormone (SIADH); gastrointestinal disoders; airway disorders including adult respiratory distress syndrome (ARDS); autonomic disorders including suppression of micturition reflex; metabolic disorders including obesity; cirrhosis with ascites; sexsual dysfunctions; and altered pulmonary function including obstructive pulmonary disease.

General Synthesis

The compounds of formula I of the present invention may be prepared according to known preparation methods, or General Procedures or preparation methods illustrated in the following reaction Schemes. Unless otherwise indicated $R^1$ through $R^{15}$, $X^1$ and $X^2$ and $A^1$ through $A^4$ in the reaction Schemes and discussion that follow are defined as above. Unless otherwise indicated, reactions in this specification may be carried out at about ambient pressure (i.e., 760 mmHg) and about room temperature (i.e., 25° C.).

Typical preparation procedures for compounds of formula I of the present invention are as follow:

Protecting Groups

Amino, hydroxy, mercapto or the like may be protected with a protecting group, and the protectinng group may be subsequently removed in an appropriate reaction step according to a known procedure (e.g., Protective Groups in Organic Synthesis edited by T. W. Greene et al. (John Wiely & Sons, 1991)). For example, a primary or a secondary amine may be typically protected by reaction with benzyl chloride and $K_2CO_3$, and the benzyl group (abbreviated as Bn) may be removed by catalytic hydrogenation over palladium-carbon. Introduction of t-butoxycarbonyl (abbreviated as Boc) to amino group may be carried out using $(BOC)_2O$ under basic condition, and the protecting group may be removed in HCl/EtOAc. Hydroxy may be protected with t-butyldimethylsilyl (abbreviated as TBS or TBDMS) in alkylation using NaH. The protecting group may be introduced with TBDMSCl and imidazole in DMF and removed using an appropriate reagent such as tetrabutylammonium fluoride.

Leaving Groups/Introductions of Sulfonyl Groups

Leaving group used in a reaction described hereafter are known to those skilled in the art. These leaving groups include halo such as Cl, Br and I; sulfonic esters such as TfO (triflates), MsO (mesylates), TsO (tosylates); and the like. These groups may be introduced to an appropriate compound according to methods known to those skilled in the art (e.g., (a) halogenation using triphenylphosphine/ $CX_4$ wherein X is halo ($PPh_3/CX_4$); (b) reaction with TsCl; and (c) reaction with MsCl).

Halogenations

Carboxylic acids or alcohols may be converted to alkyl or acyl halides using halogenation reagents. Conversions of alcohols or carboxylic acids respectively to alkyl halides or acyl halides may be typically carried out using $SOCl_2$, $PCl_5$, $PCl_3$, $POCl_3$, HBr, $PBr_3$, HI or the like.

Alkylations

Alkylations may be carried out according to a procedure known to those skilled in the art. More specifically, a primary or secondary amine may be alkylated to a secondary or tertialy amine with a halo alkyl (preferably as a bromide or iodide compound) in the presence of an alkali metal ion such as potassium ion, base or a mixture thereof. This alkylation may be also carried out using a nucleophilic strong base that serves to remove the proton of the secondary amine radical. Instead of halides, sulfates or sulfonates may be used in these reactions. Alkylations of alcohols may be carried out using diazo compounds preferably in the presence of a catalyst such as fluoboric acid ($HBF_4$) or silica gel. For the alkylations, suitable solvents include polar aprotic solvents such as dimethylformamide (DMF), dimethylsulfoxide, acetonitrile (MeCN), acetone, sulfur dioxide, dichloromethane, hexane and the like; and protic solvents such as water, alcohols such as methanol (MeOH) and ethanol (EtOH), ethylene glycol and the like, or a combination thereof. These reactions may be typically carried out at a temperature from about 0° C. to the reflux temperature of a solvent to be used for from about 1 minute to 30 hours.

Aminations

Aminations of alkanols or alkyl halides may be carried out by reactions with cyclic imide compounds such as N-phthalimides followed by hydrazinolysis or hydrolysis. If required, the reactions with phthalimides may be carried out using organophosphorous reagents with or without azo compounds.

Amidations

If appropriate, a base such as triethylamine, or a base catalysis such as N,N-dimethylaminopyridine (DMAP), 4-pyrrolidinopyridine (PPY) or the like may be employed in this reaction. Suitable solvents for this reaction include hexane, dichloromethane, tetrahydrofuran (THF), pyridine and the like.

Amidation-1—Acylayion of Amines by Acyl Halides

Acyl halids may be treated with ammonia or amines for the preparation of amides. This reaction may be carried out and in the presence or absence of an aqueous alkali which may capture the liberated halide ion and controlled by cooling or dilution. Acyl halide may also be reacted with arylamines, hydrazine or hydroxylamine under the similar conditions. Amino protections using carbobenzoxy group (abbreviated as Cbz) or t-butoxycarbonyl group (abbreviated as Boc) may be carried out in this way.

Amidation 2—Acylation of Amines by Anhydride

This reaction may be carried out with ammonia or primary or secondary amines according to a similar procedure described in Amidation 1 above. Ammonia and primary amines may give imides including cyclic imides, wherein two acyl groups are attached to the nitrogen.

Amidation 3—Acylation of Amines by Carboxylic Acids

Carboxylic acids may be treated with ammonia or amine compounds to give amides. This amidation may be carried out in the presence of a coupling agent with or without an additional base at about room temperature. A coupling agent such as dicyclohexylcarbodiimide (DCC) used in a peptide synthesis may be applied to the amidations. Other suitable coupling agents used in these amidations include N,N'-carbonyldiimidazole (CDI), diisopropylcarbodiimide (DIPC), 1-ethyl-3-(3-dimethylaminopropyl) carbodiimide (WSC, water soluble carbodiimide), benzotriazole-1-yloxy-tris(dimethylamino)phosphonium hexafluorophosphate (BOP) and diphenylphosphorylazide (DPPA) and the like. A cyclic amine may be acylated according to a method analogous to these amidations. If amines are subjected to this reaction in its halogen salt forms, additional amines may be used for trapping hydrogen halides formed.

Amidation 4—Acylation of Amines by Carboxylic Esters

Carboxylic esters may be converted to unsubstituted, N-substituted or N,N-disubstituted amides. This reaction may be carried out in the presence of a strong base catalysis as well as catalysis by cyanide ion under a high pressure. Hydrazides and hydroxamic acids may be prepraed from carboxylic esters with hydrazine and hydroxylamine respectively under similar reaction conditions.

Amidation 5—Acylation of Amines by Amides or Other Acid Derivatives

A salt of an amine may be subjected to this reaction. In this reaction, $NH_2$ usually acts as a leaving group. Secondary and primary amines (in the form of their salts) are the most common reagents in this reaction. Acid derivatives, which may be converted to amides, include thiol acids, thiol ethers, acyloxyboranes, 1,1,1-trihalo ketones, α-keto nitrils, acyl azides and the like.

These amidations may be carried out in a reaction inert solvent such as dichloromethane ($CH_2Cl_2$), alcohols such as methanol, ethanol or buthanol (BtOH), acetonitrile, tetrahydrofuran (THF), dimethylfolmamide (DMF), or pyridine or a combination thereof, at a temperature from about 0° C. to the reflux temperature of a solvent, for from about 5 minutes to 48 hours.

Hydrolysis of Esters

Hydrolysis of esters may be carried out in the presence of an acid, base, metal ion, enzyme or nucleophile according to a method known to those skilled in the art. The hydrolysis of esters may be carried out in a reaction inert solvent at a temperature from about 0° C. to the reflux temperature of the solvent for from about 1 to 24 hours. Suitable solvents for the reactions include alcohols such as methanol, ethanol, tetrahydrofuran, acetic acid and the like.

Esterifications

Carboxylic acids and alcohols afford esters using acid catalysis. Typical catalysis for this reaction include conc. HCl, anhydrous sulfuric acid, p-toluenesulfonic acid and the like. The alcohol generally servers as the solvent, but other reaction inert solvent such as toluene or xylene may be used. The alcohol may be used in large excess, and the water from the reaction mixture may be removed.

Reductions

Reductions may be carried out using reducing agents. Typical reducing agents are lithium aluminum hydride (LAH), lithium triethylborohydride ($LiEt_3BH$), a complex formed from lithium trimethoxyaluminum hydride ($LiAlH(OMe)_3$) and CuI, diisobutylaluminium hydride (DIBAL) and lithium bis(trimethylsilyl)amide (LHMDS). Typical milder reducing agents are $NaBH_4$ and the like in a dipoler aprotic solvent such as $Me_2SO$, DMF or sulfolane. Other reducing agents are zinc with acid or base, $SnCl_2$, chromium(II) ion and the like. For example, carboxylic acids may be reduced to primary alcohols by $LiAlH_4$ at about room temperature, and nitro group may be reduced to amino group by reaction with zinc.

These reactions may be used for modifying compounds obtained or used in the following synthetic methods.

Schemes 1-1 through 1-6 illustrate embodiments of preparation process for a compound of formula (I).

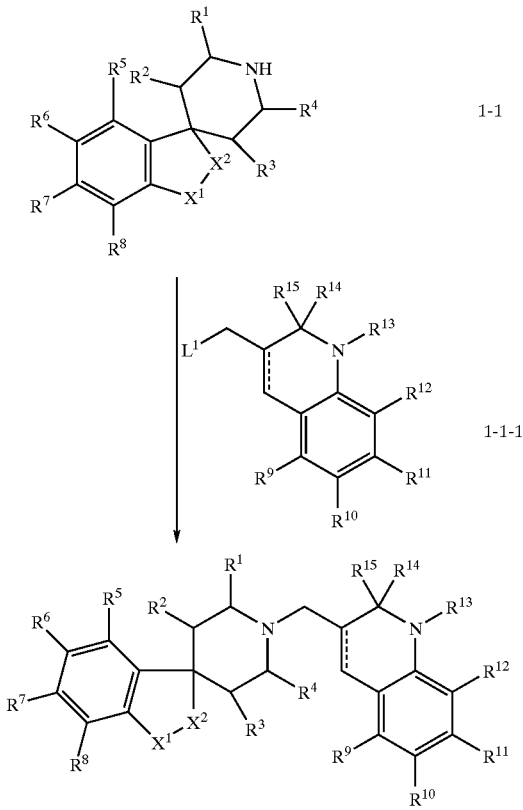

Scheme 1-1 illustrates a preparation method of a compound of formula I of the present invention. This method comprises alkylation of a spiro-piperidine compound of formula 1-1 by a compound of formula 1-1-1 wherein $L^1$ is a leaving group. In a preferred embodiment of this reaction, a compound of formula 1-1 may be subjected to the alkylation as a salt such as a hydrochroride. A preferred compound of formula 1-1-1 for this reaction may be a sulfonate such as MsO. This alkylation may be preferably carried out in the presence of a base in a reaction inert solvent at a temperature from about room temperature to about the reflux temperature of the solvent for from about 10 minutes to 48 hours. Suitable bases for this reaction include N,N-diisopropylethylamine, potassium carbonate and the like. Suitable solvents for this reaction include THF, isopropyl alcohol (i-PrOH), ethylene glycol, DMF and the like.

A compound of formula 1-1 may be a known compound or readily prepared by known methods (e.g., *J. Med. Chem.*, 1992, 35, 2033). A compound of formula 1-1-1 may be prepared by known methods (e.g., *J. Chem. Soc., Perkin Trans.*, 1, 1017 (1997)).

Scheme 1-2 illustrates another preparation method of a compound of formula (I).

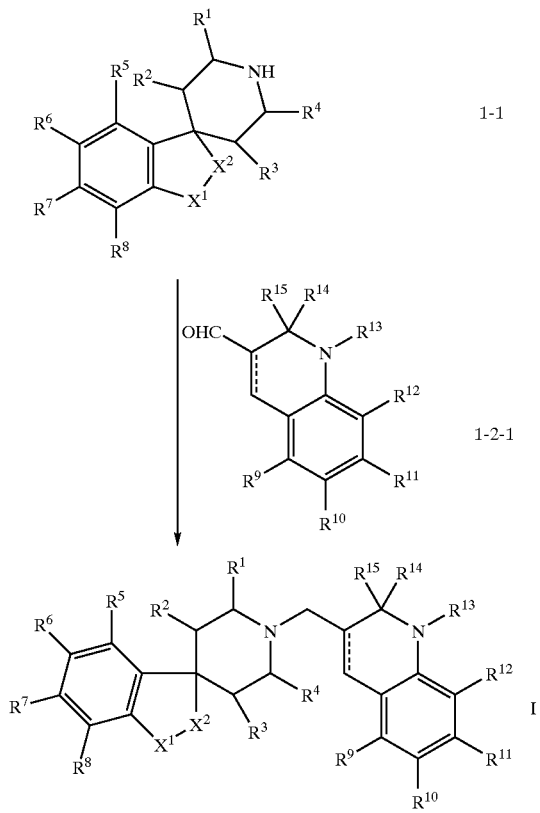

In this reaction, a compound of formula 1-1 may be reacted with an aldehyde compound of formula 1-2-1. This reductive amination may be carried out in the presence of a hydride reagent in a reaction inert solvent at about 0° C. for from about 10 minutes to 48 hours. A preferable hydride reagent for this reaction may be sodium triacetoxyborohydride (NaBH(OAc)$_3$), and a preferable reaction inert solvent for this reaction may reaction be THF or CH$_2$Cl$_2$. This reaction may be preferably carried out in the presence of a catalytic amount of acetic acid (AcOH). This reaction may be carried out using sodium cyano borohydride (NaBH$_3$CN) in alcohol at acidic condition.

A compound of formula 1-2-1 may be prepared by a reducing a corresponding carboxylic acid or its ester compound. This reduction may be typically carried out using i-Bu$_2$AlH (DIBALH) in a reaction inert solvent such as CH$_2$Cl$_2$ at about 0° C. If required, the carboxylic acid may be converted to a corresponding acyl halide with an appropriate halogenation reagent such as thionyl chloride prior to said reduction. A compound of formula 1-2-1 may be prepared by known method (e.g., *Synthesis* (1995), 1362).

Scheme 1-3 illustrates another preparation method of a compound of formula (I) wherein $R^{14}$ and $R^{15}$ together represent oxo.

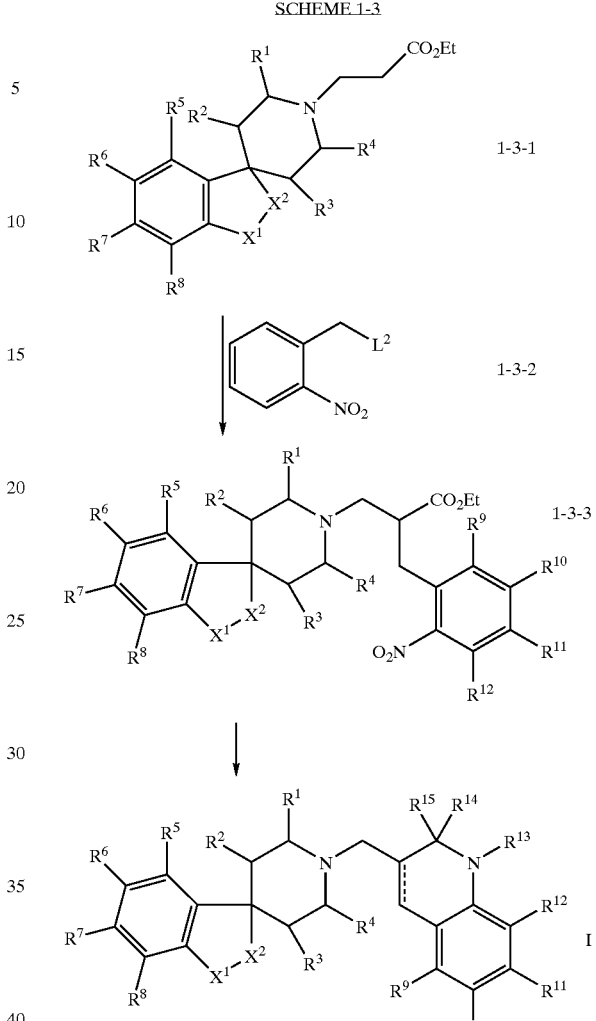

According to this reaction scheme, a compound of formula 1-3-1 may be subjected to alkylation with a nitrobenzene compound of formula 1-3-2 wherein $L^2$ is a leaving group such as halo to give a compound of formula 1-3-3, then the compound thus obtained may be reduced to the compound of formula I. The alkylation may be carried out by treating a compound of formula 1-3-1 with a strong base such as lithium bis(trimethylsilyl)amide or lithium diisopropylamide and reacted with a compound of 1-3-2 to give a compound of formula 1-3-3. Then, the compound of 1-3-3 thus obtained may be cyclized by reduction of the nitro group to a compound of formula I. The treatment of a compound of formula 1-3-1 with a base and the subsequent reaction with a compound of formula 1-3-2 may be carried out at a temperature from about −78° C. to 0° C., preferably from about −78° C to about −40° C. in a reaction inert solvent such as THF for from about 10 minutes to 48 hours. The reduction of a compound of formula 1-3-3 to give a compound of formula I may be carried out by catalytic hydrogenation using a metal catalyst in a reaction inert solvent at a temperature from about 0° C. to the reflux temperature of the solvent used for from about 10 minutes to 48 hours. A typical metal catalyst is such as palladium catalyst.

A compound of formula 1-3-1 may be prepared by reacting a compound of 1-1 with ethyl 3-bromopropionate and N,N-diisopropylethylamine in a reaction inert solvent such as EtOH at a temperature from about room temperature to about 100° C. for about 1 to 24 hours. A compound of formula 1-3-2 is a known compound or readily prepared by known method.

Scheme 1-4 illustrates preparation methods of the compounds of formula I comprising reacting a spiro piperidine derivative of formula 1-4-1 with an acrylate derivative of formula 1-4-2, coupling the compound thus obtained with a nitrobenzenene compound of formula 1-4-3 and quinoline ring formation.

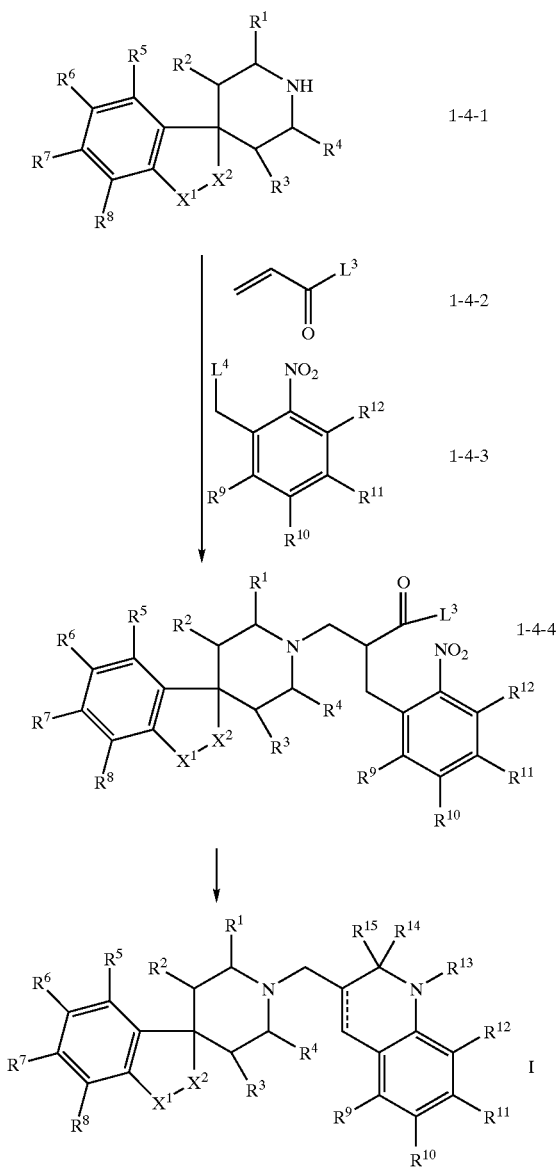

The reaction of compounds of formula 1-4-1 with the compounds of formula 1-4-2, wherein $L^3$ is a leaving group such as $(C_1-C_6)$alkyl-O may be carried out in the presence of a base such as triethylamine, or diisopropylethylamine, in a reaction inert solvent at a temperature from about room temperature to the reflux temperature of the solvent used for from about 30 minutes to 24 hours. The resulting compound may be subjected to coupling reaction with a compound of formula 1-4-3 to afford the compound of formula 1-4-4. This reaction may be carried out in the presence of a strong base such as lithium bis(trimethylsilyl)amide (LHMDS), lithium diisopropylamide (LDA) or the like, in a reaction inert solvent at a temperature from −100° C. to room temperature for from about 10 minutes to 24 hours. This reaction may be preferably carried out further in the presence of a cosolvent used in alkylation to enhance reactivity, selectivity and solubility such as 1,3-dimethyl-3,4,5,6-tetrahydro-2(1H)-pyrimidinone (DMPU). Examples of suitable solvents in the above reactions include: aliphatic hydrocarbons, such as hexane, heptane and petroleum ether; aromatic hydrocarbons, such as benzene, toluene and xylene; halogenated hydrocarbons, such as methylene chloride, chloroform, carbon tetrachloride and dichloroethane; and ethers, such as diethyl ether, diisopropyl ether, tetrahydrofuran and dioxane.

The quinoline ring formation in the compound of formula 1-4-4 may be carried out under a reduction condition such as a catalytic reduction. Suitable reduction condition may be Pd catalyzed hydrogenation under hydrogen atmosphere in a reaction inert solvent at around room temperature for from about 30 minutes to 24 hours. Examples of suitable solvents include alcohols, such as methanol, ethanol, propanol, isopropanol and butanol; and organic acids, such as acetic acid and propionic acid. This reduction may be also carried out using an iron catalyst in the acidic solvent at a temperature from about room temperature to the reflux temperature of the solvent for from about 1 to 24 hours. Examples of suitable solvents include alcohols, such as methanol, ethanol, propanol, isopropanol and butanol; and organic acids, such as acetic acid and propionic acid. This reaction may be carried out in the presence of a base such as triethylamine at around room temperature for about 30 minutes to 24 hours. Examples of suitable solvents include: aliphatic hydrocarbons, such as hexane, heptane and petroleum ether; aromatic hydrocarbons, such as benzene, toluene and xylene; halogenated hydrocarbons, such as methylene chloride, chloroform, carbon tetrachloride and dichloroethane; and ethers, such as diethyl ether, diisopropyl ether, tetrahydrofuran and dioxane.

The nitrobenzene compounds of formula 1-4-3 may be prepared according to known methods such as those described in journal literature (e.g., R. Zamboni et al., Can. J. Chem, 1978, 56, 2725; A. L. Davis et al., J. Med Chem. 1975, 18, 752; J. L. Neumeyer et al., J. Med. Chem., 1976, 19, 25; T. J. McCord et al., J. Heterocycl. Chem., 1982, 19, 401 etc.).

Scheme 1-5 illustrates preparation methods for formula I, wherein $R^{14}$ and $R^{15}$ together form oxo, by formation of tetrahydroquinoline or dihydroquinolin ring followed by coupling reaction with an appropriate spiro piperidine compound (see Scheme 1-5).

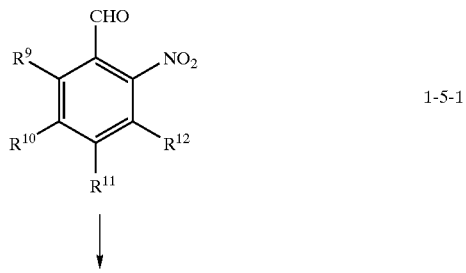

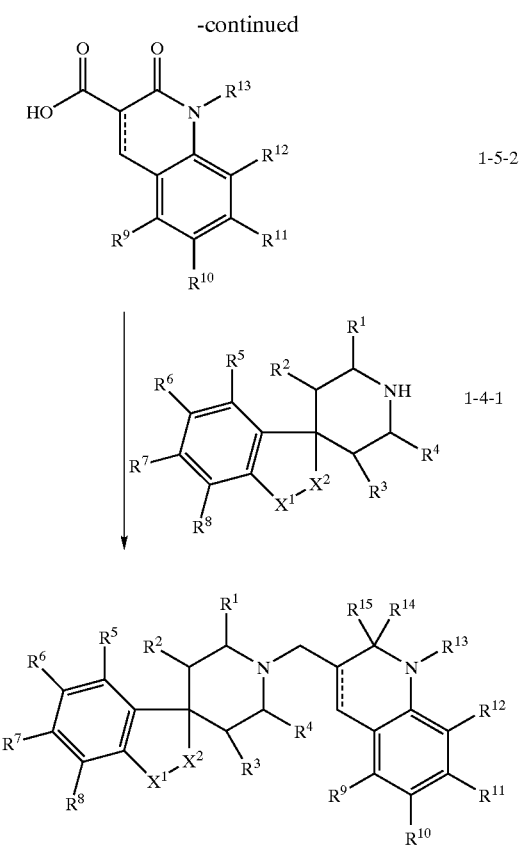

1-5-2

1-4-1

I

The nitrobenzene compounds of formula 1-5-1 may be reacted with a malonic ester and reduced to the compounds of formula 1-5-2. The reaction between the compounds of formulas 1-5-1 a malonic ester may be carried out in the presence of a base such as piperidine or triethylamine in a reaction inert solvent at about the reflux temperature of the solvent for about 1 to 24 hours. Examples of suitable solvents include: aliphatic hydrocarbons, such as hexane, heptane and petroleum ether; aromatic hydrocarbons, such as benzene, pyridine, toluene and xylene; and halogenated hydrocarbons, such as methylene chloride, chloroform, carbon tetrachloride and dichloroethan. The compounds thus obtained may be extracted and subjected to a suitable reduction to give the compounds of formula 1-5-2. The reduction may be carried out using a metal catalyst at from about 0° C. to the reflux temperature of the solvent used for from about 10 minutes to 48 hours. This reduction may typically be carried out under known conditions such as Pd catalyzed hydrogenation or Fe catalyzed reduction in an acidic condition. The compound thus obtained may be coupled with the compounds of formula 1-4-1 to give the compounds of formula I under amidation conditions using a coupling agent at a temperature from about 0° C. to the reflux temperature of the solvent used for from about 10 minutes to 48 hours. Typically, the amidation may be carried out using a suitable coupling agent such as WSC.

Depending on $R^{12}$, a different leaving group may be introduced to the compounds of formula 1-5-2 prior to the coupling with the compounds of formula 1-4-1. The carboxy in the compounds of formula 1-5-2 may be reduced to hydroxymethyl, and the hydroxy may be replaced with a leaving group such as TfO, MsO or TsO. The reduction may be carried out using a reducing reagent such as lithium reducing reagent or DIBAL. The introduction of such leaving groups may be carried out under known conditions. For example, introduction of MsO may be carried out in pyridine or using triethylamine in a reaction inert solvent such as dichloromethane. Then, the compounds thus obtained may be coupled with the compounds of formula 1-4-1 to give the compounds of formula I in the presence of a base such as triethylamine or N,N-diisopropylethylamine in a reaction inert solvent such as ether.

Other hydroxymethyl derivative of the compounds of formula 1-5-2 may be prepared according to known methods (e.g., A. Claesson et al., Bioorg. Med. Chem. Lett., 1996, 6, 1635).

The tricyclic compounds of formula Ia may be prepared by cyclization between $R^{12}$ and $R^{13}$ of appropriate compounds of formula I. Depending on desired ring members and their positions in the tricyclic ring, both or either of $R^{12}$ and $R^{13}$ may be replaced with appropriate substituents prior to the cyclization. In case carbonyl group(s) are contained in $R^{12}$, $R^3$ or the substituents replacing with $R^{12}$ and/or $R^{13}$, these groups may be cyclized to give the compounds of formula Ia containing the corresponding carbonyl group(s) in the tricyclic ring. This reaction may be carried out under known conditions used in acylation of alkenes by carboxylic acid or their derivatives. For example, this reaction may be typically carried out using a protic acid such as polyphosphoric acid (PPA) at around 100° C. for about 30 minutes to 24 hours. The compounds of formula I, wherein $R^{12}$ is hydroxy or a substituent comprising hydroxy and $R^{13}$ is hydrogen or substituent comprising amino, may be subjected to cyclization under known acylation conditions of amines by carboxylic acids to afford the corresponding tricyclic compound of formula Ia. This reaction may be carried out using a coupling agent such as CDI or WSC in a reaction inert solvent such as THF at a temperature from about 0° C. to about room temperature. If an appropriate leaving group is introduced to $R^{13}$ and $R^{12}$ is hydroxy or a substituent comprising hydroxy in the compound of formula I, the compound may be subjected to cyclization under known alkylcation conditions to give the corresponding compounds of formula Ia.

The compounds of formula Ia may be prepared by quinoline ring formation of an appropriate starting material to give the tricyclic ring and coupling reaction with a compound of formula 1-4-1 as described in Scheme 1-6.

Scheme 1-6

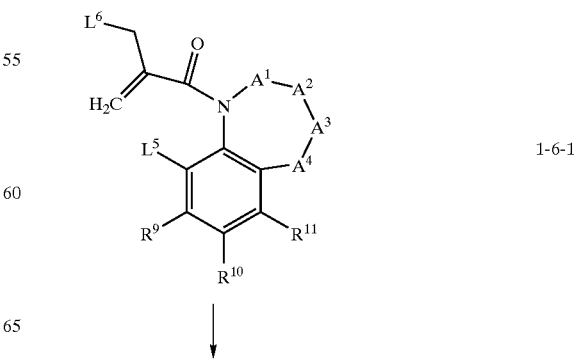

1-6-1

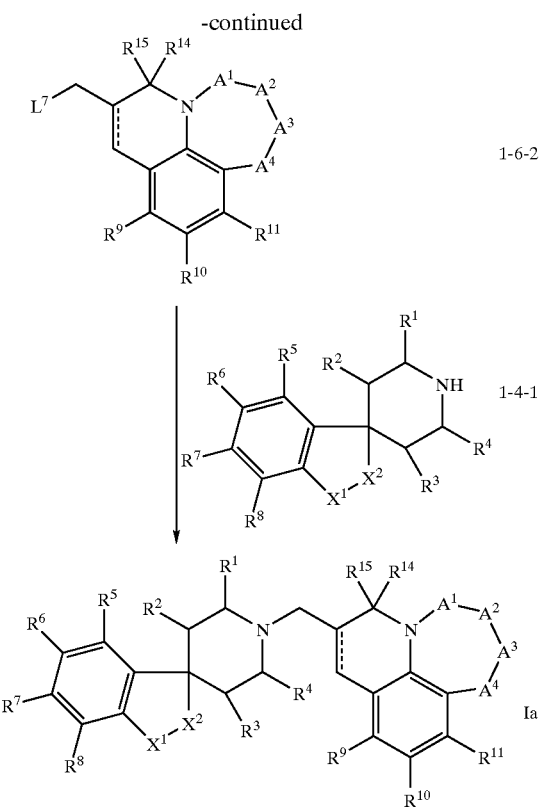

The compounds of formula 1-6-1 wherein $L^5$ and $L^6$ are each independently leaving groups. These compounds may be prepared by according to known procedures (e.g., J. Med. Chem. 1998, 41, 3539 and Tet. Lett., 1993, 34, 6185). The compounds of formula 1-6-1 may be reduced to the compounds of formula 1-6-2 under known conditions such as Pd catalyzed hydrogenation, and an appropriate leaving group $L^7$ may be introduced to the compound obtained. Then, the compound thus obtained may be coupled with a compound of formula 1-4-1 to yield the compound of formula Ia under similar conditions described as above (i.e., amidation using a metal catalyst at a temperature from about 0° C. to the reflux temperature of the solvent for from about 10 minutes to 48 hours).

If required, substituents of compounds of formula I obtained as above may be further modified by reactions described in this specification or known methods.

All of the above reactions and preparations of novel starting materials using in the preceding methods are conventional and appropriate reagents and reactions for their performance or preparation as well as procedures for isolating the desired products will be well-known to those skilled in the art with reference to literature precedents and the Examples and Preparations hereto.

A pharmaceutically acceptable salt of a compound of the formula (I) may be readily prepared by mixing together solutions of a compound of the formula (I) and the desired acid or base, as appropriate. The salt may precipitate from solution and be collected by filtration or may be recovered by evaporation of the solvent.

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assay. Tritiated, i.e., $^3H$, and carbon-14, i.e., $^{14}C$, isotopes are particularly preferred for their ease of presentation and detectability. Further, substitution with heavier isotopes such as deutrium, i.e., $^2H$, can afford therapeutic advantage resulting from greater metabolic stability, for example increased in vivo half-life or reduced dosage requirement and, hence, may be preferred in some circumstances. Isotopically labelled compounds of formula (I) of this invention and prodrugs thereof can generally be prepared by carrying out the procedure disclosed in above-disclosed Schemes and/or Examples and Preparations below, by submitting a readily available isotopically labelled reagent for a non-isotopically labeled reagent.

The compounds of Formula (I) of this invention are basic, therefore they will form acid-addition salts. All such salts are within the scope of this invention. However, it is necessary to use an acid addition salt which is pharmaceutically-acceptable for administration to a mammal. The acid-addition salts can be prepared by standard methods. For example, the salts may be prepared by contacting the basic compounds with acid in substantially equivalent proportions in water or an organic solvent such as methanol or ethanol, or a mixture thereof. The salts can be isolated by crystallization from or evaporation of the solvent. Typical salts which can be formed are the hydrochloride, nitrate, sulfate, bisulfate, phosphate, acetate, lactate, citrate, tartrate, succinate, maleate, fumarate, gluconate, saccharate, benzoate, methanesulfonate, ethanesulfonate, benzenesulfonate, p-toluenesulfonate, oxalate and pamoate (1,1'-methylene-bis-(2-hydroxy-3-naphtoate)) salts.

Suitable base salts are formed from bases which form non-toxic salts and examples are the sodium, potassium, aluminum, calcium, magnesium, zinc and diethanolamine salts.

For a review of on suitable salts see Berge et al., J. Pharm. Sci., 66, 1–19, 1977.

The pharmaceutically acceptable solvates of the compounds of the formula I or salts thereof include the hydrate thereof Also included within the present scope of the compounds of the formula I are polymorphs thereof and tautomer thereof.

The compounds of Formula (I) have been found to possess selective affinity for ORL1-receptors and ORL-1 receptor antagonist activity. Thus, these compounds are useful as an analgesic, anti-inflammatory, diuretic, anesthetic, neuroprotective, anti-hypertensive and anti-anxiety agent, and the like, in mammalian subjects, especially humans in need of such agents. The affinity, antagonist activities and analgesic activity can be demonstrated by the following tests respectively.

Selective Affinity for ORL1-receptors
ORL1-Receptor Binding Assay
The human ORL1receptor transfected HEK-293 cell membranes were incubated for 45 min at 22° C. with 0.4 nM [$^3H$]nociceptin, 1.0 mg of wheat germ agglutinin-coated SPA beads and various concentrations of test compounds in a final volume of 200 μl of 50 mM HEPES buffer pH7.4 containing 10 mM $MgCl_2$ and 1 mM EDTA. Non-specific binding was determined by the addition of 1 μM unlabeled nociceptin. After the reaction, the assay plate was centrifuged at 1,000 rpm for 1 min and then the radioactivity was measured by a Liquid Scintillation Counter.

μ-Receptor Binding Assay

The human Mu receptor transfected CHO-K1 cell membranes were incubated for 45 min at 22° C. with 1.0 nM [$^3$H]DAMGO, 1.0 mg of wheat germ agglutinin-coated SPA beads and various concentrations of test compounds in a final volume of 200 μl of 50 mM Tris-HCl buffer pH7.4 containing 5 mM $MgCl_2$. Non-specific binding was determined by the addition of 1 μM unlabeled DAMGO. After the reaction, the assay plate was centrifuged at 1,000 rpm for 1 min and then the radioactivity was measured by a Liquid Scintillation Counter.

Each percent non specific binding thus obtained is graphed as a function of compound concentration. A sigmoidal curve is used to determine 50% bindings (i.e., $IC_{50}$ values).

In this testing, the preferred compounds prepared in the working examples appearing hereafter demonstrated higher binding affinity for ORL1-receptors than for mu-receptors.

$$IC_{50}(\text{ORL1-receptors})nM/IC_{50}(\text{mu-receptors})nM < 1.0$$

ORL1 Receptor Functional Assay

The human ORL1 receptor transfected HEK-293 cell membranes are incubated with 400 pM [$^{35}$S]GTPγS, 10 or 50 nM nociceptin and various concentrations of test compounds in assay buffer (20 mM HEPES, 100 mM NaCl, 5 mM $MgCl_2$, 1 mM EDTA, 5 mM GDP, 1 mM DTT, pH7.4) containing 1.5 mg of wheat germ agglutinin-coated SPA beads for 60 or 90 min at 25° C. in a final volume of 200 μl. Basal binding is assessed in the absence of nociceptin and non-specific binding is defined by the addition of unlabelled 10 mM GTPγS. Membrane-bound radioactivity is detected by a Liquid Scintillation Counter. In this test, the title compounds of Examples 20 and 31 showed $IC_{50}$ value of 13 nM at 10 nM nociceptin stimulation.

Analgesic Tests

Tail Flick Test in Mice

The latency time to withdrawal f the tail from radiant heat stimulation is recorded before and after administration of test compounds. Cut-off time is set to 8 sec.

Acetic Acid Writhing Test in Mice

Acetic acid saline solution of 0.7% (v/v) is injected intraperitoneally (0.16 ml/10 g body weight) to mice. Test compounds are administered before acetic acid injection. As soon as acetic acid injection, animals are placed in a 1 liter beaker and writhing is recorded for 15 min.

Formalin Licking Test in Mice

Formalin-induced hind paw licking is initiated by a 20 micro liters subcutaneous injection of a 2% formaline solution into a hind paw of mice. Test compounds are administered prior to formalin injection. Total licking time is recorded for 45 min after formalin injection.

Carrageenan-Induced Mechanical Hyperalgesia Test in Rats

The response to mechanical nociceptive stimulus is measured using an algesiometer (Ugo Basile, Italy). The pressure is loaded to the paw until rats withdrawal the hind paw. Lambda-Carrageenan saline solution of 1% (w/v) is injected subcutaneously into the hind paw and the withdrawal response is measured before and after the injection. Test compounds are administered at appropriate time point.

Carrageenan-Induced Thermal Hyperalgesia Test in Rats

The response to thermal nociceptive stimulus is measured using an plantar test apparatus (Ugo Basile, Italy). The radiant heat stimuli is applied to the paw until rats withdrawal the hind paw. Lambda-Carrageenan saline solution of 2% (w/v) is injected subcutaneously into the hind paw and the withdrawal response is measured before and after the injection. This testing method is described in K. Hargreaves, et al., Pain 32:77–88, 1988.

Chronic Contriction Injury Model (CCI Model)

Chronic contriction injury is made according to Bennett's method (Bennett, et al., Pain 83:169–182, 1999). Tactile allodynia in rats is assessed using the von Frey hairs (Stoelting, Ill.) before and after administration with test compounds.

Partial Sciatic Nerve Ligation Model (PSL)

This test may be conducted according to similar procedures described by Z. Seltzer, et al., Pain, 43 (1990) 205–218 (Title: A novel behavioral model of neuropathic pain disorders produced in rats by partial sciatic nerve injury).

The compounds of formula (I) may also be used in combination with a COX-2 inhibitor, nonsteroidal anti-inflammatory drug (NSAID), opioid analgesic such as morphine, gabapentinoid, serotonin-norepinephirine reuptake inhibitor (SNRI), ketamine, NMDA receptor antagonist or the like.

The compounds of Formula (I) of this invention can be administered by conventional pharmaceutical practice via either the oral, parenteral or topical routes to mammals, for the treatment of the indicated diseases. For administration to human patient by either route, the dosage is in the range of about 0.01 mg/kg to about 3000 mg/kg body weight of the patient per day, preferably about 0.01 mg/kg to about 1000 mg/kg body weight per day administered singly or as a divided dose. However, variations will necessarily occur depending upon the weight and condition of the subject being treated, compound employed, the disease state being treated and the particular route of administration chosen.

The compounds of the present invention may be administered alone or in combination with pharmaceutically acceptable carriers by either of the above routes previously indicated, and such administration can be carried out in single or multiple doses. Generally, the compounds can be combined with various pharmaceutically acceptable carriers in the form of tablets, powders, capsules, lozenges, trochees, hard candies, powders, sprays, creams, salves, suppositories, jellies, gels, pastes, lotions, ointments, suspensions, solutions, elixirs, syrups or the like. Such pharmaceutical carriers include solvents, excipients, coating agents, bases, binders, lubricants, disintegrants, solubilizing agents, suspending agents, emulsifing agents, stabilizers, buffering agents, tonicity agents, preservatives, flavorating agents, aromatics, coloring agents and the like.

For example, the tablets can contain various excipients such as starch, lactose, glucose, microcrystalline cellulose, calcium sulfate, calcium carbonate, talc, titanium oxide and the like, coating agents such as gelatin, hydroxypropylcellulose and the like, binding agents such as gelatin, gum arabic, methylcellulose and the like, and the disintegrating agents such as starch, agar, gelatine, sodium hydrogencarbonate and the like. Additionally, lubricating agents such as magnesium stearate and talc are often very useful for tabletting purposes. Solid compositions of a similar type may also be employed as fillers in gelatine capsules; preferred materials in this connection also include lactose as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with diluents such as water, ethanol, propylene glycol, glycerin and various like combinations thereof.

In general, the therapeutically-effective compounds of this invention are present in such oral dosage forms at concentration levels ranging 5% to 70% by weight, preferably 10% to 50% by weight.

The compounds of the present invention in the form of a solution may be injected parenterlly such as intradermaly, subcutaneously, intravenously or intramuscularly. For example the solutions are sterile aqueous solutions, aqueous suspensions and an edible oil solutions. The aqueous solutions may be suitably buffered (preferably pH>8), and may contain enough salts or glucose to make the solution isotonic with blood. The aqueous solutions are suitable for intravenous injection purposes. The aqueous suspensions may contain a suitable dispersing or suspending agents such as sodium carboxymethylcellulose, methylcellulose, polyvinylpyrrolidone or gelatin. The aqueous suspensions can be used for subcutaneous or intramuscular injections. The edible oil such as cottonseed oil, sesame oil, coconut oil or peanut oil can be employed for the edible oil solutions. The oil solutions are suitable for intra-articular, intra-muscular and subcutaneous injection. The preparation of all these solutions under sterile conditions is readily accomplished by standard pharmaceutical techniques well-known to those skilled in the art.

It is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES AND PREPARATIONS

The present invention is illustrated by the following examples and preparation. However, it should be understood that the invention is not limited to the specific details of these examples and preparations. Melting points were taken with a Buchi micro melting point apparatus and is not corrected. Infrared Ray absorption spectra (IR) were measured by a Shimadzu infrared spectrometer (IR-470). $^1$H and $^{13}$C nuclear magnetic resonance spectra (NMR) were measured in $CDCl_3$ by a JEOL NMR spectrometer (JNM-GX270, 270 MHz or JNM-LA300, 300 MHz) unless otherwise indicated and peak positions are expressed in parts per million (ppm) downfield from tetramethylsilane. The peak shapes are denoted as follows: s, singlet; d, doublet; t, triplet; m, multiplet; br, broad.

Analytical data of compounds, which can be prepared according to General Procedures A and B or were prepared in Examples hereinafter disclosed, can be taken by utilizing Waters LC-MS system (LC as 2690, ZMD as MS).

Analytical condition for LC-MS: Column YMC CombiScreen basic 4.6 mm×50 mm, Flow rate 1 mL/min.; Mobile phase 20% MeOH/80% 0.1%$HCO_2H$ in $H_2O$ programmed over 5 min to 90% MeOH/10% 0.1%$HCO_2H$ in $H_2O$. Hold for 5 min.; Wave length 220–400 nm. MS detector ApcI Cone 30 Volts.

Preparation 1

Ethyl (1-Methyl-2-oxo-1,2,3,4-tetrahydro-3-quinolinyl) carboxylate

To a stirred solution of 1-methyl-2-oxo-1,2,3,4-tetrahydro-3-quinoline (this was prepared from 3,4-dihydro-2(1H)-quinolinone by N-methylation, 1.50 g, 9.31 mmol) and ethyl cyanoformate (1.38 g, 13.97 mmol) in THF (40 ml) was added lithium diisopropylamide (2 M solution, 10.2 ml, 20.48 mmol) at −78° C.. After 4 h stirring at −78° C. to −40° C., lithium diisopropylamide (2 M solution, 15 ml, 30 mmol) was added to the reaction mixture at −78° C.. After 17 h stirring at −78° C. to room temperature, the reaction mixture was quenched with water (30 ml) and extracted with ether (50 ml×3). The extracts combined were washed with brine, dried ($Na_2SO_4$), filtered, and concentrated to give 3.22 g of crude product, which was purified by silica gel column chromatography (n-hexane/ethyl acetate: 3/1) to give 930.5 mg (43%) of title compound as yellow oil.

$^1$H NMR (270 MHz, $CDCl_3$) δ 7.32–7.24 (1H, m), 7.19 (1H, br.d, J=7.1 Hz), 7.07–6.97 (2H, m), 4.28–4.07 (2H, m), 3.61 (1H, dd, J=5.8, 9.4 Hz), 3.39 (3H, s), 3.32 (1H, dd, J=9.4, 15.7 Hz), 3.07 (1H, dd, J=5.9, 15.6 Hz), 1.21 (3H, t, J=7.1 Hz). MS(EI direct) m/z: 233(M)$^+$.

Preparation 2

3-Hydroxymethyl-1-methyl-2-oxo-1,2,3,4-tetrahydroquinoline

To a stirred solution of ethyl (1-methyl-2-oxo-1,2,3,4-tetrahydro-3-quinolinyl)carboxylate (490.8 mg, 2.1 mmol) in THF (10 ml) was added lithium borohydride (68.6 mg, 3.15 mmol) at −40° C. and the stirring was continued for 2.5 h at −40° C. to −15° C.. The reaction mixture was quenched with ethyl acetate (5 ml) and water (15 ml) and extracted with ethyl acetate (30 ml×1). Aqueous layer was acidified with 2N HCl to pH 3 and extracted with ethyl acetate (20 ml×2). The extracts combined were dried (Na2SO4), filtered, and concentrated to give 478.4 mg of oil. This was purified by preparative TLC (1 mm thick silica gel plate: n-hexane/ethyl acetate:1/1) to afford 66.6 mg (17%) of title compound as an oil.

$^1$H NMR (270 MHz, $CDCl_3$) δ 7.27 (1H, br.dd, J=7.4, 8.2 Hz), 7.18 (1H, br.d, J=7.4 Hz), 3.89 (2H, d, J=5.4 Hz), 3.37 (3H, s), 2.94–2.63 (3H, m). MS(EI direct) m/z: 191(M)$^+$.

Preparation 3

3-Hydroxymethyl-1-methyl-1,2,3,4-tetrahydroquinoline

To a stirred solution of ethyl (1-methyl-2-oxo-1,2,3,4-tetrahydro-3-quinolinyl)carboxylate (601.3 mg, 2.58 mmol) in THF (10 ml) was added lithium borohydride (84.3 mg, 3.87 mmol) at 0° C. and the stirring was continued for 2.5 h at 0 ° C. To a stirred reaction mixture was added lithium borohydride (40 mg) and the reaction mixture was stirred for 14 h at 0° C. to room temperature. The reaction mixture was quenched with ethyl acetate (5 ml) and water (15 ml) at 0° C. and extracted with ethyl acetate (20 ml×3). The extracts combined were dried ($Na_2SO_4$), filtered, and concentrated to give 500.1 mg of oil. This was purified by preparative TLC (1 mm thick silica gel plate: n-hexane/ethyl acetate:3/2, 2 developed) to afford 211 mg (46%) of title compound as an oil.

$^1$H NMR (270 MHz, $CDCl_3$) δ 7.12–7.06 (1H, m), 7.00–6.93 (1H, m), 6.66–6.58 (2H, m), 3.67 (1H, dd, J=5.9, 10.6 Hz), 3.58 (1H, dd, J=7.4, 10.6 Hz), 3.31 (1H, ddd, J=1.5, 4.0, 11.2 Hz), 3.02 (1H, dd, J=8.2, 11.2 Hz), 2.89 (3H, s), 2.89–2.79 (1H, m), 2.54 (1H, dd, J=8.9, 15.8 Hz), 2.32–2.15 (1H, m), 1.73 (1H, br.s). MS (ESI positive) m/z: 178 (M+H)$^+$.

Example 1

2,3-Dihydro-1'-[(1-methyl-2-oxo-1,2,3,4-tetrahydro-3-quinolinyl)methyl]spiro[1H-indene-1,4'-piperidine]

To a stirred solution of 3-hydroxymethyl-1-methyl-2-oxo-1,2,3,4-tetrahydroquinoline (86.4 mg, 0.452 mmol) and triethylamine (0.11 ml, 0.814 mmol) in CH$_2$Cl$_2$ (4.5 ml) was added methanesulfonyl chloride (0.04 ml, 0.542 mmol) at 0° C. and the resulting reaction mixture was stirred for 10 min. The reaction mixture was quenched with saturated aqueous NaHCO$_3$ solution and extracted with ethyl acetate (20 ml×3). The extracts combined were washed with brine, dried (Na$_2$SO$_4$), filtered, and concentrated to give 121.9 mg of crude mesylate. A mixture of this mesylate (121.9 mg, 0.452 mmol), 2,3-dihydrospiro[1H-indene-1,4'-piperidine] hydrochloride (67.3 mg, 0.301 mmol) and N,N-diisopropylethylamine (0.16 ml, 0.903 mmol) in ethyleneglycol (6 ml) was stirred at 80° C. for 19 h. The reaction mixture was quenched with saturated aqueous NaHCO$_3$ solution (5 ml) and extracted with ethyl acetate (20 ml×3). The extracts combined were washed with brine, dried (Na$_2$SO$_4$), filtered, and concentrated to give 115 mg of crude oil. This oil was purified by preparative TLC (1 mm thick silica gel plate: CH2Cl2/methanol:20/1) to afford 38.4 mg (36%) of title compound as an yellow oil.

$^1$H NMR (270 MHz, CDCl$_3$) δ 7.30–7.11 (6H, m), 7.03 (1H, ddd, J=1, 7.4, 7.4 Hz), 6.98 (1H, d, J=8.1 Hz), 3.36 (3H, s), 3.17–3.07 (1H, m), 2.92–2.70 (6H, m), 2.60–2.46 (1H, m), 2.43–2.30 (1H, m), 2.22–2.08 (1H, m), 2.06–1.82 (5H, m), 1.58–1.46 (2H, m).

This oil (35.6 mg, 0.099 mmol) and citric acid (19 mg, 0.099 mmol) was dissolved in mixed solvent (1.5 ml of methanol and 0.2 ml of CH$_2$Cl$_2$), and the solution was stirred at room temperature for 0.5 h. The solvent was evaporated and resulting residue was solidified from CH$_2$Cl$_2$ (0.5 ml)/n-hexane (5 ml) and collected by filtration to give 45.4 mg of citrate salt as white amorphous solid.

MS(EI direct) m/z: 360(M)$^+$.

IR(KBr): 2937, 1732, 1660, 1602, 1475, 1380, 1193, 758 cm$^{-1}$

Anal. Calcd for C$_{24}$H$_{28}$N$_2$O—C$_6$H$_8$O$_7$-1.5H$_2$O: C, 62.16; H, 6.78; N, 4.83. Found: C, 62.05; H, 6.70; N, 4.50.

This compound was prepared by N-methylation of 2,3-dihydro-1'-[(2-oxo-1,2,3,4-tetrahydro-3-quinolinyl)methyl]spiro[1H-indene-1,4'-piperidine] described in Example 7.

To a stirred suspension of NaH (60% oil suspension, 14.1 mg, 0.352 mmol, oil was removed by n-hexane washing and decantation) in DMF (1 ml) was added dropwise a solution of 2,3-dihydro-1'-[(2-oxo-1,2,3,4-tetrahydro-3-quinolinyl)methyl]spiro[1H-indene-1,4'-piperidine] (111 mg, 0.32 mmol) in DMF (4 ml) at 0° C. After 0.5 h stirring at room temperature, methyl iodide (0.04 ml, 0.64 mmol) was added to the reaction mixture at 0° C. After 0.5 h stirring, the reaction mixture was quenched with water (15 ml) and extracted with CH$_2$Cl$_2$ (20 ml×3). The extracts combined were dried (Na$_2$SO$_4$), filtered, and concentrated. The residue was dissolved in ethyl acetate (40 ml), washed with water (30 ml) and brine, dried (Na$_2$SO$_4$), filtered, and concentrated to give 126.7 mg of crude oil. This oil was purified by preparative TLC (1 mm thick silica gel plate: CH$_2$Cl$_2$/methanol:20/1) to afford 86.7 mg (75%) of title compound as an yellow oil.

Example 2

2,3-Dihydro-1'-[(1-methyl-1,2,3,4-tetrahydro-3-quinolinyl)methyl]spiro[1H-indene-1,4'-piperidine]

To a stirred solution of 3-hydroxymethyl-1-methyl-1,2,3,4-tetrahydroquinoline (100.3 mg, 0.566 mmol) and triethylamine (0.14 ml, 1.019 mmol) in CH$_2$Cl$_2$ (5 ml) was added methanesulfonyl chloride (0.053 ml, 0.679 mmol) at 0° C. and the resulting reaction mixture was stirred for 10 min. The reaction mixture was quenched with saturated aqueous NaHCO$_3$ solution and extracted with CH$_2$Cl$_2$ (15 ml×3). The extracts combined were washed with brine, dried (Na$_2$SO$_4$), filtered, and concentrated to give 149.59 mg of crude mesylate. A mixture of this mesylate (149.5 mg, 0.566 mmol), 2,3-dihydrospiro[1H-indene-1,4'-piperidine]hydrochloride (84.3 mg, 0.377 mmol) and N,N-diisopropylethylamine (0.20 ml, 1.131 mmol) in ethyleneglycol (7.5 ml) was stirred at 80° C. for 21 h. The reaction mixture was quenched with saturated aqueous NaHCO$_3$ solution (10 ml) and extracted with ethyl acetate (20 ml×3). The extracts combined were dried (Na$_2$SO$_4$), filtered, and concentrated. The residue was purified by preparative TLC (1 mm thick silica gel plate:n-hexane/ethyl acetate:1/1, then n-hexane/ethyl acetate:5/1, 3 times developed) to afford 97.3 mg (75%) of title compound as an yellow oil.

$^1$H NMR (270 MHz, CDCl$_3$) δ 7.26–6.96 (6H, m), 6.65–6.56 (2H, m), 3.38–3.28 (1H, m), 3.00–2.79 (9H, m, including 3H, s at 2.91 ppm), 2.60–2.45 (1H, m), 2.36–1.85 (9H, m), 1.59–1.49 (2H, m).

This was converted to citric acid salt similar to that described in Example 1 to afford 112.3 mg of citric acid salt as pink color solid.

MS(EI direct) m/z: 346(M)$^+$.

IR(KBr): 2937, 1724, 1602, 1504, 1436, 1218, 756 cm$^{-1}$

Anal. Calcd for C$_{24}$H$_{30}$N$_2$—C$_6$H$_8$O$_7$—H$_2$O: C, 64.73; H, 7.24; N, 5.03. Found: C, 64.67; H, 7.21; N, 4.66.

Example 3

2,3-Dihydro-1'-[(5-oxo-2,3-dihydro-1H,5H-pyrido[3,2,1-ij]quinolin-6-yl)methyl]spiro[1H-indene-1,4'-piperidine]

To a stirred solution of 5-oxo-2,3-dihydro-6-hydroxymethyl-1H,5H-pyrido[3,2,1-ij]quinoline (30 mg, 0.139 mmol) and triethylamine (0.035 ml, 0.25 mmol) in CH$_2$Cl$_2$ (1.5 ml) was added methanesulfonyl chloride (0.013 ml, 0.167 mmol) at 0° C. and the resulting reaction mixture was stirred for 30 min. The reaction mixture was quenched with saturated aqueous NaHCO$_3$ solution and extracted with CH$_2$Cl$_2$ (15 ml×3). The extracts combined were washed with brine, dried (Na$_2$SO$_4$), filtered, and concentrated to give 41.3 mg of crude mesylate. A mixture of this mesylate (41.3 mg, 0.139 mmol), 2,3-dihydrospiro[1H-indene-1,4'-piperidine] hydrochloride (26 mg, 0.116 mmol) and N,N-diisopropylethylamine (0.061 ml, 0.348 mmol) in THF (3 ml) was stirred with reflux for 1 day. Then 0.02 ml of N,N-diisopropylethylamine was added to the reaction mixture and refluxed for 15 h. The reaction mixture was quenched with saturated aqueous NaHCO$_3$ solution (15 ml) and extracted with ethyl acetate (20 ml×3). The extracts combined were dried (Na$_2$SO$_4$), filtered, and concentrated. The residue was purified by preparative TLC (1 mm thick silica gel plate: n-hexane/ethyl acetate:3/1, 3 times developed) to afford 20.5 mg (46%) of title compound as an yellow oil.

$^1$H NMR (270 MHz, CDCl$_3$) δ 7.85 (1H, br.s), 7.49–7.43 (1H, m), 7.31–7.10 (6H, m), 4.23 (2H, dd, J=5.6, 5.9 Hz), 3.65 (2H, br.s), 3.04–2.94 (2H, m), 2.91 (4H, t, J=7.4 Hz), 2.46–2.32 (2H, m), 2.18–1.98 (6H, m), 1.62–1.52 (2H, m).

This oil (12.3 mg) was converted to citric acid salt similar to that described in Example 1 to afford 11.6 mg of citric acid salt as white solid.

MS (ESI positive) m/z: 385 (M+H)$^+$.

IR(KBr): 2937, 1724, 1643, 1589, 765 cm$^{-1}$

Anal. Calcd for C$_{26}$H$_{28}$N$_2$O—C$_6$H$_8$O$_7$-1.4H$_2$O: C, 63.86; H, 6.50; N, 4.65. Found: C, 63.97; H, 6.34; N, 4.36.

Preparation 4
5-Formyl-4-oxo-1,2-dihydro-4H-pyrrolo[3,2,1-ij]quinoline

A mixture of 4-oxo-1,2-dihydro-4H-pyrrolo[3,2,1-ij]quinoline (201.6 mg, 0.937 mmol), thionyl chloride (0.5 ml), methanol (20 ml), and 2 drops of DMF was refluxed for 5.5 h. After evaporation of the solvent, the residue was basified with saturated aqueous $NaHCO_3$ solution, and extracted with ethyl acetate (20 ml×3). The extracts combined were dried ($Na_2SO_4$), filtered, and concentrated. The residue was purified by preparative TLC (1 mm thick silica gel plate: n-hexane/acetone:1/2) to afford 183.2 mg (74%) of methyl ester as an yellow solid. To a stirred solution of this ester (30 mg, 0.131 mmol) in THF (1.5 ml) was added diisobutylaluminum hydride (0.26 ml, 0.262 mmol) at −78° C. After 15 min stirring, 0.13 ml of diisobutylaluminum hydride was added to the reaction mixture and stirring was continued another 15 min. The reaction mixture was quenched with saturated aqueous $NH_4Cl$ solution (5 ml) and extracted with ethyl acetate (20 ml×3). The extracts combined were dried ($Na_2SO_4$), filtered, and concentrated. The residue was purified by preparative TLC (1 mm thick silica gel plate:n-hexane/ethyl acetate:1/1) to afford 5.6 mg (21%) of title compound as an yellow solid.

$^1$H NMR (270 MHz, $CDCl_3$) δ 10.50 (1H, s), 8.43 (1H, s), 7.55 (1H, dd, J=1.0, 8.1 Hz), 7.46 (1H, dd, J=1.0, 7.3 Hz), 7.21 (1H, dd, J=7.4, 7.9 Hz), 4.51 (2H, dd, J=7.8, 8.2 Hz), 3.48 (2H, br.t, J=7.9 Hz).

Example 4
2,3-Dihydro-1'-[(4-oxo-1,2-dihydro-4H-pyrrolo[3,2,1-ij]quinolin-5-yl)methyl]spiro[1H-indene-1,4'-piperidine]

To a stirred solution of 5-formyl-4-oxo-1,2-dihydro-4H-pyrrolo[3,2,1-ij]quinoline (11.5 mg, 0.058 mmol) and 2,3-dihydrospiro[1H-indene-1,4'-piperidine] hydrochloride (13 mg, 0.058 mmol) in $CH_2Cl_2$ (3.7 ml) was added sodium triacetoxyborohydride (22 mg, 0.104 mmol) at 0° C. and resulting mixture was stirred at room temperature for 15 h. The reaction mixture was quenched with saturated aqueous $NaHCO_3$ solution (5 ml) and extracted with ethyl acetate (15 ml×3). The extracts combined were dried ($Na_2SO_4$), filtered, and concentrated. The residue was purified by preparative TLC (1 mm thick silica gel plate: $CH_2Cl_2$/methanol:20/1, then ethyl acetate/isopropanol/25%$NH_4OH$:80/5/1) to afford 4.2 mg (13%) of title compound as colorless oil.

$^1$H NMR (270 MHz, $CDCl_3$) δ 7.88 (1H, s), 7.44–7.40 (1H, m), 7.33–7.12 (6H, m), 4.48 (2H, dd, J=7.3, 7.4 Hz), 3.66 (2H, s), 3.50–3.40 (2H, m), 3.02–2.92 (2H, m),2.90 (2H, t, J=6.4 Hz), 2.44–2.32 (2H, m), 2.10–1.96 (4H, m), 1.62–1.53 (2H, m).

This oil (4.2 mg) was converted to citric acid salt similar to that described in Example 1 to afford 2.6 mg of citric acid salt as white solid.

MS (ESI positive) m/z: 371 (M+H)$^+$.

Preparation 5
5-Hydroxymethyl-4-oxo-1,2,5,6-tetrahydro-4H-pyrrolo[3,2,1-ij]quinoline To a stirred solution of 4-oxo-1,2,5,6-tetrahydro-4H-pyrrolo[3,2,1-ij]quinoline (700 mg, 4.04 mmol) and ethyl cyanoformate (0.72 ml, 7.274 mmol) in THF (20 ml) was added a solution of lithium diisopropylamide (this was prepared from 1.4 ml of diisopropylamine and 6.4 ml of 1.59 M solution of n-butyllithium in hexane) in THF (20 ml) at −78° C. After 3 h stirring at −78° C. to −50° C., the reaction mixture was quenched with water (100 ml) and extracted with ethyl acetate (40 ml×3). The extracts combined were dried ($Na_2SO_4$), filtered, and concentrated to give 1.36 g of crude product, which was purified by silica gel column chromatography (n-hexane/ethyl acetate: 3/2) to give 666.6 mg (67%) of ethyl ester derivative as yellow white solid.

$^1$H NMR (300 MHz, $CDCl_3$) δ 7.09 (1H, br.d, J=7.3 Hz), 7.01 (1H, br.d, J=7.1 Hz), 6.94 (1H, dd, J=7.1, 7.5 Hz), 4.29–4.13 (2H, m), 4.11 (2H, dd, J=8.2, 8.4 Hz), 3.66 (1H, dd, J=7.7, 8.3 Hz), 3.37 (1H, dd, J=8.4, 16.3 Hz), 3.20 (2H, dd, J=7.7, 9.2 Hz), 3.07 (1H, dd, J=7.3, 16.5 Hz), 1.26 (3H, t, J=7.1 Hz).

To a stirred solution of the above ester (227.4 mg, 0.927 mmol) in ethanol (10 ml) was added sodium borohydride (105.2 mg, 2.78 mmol) at 0° C. After 1 day stirring at 0° C., 70 mg of sodium borohydride was added to the reaction mixture. After 7 h stirring, 70 mg of sodium borohydride and ethanol (1 ml) was added to the reaction mixture at 0° C. After 17 h stirring, 70 mg of sodium borohydride and ethanol (1 ml) was added to the reaction mixture at 0° C. After 6.5 h stirring at 0° C. to room temperature, the reaction mixture was quenched with saturated aqueous $NaHCO_3$ solution (40 ml) and extracted with $CH_2Cl_2$ (30 ml×3). The extracts combined were dried ($Na_2SO_4$), filtered, and concentrated. The residue was purified by preparative TLC (1 mm thick silica gel plate: n-hexane/ethyl acetate:1/3) to afford 90.5 mg (48%) of title compound as an oil.

$^1$H NMR (270 MHz, $CDCl_3$) δ 7.08 (1H, br.d, J=7.2 Hz), 7.00 (1H, br.d, J=6.9 Hz), 6.94 (1H, dd, J=7.3, 7.4 Hz), 4.15 (1H, ddd, J=5.6, 9.9, 12.0 Hz), 4.06–3.94 (1H, m), 3.93–3.83 (2H, m), 3.67 (1H, br.s), 3.33–3.09 (2H, m), 2.94–2.81 (3H, m).

MS(EI direct) m/z: 203(M)$^+$.

Example 5
2,3-Dihydro-1'-[(4-oxo-1,2,5,6-tetrahydro-4H-pyrrolo[3,2,1-ij]quinoline-5-yl)methyl]spiro[1H-indene-1,4'-piperidine]

To a stirred solution of 4-oxo-5-hydroxymethyl-1,2,5,6-tetrahydro-4H-pyrrolo[3,2,1-ij]quinoline (59.8 mg, 0.294 mmol) and triethylamine (0.074 ml, 0.529 mmol) in $CH_2Cl_2$ (3 ml) was added methanesulfonyl chloride (0.027 ml, 0.353 mmol) at 0° C. and the resulting reaction mixture was stirred for 10 min. The reaction mixture was quenched with saturated aqueous $NaHCO_3$ solution and extracted with $CH_2Cl_2$ (15 ml×3). The extracts combined were washed with brine, dried ($Na_2SO_4$), filtered, and concentrated to give 84.6 mg of crude mesylate as yellow amorphous solid. A mixture of this mesylate (84.6 mg, 0.294 mmol), 2,3-dihydrospiro[1H-indene-1,4'-piperidine]hydrochloride (59.7 mg, 0.267 mmol) and N,N-diisopropylethylamine (0.014 ml, 0.801 mmol) in THF (6.5 ml) was stirred with reflux for 1 day. The reaction mixture was quenched with saturated aqueous $NaHCO_3$ solution (20 ml) and extracted with ethyl acetate (15 ml×3). The extracts combined were dried ($Na_2SO_4$), filtered, and concentrated. The residue was purified by preparative TLC (1 mm thick silica gel plate: $CH_2Cl_2$/methanol:20/1, then ethyl acetate/isopropanol/25%NH4OH: 80/5/1) to afford 29.3 mg (30%) of title compound as colorless oil.

$^1$H NMR (270 MHz, $CDCl_3$) δ 7.23–7.11 (4H, m), 7.10–7.02 (2H, m), 6.93 (1H, dd, J=7.4, 7.4 Hz), 4.17–3.99 (2H, m), 3.25–2.53 (11 H, m), 2.36 (1H, ddd, J=2.3, 11.9, 12.2 Hz), 2.17 (1H, ddd, J=2.3, 11.9, 12.2 Hz), 2.00 (2H, t, J=7.4 Hz), 1.99–1.81 (2H, m), 1.58–1.46 (2H, m).

This oil (29.3 mg) was converted to citric acid salt similar to that described in Example 1 to afford 34.6 mg of citric acid salt as white solid.

MS (ESI positive) m/z: 373 (M+H)+.
IR(KBr): 2929, 1728, 1652, 1595, 1485, 1409, 1203, 763 cm$^{-1}$
Anal. Calcd for $C_{25}H_{28}N_2O$—$C_6H_8O_7$-1.5$H_2O$: C, 62.93; H, 6.64; N, 4.73. Found: C, 62.86; H, 6.43; N, 4.46.

Preparation 6
2,3-Dihydro-1'-[(2-oxo-1,2-dihydro-3-quinolinyl)methyl]spiro[1H-indene-1,4'-piperidine]

To a stirred suspension of 3-formyl-2-hydroxyquinoline (0.18 g, 1.04 mmol, this was prepared according to known procedure: M. Fernandez, E.de la Cuesta, C. Avendano, *Synthesis* 1995, 1362), 2,3-dihydrospiro[1H-indene-1,4'-piperidine] hydrochloride (0.23 g, 1.04 mmol) and acetic acid (0.18 ml, 3.12 mmol) was added sodium triacetoxyborohydride (0.49 g, 2.29 mmol) at room temperature. After 18 h stirring, the reaction mixture was quenched with saturated aqueous $NaHCO_3$ solution and extracted with $CH_2Cl_2$. The extracts combined were dried ($Na_2SO_4$), filtered, and concentrated. The residue was purified by column chromatography (silica gel, $CH_2Cl_2$/methanol:20/1) to afford 154 mg (43%) of title compound as colorless oil.
$^1$H NMR (300 MHz, $CDCl_3$) δ 12.26 (1H, br.s), 7.97 (1H, s), 7.64–7.41 (3H, m), 7.3–7.13 (5H, m), 3.71 (2H, s), 3.06–2.97 (2H, m), 2.91 (2H, dd, J=7.1, 7.4 Hz), 2.48–2.36 (2H, m), 2.11–1.99 (4H, m), 1.63–1.54 (2H, m).

Example 6
2,3-Dihydro-1'-[(1-methyl-2-oxo-1,2-dihydro-3-quinolinyl)methyl]spiro[1H-indene-1,4'-piperidine]

To a stirred solution of 2,3-dihydro-1'-[(2-oxo-1,2-dihydro-3-quinolinyl)methyl]spiro[1H-indene-1,4'-piperidine] (150 mg, 0.44 mmol) in DMF (4 ml) was added sodium hydride (60% oil suspension, 23 mg, 0.57 mmol) and iodomethane (0.036 ml, 0.57 mmol) at room temperature. After 1 h stirring, the reaction mixture was quenched with saturated aqueous $NaHCO_3$ solution and extracted with ethyl acetate. The extracts combined were washed with water, dried ($Na_2SO_4$), filtered, and concentrated. The residue was purified by preparative TLC (1 mm thick silica gel plate: $CH_2Cl_2$/methanol:10/1) to afford 127 mg (80%) of title compound as pale yellow amorphous solid. 100 mg of this was purified again by preparative TLC (1 mm thick silica gel plate: $CH_2Cl_2$/methanol:10/1) to afford 82 mg of title compound as pale yellow oil.
$^1$H NMR (300 MHz, $CDCl_3$) δ 7.87 (1H, s), 7.62 (1H, dd, J=1.5, 7.7 Hz), 7.55 (1H, ddd, J=1.5, 7.1, 7.3 Hz), 7.36 (1H, d, J=8.4 Hz), 7.28–7.13 (5H, m), 3.76 (3H, s), 3.65 (2H, br.d, J=1.1 Hz), 3.02–2.96 (2H, m), 2.90 (2H, dd, J=7.3, 7.3 Hz), 2.38 (2H, ddd, J=2.2, 11.9, 12.5 Hz), 2.10–1.98 (4H, m), 1.62–1.53 (2H, m).
This oil (82 mg) was converted to citric acid salt similar to that described in Example 1 to afford 91 mg of citric acid salt as white solid.
MS (ESI positive) m/z: 359 (M+H)+.
IR(KBr): 3421, 2943, 1718, 1647, 1577, 1458, 1224, 1193, 759 cm$^{-1}$
Anal. Calcd for $C_{24}H_{26}N_2O$—$C_6H_8O_7$-1.5$H_2O$: C, 62.38; H, 6.46; N, 4.85. Found: C, 62.54; H, 6.32; N, 4.67.

Preparation 7
2,3-Dihydro-1'-[2-ethoxycarbonyl-3-(2-nitrophenyl)propyl]spiro[1H-indene-1,4'-piperidine]

To a stirred solution of lithium bis(trimethylsilyl)amide (1M solution in THF, 12 ml, 12 mmol) was added dropwise a solution of 2,3-dihydro-1'-[2-(ethoxycarbonyl)ethyl]spiro[1H-indene-1,4'-piperidine] (1356.1 mg, 4.72 mmol, this was prepared from 2,3-dihydrospiro[1H-indene-1,4'-piperidine] and ethyl 3-bromopropionate) in THF (60 ml) at −78° C. To this solution was added dropwise a solution of 2-nitrobenzyl bromide (1529.5 mg, 7.08 mmol) and the resulting reaction mixture was stirred at −78° C. to −40° C. for 6.5 h. The reaction mixture was quenched with 10% HCl solution (30 ml) and extracted with ethyl acetate (50 ml×3). The extracts combined were washed with water (150 ml) and brine (50 ml), dried ($Na_2SO_4$), filtered, and concentrated to give 2.46 g of crude product, which was purified by column chromatography (silica gel, $CH_2Cl_2$/methanol: 20/1, then 40/1) to give 1.018 g (51%) of title compound as brown oil.
$^1$H NMR (270 MHz, $CDCl_3$) δ 7.99–7.94 (1H, m), 7.54–7.47 (1H, m), 7.41–7.34 (2H, m), 7.24–7.10 (4H, m), 4.13–3.98 (2H, m), 3.43–3.35 (1H, m), 3.13–2.98(2H, m), 2.92–2.70 (6H, m), 2.60–2.52 (1H, m), 2.29–2.13 (2H, m), 1.98 (2H, t, J=7.2 Hz), 1.92–1.77 (2H, m), 1.54–1.44 (2H, m), 1.14 (3H, t, J=7.1 Hz).
MS (ESI positive) m/z: 423 (M+H)+.

Example 7
2,3-Dihydro-1'-[(2-oxo-1,2,3,4-tetrahydro-3-quinolinyl)methyl]spiro[1H-indene-1,4'-piperidine]

A mixture of 2,3-dihydro-1'-[2-ethoxycarbonyl-3-(2-nitrophenyl)propyl]spiro[1 H-indene-1,4'-piperidine] (800 mg, 1.89 mmol) and 10% palladium on carbon (80 mg) in methanol (120 ml) was stirred under hydrogen atmosphere at room temperature for 4.5 h. After Celite filtration, the filtrate was concentrated to give 610 mg of crude product, which was purified by column chromatography (silica gel, $CH_2Cl_2$/methanol: 20/1) to give 448.1 mg (68%) of title compound as pale yellow solid.
$^1$H NMR (270 MHz, $CDCl_3$) δ 8.18 (1H, br.s), 7.25–7.10 (6H, m), 7.00 (1H, br.dd, J=7.4, 7.4 Hz), 6.77 (1H, br.d, J=7.4 Hz), 3.22–2.98 (1H, m), 3.02–2.72 (8H, m), 2.65–2.50 (1H, m), 2.42–2.28 (1H, m), 2.22–2.10 (1H, m), 2.05–1.82 (4H, m), 1.59–1.46 (2H, m).
This solid (24.5 mg) was converted to citric acid salt similar to that described in Example 1 to afford 25.8 mg of citric acid salt as white solid.
MS (ESI positive) m/z: 347 (M+H)+.
IR(KBr): 3400, 3250, 2935, 1678, 1595, 1498, 1394, 1242, 759 cm$^{-1}$
Anal. Calcd for $C_{23}H_{26}N_2O$—$C_6H_8O_7$-1.5$H_2O$: C, 61.58; H, 6.59; N, 4.95. Found: C, 61.52; H, 6.36; N, 4.87.

Preparation 8
2,3-Dihydro-1'-{[1-(3-t-butyldimethylsilyloxypropyl)-2-oxo-1,2,3,4-tetrahydro-3-quinolinyl]methyl}spiro[1H-indene-1,4'-piperidine]

To a stirred suspension of NaH (60% oil suspension, 13.8 mg, 0.347 mmol, oil was removed by n-hexane washing and decantation) in DMF (1 ml) was added dropwise a solution of 2,3-dihydro-1'-[(2-oxo-1,2,3,4-tetrahydro-3-quinolinyl)methyl]spiro[1H-indene-1,4'-piperidine] (100 mg, 0.289 mmol) in DMF (4 ml) at 0° C. After 0.5 h stirring at room temperature, a solution of (3-bromopropoxy)-t-butyldimethylsilane (146.4 mg, 0.578 mmol) in DMF (2 ml) was added to the reaction mixture at 0° C. After 2 h stirring, the reaction mixture was quenched with water (20 ml) and extracted with $CH_2Cl_2$ (15 ml×3). The extracts combined were dried ($Na_2SO_4$), filtered, and concentrated. The residue was dissolved in ethyl acetate (40 ml), washed with water (20 ml) and brine, dried ($Na_2SO_4$), filtered, and concentrated to give 216.2 mg of crude oil. This oil was purified by preparative TLC (1 mm thick silica gel plate: n-hexane/ acetone:4/1) to afford 138.2 mg (92%) of title compound as pale yellow oil.

$^1$H NMR (300 MHz, CDCl$_3$) δ 7.25–7.11 (7H, m), 7.02–6.97 (1H, m), 4.07–3.92 (2H, m), 3.77–3.59 (2H, m), 3.11–2.97 (1H, m), 2.86–2.65 (7H, m), 2.50–2.40 (1H, m), 2.36–2.22 (1H, m), 2.20–2.00 (1H, m), 1.98–1.76 (6H, m), 1.51–1.41 (2H, m), 0.93 (9H, s), 0.07 (3H, s), 0.07 (3H, s).

MS(EI direct) m/z: 518 (M)$^+$.

Example 8
2,3-Dihydro-1'-{[1-(3-hydroxypropyl)-2-oxo-1,2,3,4-tetrahydro-3-quinolinyl]methyl}spiro[1H-indene-1,4'-piperidine]

To a stirred solution of 2,3-dihydro-1'-{[1-(3-t-butyldimethylsilyloxypropyl)-2-oxo-1,2,3,4-tetrahydro-3-quinolinyl]methyl}spiro[1H-indene-1,4'-piperidine] (138.2 mg, 0.266 mmol) in THF (3 ml) was added a solution of tetrabutylammonium fluoride (1M solution in THF, 0.532 ml, 0.532 mmol) at 0° C. After 1 h stirring at room temperature, the reaction mixture was quenched with water (10 ml) and extracted with CH$_2$Cl$_2$ (15 ml×3). The extracts combined were dried (Na$_2$SO$_4$), filtered, and concentrated to give 143.3 mg of crude oil. This oil was purified by preparative TLC (1 mm thick silica gel plate: CH$_2$Cl$_2$/methanol:20/1 2 developed, then n-hexane/acetone/triethylamine:3/1/0.1) to afford 85.3 mg (79%) of title compound as colorless oil.

$^1$H NMR (300 MHz, CDCl$_3$) δ 7.29–7.12 (6H, m), 7.09–7.01 (2H, m), 4.27 (1H, ddd, J=6.4, 6.8, 14.6 Hz), 3.97 (1H, ddd, J=5.5, 5.9, 14.6 Hz), 3.60 (2H, t, J=5.5 Hz), 3.16 (1H, dd, J×4.6, 15.0 Hz), 2.98–2.72 (8H, m), 2.47 (1H, dd, J=8.8, 12.3 Hz), 2.34–2.22 (1H, m), 2.21–2.10 (1H, m), 1.99 (2H, t, J=7.3 Hz), 1.98–1.83 (4H, m), 1.56–1.46 (2H, m).

This solid (85.3 mg) was converted to citric acid salt similar to that described in Example 1 to afford 96.6 mg of citric acid salt as white solid.

MS (ESI positive) m/z: 405 (M+H)$^+$.

IR(KBr): 3373, 2947, 1716, 1652, 1602, 1458, 1396, 1184, 759 cm$^{-1}$

Anal. Calcd for C$_{26}$H$_{32}$N$_2$O$_2$—C$_6$H$_8$O$_7$—H$_2$O: C, 62.53; H, 6.89; N, 4.56. Found: C, 62.36; H, 6.83; N, 4.34.

Preparation 9
2,3-Dihydro-1'-{[1-(methoxycarbonylmethyl)-2-oxo-1,2,3,4-tetrahydro-3-quinolinyl]methyl}spiro[1H-indene-1,4'-piperidine]

To a stirred suspension of NaH (60% oil suspension, 27.7 mg, 0.692 mmol, oil was removed by n-hexane washing and decantation) in DMF (2 ml) was added dropwise a solution of 2,3-dihydro-1'-[(2-oxo-1,2,3,4-tetrahydro-3-quinolinyl)methyl]spiro[1H-indene-1,4'-piperidine] (200 mg, 0.577 mmol) in DMF (5 ml) at 0° C. After 0.5 h stirring at room temperature, a solution of methyl bromoacetate(176.5 mg, 1.154 mmol) in DMF (3 ml) was added to the reaction mixture at 0° C. After 2 h stirring, the reaction mixture was quenched with water (30 ml) and extracted with CH$_2$Cl$_2$ (15 ml×3). The extracts combined were dried (Na$_2$SO$_4$), filtered, and concentrated. The residue was dissolved in ethyl acetate (30 ml), washed with water (20 ml) and brine, dried (Na$_2$SO$_4$), filtered, and concentrated to give 388.7 mg of crude oil. This oil was purified by preparative TLC (1 mm thick silica gel plate: n-hexane/acetone:2/1 and 1/1) to afford 218.7 mg (91%) of title compound as pale yellow oil.

$^1$H NMR (300 MHz, CDCl$_3$) δ 7.28–7.12 (6H, m), 7.04 (1H, ddd, J=0.9, 7.3, 7.5 Hz), 6.74 (1H, br.d, J=7.9 Hz), 4.74 (1H, d, J=17.6 Hz), 4.61 (1H, d, J=17.4 Hz), 3.77 (3H, s), 3.24–3.08 (1H, m), 2.98–2.70 (7H, m), 2.64–2.50 (1H, m), 2.44–2.30 (1H, m), 2.24–2.08 (1H, m), 2.00 (2H, t, J=7.5 Hz), 1.98–1.84 (1H, m), 1.58–1.47 (2H, m).

MS(EI direct) m/z: 418 (M)$^+$.

Preparation 10
2,3-Dihydro-1'-{[1-(carboxymethyl)-2-oxo-1,2,3,4-tetrahydro-3-quinolinyl]methyl}spiro[1H-indene-1,4'-piperidine]

To a stirred solution of 2,3-dihydro-1'-{[1-(methoxycarbonylmethyl)-2-oxo-1,2,3,4-tetrahydro-3-quinolinyl]methyl}spiro[1H-indene-1,4'-piperidine] (218.7 mg, 0.523 mmol) in methanol (2.3 ml) and THF (2.3 ml) was added 2N NaOH (1.1 ml) at room temperature. After 1 h stirring, ethyl acetate (40 ml) was added and washed with 1N HCl (4 ml), dried (Na$_2$SO$_4$), filtered, and concentrated to give 241.2 mg of crude acid. This was used for the next reaction without purification.

$^1$H NMR (300 MHz, CDCl$_3$) δ 11.20 (1H, br.s), 7.32–7.14 (5H, m), 7.12–6.96 (2H, m), 6.71–6.64 (1H, m), 4.76 (1H, d, J=17.8 Hz), 4.44 (1H, d, J=17.8 Hz), 3.65–3.50 (3H, m), 3.50–3.20 (3H, m), 3.10–2.85 (5H, m), 2.75–2.40 (2H, m), 2.10–1.98 (2H, m), 1.70–1.56 (2H, m).

Example 9
2,3-Dihydro-1'-{[1-(2-amino-2-oxoethyl)-2-oxo-1,2,3,4-tetrahydro-3-quinolinyl]methyl}spiro[1H-indene-1,4'-piperidine]

To a stirred solution of 2,3-dihydro-1'-{[1-(carboxymethyl)-2-oxo-1,2,3,4-tetrahydro-3-quinolinyl]methyl}spiro[1H-indene-1,4'-piperidine] (128.8 mg, 0.318 mmol) and 1,1'-carbonyldiimidazole (61.9 mg, 0.382 mmol) in acetonitrile (16 ml) was added triethylamine (0.053 ml) at room temperature. After 2 h stirring at 70° C., 25% NH$_4$OH (4.1 ml) was added to the reaction mixture. After 2 h stirring at 70° C., the reaction mixture was cooled down to room temperature, quenched with saturated aqueous NaHCO$_3$ solution (10 ml), extracted with CH2Cl2 (20 ml×3). The extracts combined were dried (Na$_2$SO$_4$), filtered, and concentrated to give 117.5 mg of crude product. This was purified by preparative TLC (1 mm thick silica gel plate: CH$_2$Cl$_2$/methanol:20/1 2 developed then n-hexane/acetone/triethylamine: 20/10/1) to afford 78.9 mg (62%) of title compound as colorless oil.

$^1$H NMR (300 MHz, CDCl$_3$) δ 7.57 (1H, br.s), 7.30–6.95 (8H, m), 5.51 (1H, br.s), 5.27 (1H, d, J=15.8 Hz), 3.95 (1H, d, J=16.5 Hz), 3.38–3.12 (3H, m), 2.87 (2H, t, J=7.3 Hz), 2.73 (1H, dd, J=3.7, 15.9 Hz), 2.62 (1H, dd, J=9.7, 12.3 Hz), 2.60–2.51 (1H, m), 2.39 (1H, dd, J=7.7, 12.3 Hz), 2.25–1.82 (5H, m), 1.60–1.43 (3H, m).

This solid (78.9 mg) was converted to citric acid salt similar to that described in Example 1 to afford 95.5 mg of citric acid salt as white solid.

MS (ESI positive) m/z: 404 (M+H)$^+$.

IR(KBr): 3336, 2943, 1670, 1604, 1465, 1396, 1222, 1195, 759 cm$^{-1}$

Anal. Calcd for C$_{25}$H$_{29}$N$_3$O$_2$—C$_6$H$_8$O$_7$-2.5H$_2$O: C, 58.12; H, 6.61; N, 6.56. Found: C, 58.09; H, 6.31; N, 6.31.

Example 10
2,3-Dihydro-1'-{[1-(2-dimethylamino-2-oxoethyl)-2-oxo-1,2,3,4-tetrahydro-3-quinolinyl]methyl}spiro[1H-indene-1,4'-piperidine]

To a stirred solution of 2,3-dihydro-1'-{[1-(carboxymethyl)-2-oxo-1,2,3,4-tetrahydro-3-quinolinyl]methyl}spiro[1H-indene-1,4'-piperidine] (112.8 mg, 0.279 mmol) and dimethylamine hydrochloride (68.2 mg, 0.837 mmol) in CH$_2$Cl2 (8 ml) was added WSC (107 mg, 0.558 mmol) and HOBt (75.4 mg, 0.558 mmol) at 0° C. After 18 h stirring at room temperature, the reaction mixture was quenched with saturated aqueous $NaHCO_3$ solution (15 ml), extracted with $CH_2Cl_2$ (20 ml×3). The extracts combined were washed with brine, dried ($Na_2SO_4$), filtered, and concentrated to give 137.6 mg of crude product. This was purified by preparative TLC (1 mm thick silica gel plate: $CH_2Cl_2$/methanol:20/1 2 developed then n-hexane/acetone/triethylamine: 20/10/1) to afford 92.6 mg (77%) of title compound as colorless oil.

$^1$H NMR (300 MHz, $CDCl_3$) δ 7.25–7.11 (6H, m), 7.00 (1H, ddd, J=1.1, 7.5, 7.5 Hz), 6.74 (1H, br.d, J=7.5 Hz), 4.76 (1H, d, J=16.3 Hz), 4.63 (1H, d, J=16.5 Hz), 3.18–3.08 (1H, m), 3.13 (3H, s), 3.00 (3H, s), 2.98–2.81 (6H, m), 2.56–2.53 (1H, m), 2.53–2.50 (1H, m), 2.36 (1H, ddd, J=2.4, 11.7, 12.3 Hz), 2.18–2.06 (1H, m), 1.99 (2H, t, J=7.3 Hz), 2.00–1.82 (2H, m), 1.57–1.46 (2H, m).

This solid (92.6 mg) was converted to citric acid salt similar to that described in Example 1 to afford 113.6 mg of citric acid salt as white solid.

MS (ESI positive) m/z: 432 $(M+H)^+$.

IR(KBr): 2937, 1716, 1652, 1604, 1396, 1197, 759 $cm^{-1}$

Anal. Calcd for $C_{27}H_{33}N_3O_2$—$C_6H_8O_7$—$H_2O$—$CH_2Cl_2$: C, 58.81; H, 6.48; N, 6.14. Found: C, 59.00; H, 6.72; N, 5.71.

Preparation 11

5-Hydroxymetyl-1,2,5,6-tetrahydro-4H-pyrrolo[3,2,1-ij]quinoline

To a stirred solution of 4-oxo-1,2,5,6-tetrahydro-4H-pyrrolo[3,2,1-ij]quinoline (700 mg, 4.04 mmol) and ethyl cyanoformate (0.72 ml, 7.274 mmol) in THF (20 ml) was added a solution of lithium diisopropylamide (this was prepared from 1.4 ml of diisopropylamine and 6.4 ml of 1.59 M solution of n-butyllithium in hexane) in THF (20 ml) at −78° C. After 3 h stirring at −78° C. to −50° C., the reaction mixture was quenched with water (100 ml) and extracted with ethyl acetate (40 ml×3). The extracts combined were dried ($Na_2SO_4$), filtered, and concentrated to give 1.36 g of crude product, which was purified by silica gel column chromatography (n-hexane/ethyl acetate: 3/2) to give 666.6 mg (67%) of ethyl ester derivative as yellow white solid.

$^1$H NMR (300 MHz, $CDCl_3$) δ 7.09 (1H, br.d, J=7.3 Hz), 7.01 (1H, br.d, J=7.1 Hz), 6.94 (1H, dd, J=7.1, 7.5 Hz), 4.29–4.13 (2H, m), 4.11 (2H, dd, J=8.2, 8.4 Hz), 3.66 (1H, dd, J=7.7, 8.3 Hz), 3.37 (1H, dd, J=8.4, 16.3 Hz), 3.20 (2H, dd, J=7.7, 9.2 Hz), 3.07 (1H, dd, J=7.3, 16.5 Hz), 1.26 (3H, t, J=7.1 Hz).

To a stirred solution of the above ester (227.4 mg, 0.927 mmol) in ethanol (10 ml) was added sodium borohydride (105.2 mg, 2.78 mmol) at 0° C. After 1 day stirring at 0° C., 70 mg of sodium borohydride was added to the reaction mixture. After 7 h stirring, 70 mg of sodium borohydride and ethanol (1 ml) was added to the reaction mixture at 0° C. After 17 h stirring, 70 mg of sodium borohydride and ethanol (1 ml) was added to the reaction mixture at 0° C. After 6.5 h stirring at 0° C. to room temperature, the reaction mixture was quenched with saturated aqueous $NaHCO_3$ solution (40 ml) and extracted with $CH_2Cl_2$ (30 ml×3). The extracts combined were dried ($Na_2SO_4$), filtered, and concentrated. The residue was purified by preparative TLC (1 mm thick silica gel plate: n-hexane/ethyl acetate:1/3) to afford 79.8 mg (46%) of title compound as an oil.

$^1$H NMR (270 MHz, $CDCl_3$) δ 6.94 (1H, br.d, J=7.3 Hz), 6.85 (1H, br.d, J=7.6 Hz), 6.64 (1H, dd, J=7.4, 7.4 Hz), 3.76 (1H, dd, J=5.5, 10.6 Hz), 3.67 (1H, dd, J=6.8, 10.9 Hz), 3.37–3.14 (3H, m), 2.97–2.75 (4H, m), 2.55–2.32 (2H, m), 1.69 (1H, br.s).

MS(EI direct) m/z 1 89$(M)^+$.

Example 11

2,3-Dihydro-1'-[(1,2,5,6-tetrahydro-4H-pyrrolo[3,2,1-ij]quinolin-5-yl)methyl]spiro[1H-indene-1,4'-piperidine]

This was prepared according to the procedure described in Example 5 using 5-hydroxymetyl-1,2,5,6-tetrahydro-4H-pyrrolo[3,2,1-ij]quinoline instead of 4-oxo-5-hydroxymethyl-1,2,5,6-tetrahydro-4H-pyrrolo[3,2,1 -ij]quinoline. In the alkylation step, $K_2CO_3$ and isopropanol was used instead of diisopropylethylamine and THF. 109.9 mg (55%) of title compound was obtained as colorless oil.

$^1$H NMR (300 MHz, $CDCl_3$) δ 7.25–7.11 (4H, m), 6.94 (1H, br.d, J=7.1 Hz), 6.86 (1H, br.d, J=7.5 Hz), 6.63 (1H, dd, J=7.3, 7.3 Hz), 3.51–3.43 (1H, m), 3.38–3.32 (1H, m), 3.14–3.00 (1H, m), 3.00–2.74 (7H, m), 2.58–2.36 (5H, m), 2.26–2.08 (2H, m), 2.01 (2H, t, J=7.5 Hz), 2.00–1.89 (2H, m), 1.58–1.49 (2H, m).

This solid (109.9 mg) was converted to citric acid salt similar to that described in Example 1 to afford 121.9 mg of citric acid salt as pale yellow solid.

MS (ESI positive) m/z: 359 $(M+H)^+$.

IR(KBr): 2930, 1733, 1716, 1558, 1541, 1508, 1458, 759 $cm^{-1}$

Anal. Calcd for $C_{25}H_{30}N_2$—$C_6H_8O_7$—$H_2O$: C, 65.48; H, 7.09; N, 4.93. Found: C, 65.57; H, 7.12; N, 4.66.

Example 12

2,3-Dihydro-1'-[(3-oxo-2,3,6,7-tetrahydro-1H,5H-pyrido[3,2,1-ij]quinolin-2-yl)methyl]spiro[1H-indene-1,4'-piperidine]

To a stirred solution of 2,3-dihydro-1'-[(5-oxo-2,3-dihydro-1H,5H-pyrido[3,2,1-ij]quinolin-6-yl)methyl]spiro[1H-indene-1,4'-piperidine] (66.4 mg, 0.173 mmol, this was prepared in example 3) in toluene (5 ml) was added a solution of L-selectride (1M solution in THF, 0.21 ml, 0.21 mmol) at −78° C. After 1.5 h stirring, 0.21 ml of a solution of L-selectride was added to the reaction mixture at −78° C. After 2.5 h stirring at −78 to −60° C., 0.34 ml of a solution of L-selectride was added to the reaction mixture at −60° C. After 1 h stirring at −60 to −50° C., the reaction mixture was quenched with saturated aqueous NH4Cl solution (10 ml) and extracted with $CH_2Cl_2$ (15 ml×3). The extracts combined were dried ($Na_2SO_4$), filtered, and concentrated to give 170.6 mg of crude product, which was purified by preparative TLC (1 mm thick silica gel plate: n-hexane/acetone/triethylamine:40/10/1, 2 developed) to afford 32.6 mg (49%) of title compound as colorless oil.

$^1$H NMR (270 MHz, $CDCl_3$) δ 7.25–7.11 (4H, m), 7.08–6.98 (2H, m), 6.92 (1H, dd, J=7.4, 7.4 Hz), 4.04–3.93 (1H, m), 3.84–3.72 (1H, m), 3.14–3.00 (1H, m), 2.92–2.70 (9H, m), 2.60–2.48 (1H, m), 2.44–2.29 (1H, m), 2.20–2.07 (1H, m), 2.05–1.80 (6H, m), 1.57–1.41 (2H, m).

This solid was converted to citric acid salt similar to that described in Example 1 to afford citric acid salt as white solid.

MS (ESI positive) m/z: 387 $(M+H)^+$.

IR(KBr): 3408, 2939, 2569, 1724, 1649, 1595, 1475, 1182, 761 $cm^{-1}$

Anal. Calcd for $C_{26}H_{30}N_2O$—$C_6H_8O_7$-1.5$H_2O$: C, 63.46; H, 6.82; N, 4.63. Found: C, 63.34; H, 6.85; N, 4.29.

Preparation 12

2,3-Dihydro-1'-{[1-(3-phthalimidopropyl)-2-oxo-1,2,3,4-tetrahydro-3-quinolinyl]methyl}spiro[1H-indene-1,4'-piperidine]

This was prepared according to the procedure described in preparation 8 using 3-bromopropylphthalimide instead of (3-bromopropoxy)-t-butyldimethylsilane. 192.1 mg (89%) of title compound was obtained as yellow oil.

$^1$H NMR (300 MHz, CDCl$_3$) δ7.87–7.80 (2H, m), 7.74–7.68 (2H, m), 7.25–7.10 (6H, m), 7.00 (1H, dd, J=7.4, 7,5 Hz), 6.95 (1H, br.d, J=8.1 Hz), 4.13–3.94 (2H, m), 3.78 (2H, t, J=7.1 Hz), 3.20–3.07 (1H, m), 2.98–2.70 (7H, m), 2.60–2.42 (1H, m), 2.406–2.20 (1H, m), 2.20–1.80 (7H, m), 1.56–1.45 (2H, m).

MS(EI direct) m/z: 533 (M)$^+$.

Preparation 13

2,3-Dihydro-1'-{[1-(3-aminopropyl)-2-oxo-1,2,3,4-tetrahydro-3-quinolinyl]methyl}spiro[1H-indene-1,4'-piperidine]

To a stirred solution of 2,3-dihydro-1'-{[1-(3-phthalimidopropyl)-2-oxo-1,2,3,4-tetrahydro-3-quinolinyl]methyl}spiro[1H-indene-1,4'-piperidine] (242.9 mg, 0.455 mmol) in methanol (15 ml) was added hydrazine (50.1 mg, 1 mmol) and the reaction mixture was refluxed for 7 h. After evaporation of the solvent, the reaction mixture was diluted with saturated aqueous NaHCO$_3$ solution (20 ml), extracted with CH$_2$Cl$_2$ (30 ml×3), washed with water (20 ml), dried (Na$_2$SO$_4$), filtered, and concentrated to give 169.1 mg of crude product, which was purified by preparative TLC (1 mm thick silica gel plate: CH$_2$Cl$_2$/methanol:20/1, then ethyl acetate/isopropanol/25%NH$_4$OH: 20/2/1) to afford 71.3 mg (39%) of title compound as pale yellow oil.

$^1$H NMR (270 MHz, CDCl$_3$) δ7.28–7.12 (6H, m), 7.07–6.99 (2H, m), 4.11 (1H, ddd, J=7.1, 7.1, 14.3 Hz), 4.01 (1H, ddd, J=7.0, 7.0, 14.3 Hz), 3.18–3.00 (2H, m), 2.95–2.70 (6H, m), 2.55–2.45 (1H, m), 2.43–2.25 (4H, m), 2.18–1.758 (8H, m), 1.60–1.46 (2H, m).

MS (ESI positive) m/z: 404 (M+H)$^+$.

Example 13

2,3-Dihydro-1'-{[1-(3-dimethylaminopropyl)-2-oxo-1,2,3,4-tetrahydro-3-quinolinyl]methyl}spiro[1H-indene-1,4'-piperidine]

To a stirred solution of 2,3-dihydro-1'-{[1-(3-aminopropyl)-2-oxo-1,2,3,4-tetrahydro-3-quinolinyl]methyl}spiro[1H-indene-1,4'-piperidine] (71.3 mg, 0.177 mmol) and 37% folmaldehyde (0.025 ml, 0.885 mmol) in acetonitrile (5 ml) was added sodium cyanoborohydride (17.8 mg, 0.283 mmol) at 0° C. and resulting mixture was stirred at room temperature for 8 h. To this reaction mixture was added folmaldehyde (0.005 ml) and sodium cyanoborohydride (11.1 mg) at room temperature. After 15 h stirring, the reaction mixture quenched with saturated aqueous NaHCO$_3$ solution (10 ml) and extracted with CH$_2$Cl$_2$ (20 ml×3). The extracts combined were dried (MgSO$_4$), filtered, and concentrated. The residue was purified by preparative TLC (1 mm thick plate, ethyl acetate/isopropanol/25%NH$_4$OH: 60/2/1 then 20/2/1) to afford 14.5 mg (19%) of title compound as pale yellow oil.

$^1$H NMR (270 MHz, CDCl$_3$) δ7.28–7.11 (6H, m), 7.08–6.97 (2H, m), 3.97 (2H, br.t, J=7.6 Hz), 3.15–3.05 (1H, m), 2.93–2.70 (6H, m), 2.51–2.45 (1H, m), 2.40–2.25 (3H, m), 2.23 (6H, s), 2.20–2.10 (1H, m), 2.05–1.75 (7H, m), 1.58–1.46 (2H, m).

This solid was converted to citric acid salt similar to that described in Example 1 to afford citric acid salt as white solid.

MS (ESI positive) m/z: 432 (M+H)$^+$.

Anal. Calcd for C$_{28}$H$_{37}$N$_3$O—C$_6$H$_8$O$_7$-1.5H$_2$O: C, 62.75; H, 7.43; N, 6.46. Found: C, 62.78; H, 7.67; N, 6.12.

Example 14

2,3-Dihydro-1'-{[1-(2,2,2-trifluoroethyl)-2-oxo-1,2,3,4-tetrahydro-3-quinolinyl]methyl}spiro[1H-indene-1,4'-piperidine]

This was prepared according to the procedure described in preparation 12 using 2,2,2-trifluoroethyl trifluoromethanesulfonate instead of 3-bromopropylphthalimide. 30.4 mg (49%) of title compound was obtained as colorless oil.

$^1$H NMR (270 MHz, CDCl$_3$) δ7.31–7.03 (8H, m), 4.72–4.50 (2H, m), 3.23–3.11 (1H, m), 2.96–2.72 (7H, m), 2.60–2.49 (1H, m), 2.42–2.30 (1H, m), 2.22–2.09 (1H, m), 2.00 (2H, t, J=7.3 Hz), 2.00–1.82 (2H, m), 1.57–1.47 (2H, m).

This solid was converted to citric acid salt similar to that described in Example 1 to afford citric acid salt as white solid.

MS (ESI positive) m/z: 429 (M+H)$^+$.

IR(KBr): 3417, 2939, 2563, 1683, 1606, 1257, 1141, 759 cm$^{-1}$

Anal. Calcd for C$_{25}$H$_{27}$F$_3$N$_2$O—C$_6$H$_8$O$_7$—H$_2$O: C, 58.30; H, 5.84; N, 4.39. Found: C, 58.46; H, 5.98; N, 4.05.

Example 15

2,3-Dihydro-1'-{[1-(2-dimethylaminoethyl)-2-oxo-1,2,3,4-tetrahydro-3-quinolinyl]methyl}spiro[1H-indene-1,4'-piperidine]

This was prepared according to the procedure described in preparation 12 using 2-chloroethyldimethylamine instead of 3-bromopropylphthalimide. 40.0 mg (62%) of title compound was obtained as colorless oil.

$^1$H NMR (270 MHz, CDCl$_3$) δ7.30–7.11 (6H, m), 7.08–6.98 (2H, m), 4.12–4.02 (2H, m), 3.15–3.05 (1H, m), 2.93–2.70 (7H, m), 2.60–2.45 (3H, m), 2.40–2.28 (1H, m), 2.34 (6H, s), 2.18–2.07 (1H, m), 2.00 (2H, t, J=7.2 Hz), 2.00–1.82 (2H, m), 1.57–1.46 (2H, m).

This solid was converted to citric acid salt similar to that described in Example 1 to afford citric acid salt as white solid.

MS (ESI positive) m/z: 418 (M+H)$^+$.

IR(KBr): 2929, 1654, 1602, 1458, 11396, 761 cm$^{-1}$

Anal. Calcd for C$_{27}$H$_{35}$N$_3$O—C$_6$H$_8$O$_7$-3H$_2$O: C, 61.12; H, 7.18; N, 6.11. Found: C, 60.75; H, 7.12; N, 6.05.

Preparation 14

2,3-Dihydro-1'-{[2-oxo-1-([(1-t-butoxycarbonyl)-4-piperidinyl]methyl)-1,2,3,4-tetrahydro-3-quinolinyl]methyl}spiro[1H-indene-1,4'-piperidine]

This was prepared according to the procedure described in preparation 12 using (1-t-butoxycarbonyl-4-piperidinyl) methyl bromide instead of 3-bromopropylphthalimide. 136 mg (80%) of title compound was obtained as pale yellow oil.

$^1$H NMR (300 MHz, CDCl$_3$) δ7.28–7.12 (6H, m), 7.06–6.96 (2H, m), 4.18–3.95 (2H, m), 3.18–3.05 (1H, m), 2.94–2.73 (7H, m), 2.70–2.43 (3H, m), 2.38–2.25 (1H, m), 2.19–2.07 (1H, m), 2.00 (2H, t, J=7.4 Hz), 2.00–1.80 (2H, m), 1.65–1.40 (7H, m), 1.44 (9H, s), 1.35–1.20 (2H, m).

MS(EI direct) m/z: 543 (M)$^+$.

Example 16
2,3-Dihydro-1'-{[2-oxo-1-(4-piperidinylmethyl)-1,2,3,4-tetrahydro-3-quinolinyl]methyl}spiro[1H-indene-1,4']-piperidine]

To a stirred solution of 2,3-dihydro-1'-{[2-oxo-1-([(1-t-butoxycarbonyl)-4-piperidinyl]methyl)-1,2,3,4-tetrahydro-3-quinolinyl]methyl}spiro[1H-indene-1,4'-piperidine] (130 mg, 0.239 mmol) in $CH_2Cl_2$ (4 ml) was added trifluoroacetic acid (1 ml) at 0° C. After 0.5 h stirring at 0° C. and 0.5 h stirring at room temperature, the solvent was evaporated. The residue was diluted with saturated aqueous $NaHCO_3$ solution and extracted with $CH_2Cl_2$ (20 ml×3). The extracts combined were dried ($Na_2SO_4$), filtered, and concentrated to give 108.1 mg of crude product. This was purified by preparative TLC (1 mm thick plate, ethyl acetate/isopropanol/25%$NH_4OH$: 10/2/1, 20/2/1, and $CH_2Cl_2$/methanol/triethylamine: 10/1/1) to give 26.5 mg (55%) of title compound as colorless oil.

$^1$H NMR (300 MHz, $CDCl_3$) δ7.28–7.12 (6H, m), 7.05–6.97 (2H, m), 3.98 (1H, dd, J=7.7, 13.9 Hz), 3.80 (1H, dd, J=7.0, 14.3 Hz), 3.18–3.02 (3H, m), 2.95–2.72 (7H, m), 2.60–2.45 (3H, m), 2.38–2.27 (1H, m), 2.18–2.07 (1H, m), 2.18–2.07 (1H, m), 1.99 (2H, t, J=7.3 Hz), 2.00–1.80 (3H, m), 1.67–1.58 (2H, m), 1.57–1.46 (2H, m), 1.34–1.19 (2H, m).

This solid was converted to citric acid salt similar to that described in Example 1 to afford citric acid salt as white solid.

MS (ESI positive) m/z: 444 (M+H)$^+$.

Anal. Calcd for $C_{29}H_{37}N_3O—C_6H_8O_7$-2.5$H_2O$: C, 61.75; H, 7.40; N, 6.17. Found: C, 61.73; H, 7.49; N, 5.85.

Example 17
3-(2,3-Dihydro-1'H-spiro[indene-1,4'piperidin]-1'-ylmethyl-1-isopropyl-3,4-dihydroquinolin-2(1H)-one To a stirred solution of 2,3-dihydro-1'-[(2-oxo-1,2,3,4-tetrahydro-3-quinolinyl)methyl]spiro[1H-indene-1,4'-piperidine] (this was prepared as Example 7, 60 mg, 0.173 mmol) and NaH (8.3 mg, 0.208 mmol) in DMF (5 ml) was added isopropyl bromide (42.6 mg, 0.346 mmol) at 0° C. and the resulting reaction mixture was stirred at 50° C. for 17 h. Then NaH (8.3 mg, 0.208 mmol) and isopropyl bromide (42.6 mg, 0.346 mmol) were added to the reaction mixture. After 1 d stirring at 60° C., the reaction mixture was quenched with saturated $NaHCO_3$ solution (15 ml) and extracted with $CH_2Cl_2$ (20 ml×3). The extracts combined were dried ($Na_2SO_4$), filtered, and concentrated. The resulting residue was dissolved to ethyl acetate (30 ml) and was washed with water (20 ml) and brine (20 ml), dried ($Na_2SO_4$), filtered, and concentrated to give 67 mg of crude product, which was purified by preparative TLC (1 mm thick silica gel plate: n-hexane/acetone/triethylamine:80/10/1, 2 times developed) to afford 28.9 mg (43%) of title compound as colorless oil.

$^1$H NMR (270 MHz, $CDCl_3$) δ7.24–7.10 (7H, m), 7.04–6.98 (1H, m), 4.68 (1H, qq, J=6.9, 7.1 Hz), 3.07–3.01 (1H, m), 2.91–2.67 (8H, m), 2.52–2.31 (2H, m), 2.12–1.67 (6H, m), 1.54 (3H, d, J=6.9 Hz), 1.52 (3H, d, J=7.1 Hz).

This oil (28.9 mg, 0.074 mmol) and citric acid (14.2 mg, 0.074 mmol) was dissolved in methanol (3 ml), and the solution was stirred at room temperature for 1.5 h. The solvent was evaporated and dried (60° C., 1 d) to give 38.9 mg of citrate salt as white amorphous solid.

MS(ESI positive) m/z: 389.20(M+1)$^+$.

Anal. Calcd for $C_{26}H_{32}N_2O—C_6H_8O_7—H_2O$: C, 64.20; H, 7.07; N, 4.68. Found: C, 64.34; H, 6.86; N, 4.56.

Example 18
1'-(1,2,3,4-Terahydroquinolin-3-ylmethyl)-2,3-dihydrospiro[indene-1,4'piperidin]

To a stirred solution of 2,3-dihydro-1'-[(2-oxo-1,2,3,4-tetrahydro-3-quinolinyl)methyl]spiro[1H-indene-1,4'-piperidine] (this was prepared as Example 7, 60 mg, 0.173 mmol) in THF (3 ml) was added LiAlH4 (9.8 mg, 0.26 mmol) at 0° C. and the resulting reaction mixture was stirred at room temperature for 2 h. Then $LiAlH_4$ (9.8 mg, 0.26 mmol) was added to the reaction mixture at 0° C. and the resulting reaction mixture was stirred at room temperature for 1 h. The reaction mixture was quenched with saturated $Na_2SO_4$ solution (5 drops) and was diluted with $CH_2Cl_2$. After 15 min stirring at room temperature, the reaction mixture was filtered using Celite. The filtrate was concentrated to give 70.1 mg of crude product, which was purified by preparative TLC (1 mm thick silica gel plate: n-hexane/acetone/triethylamine:40/10/1, 2 times developed, then 1 mm thick silica gel plate: n-hexane/acetone/triethylamine:50/10/1) to afford 56.6 mg (49%) of title compound as colorless oil.

$^1$H NMR (300 MHz, $CDCl_3$) δ7.24–7.12 (4H, m), 6.99–6.95 (2H, m), 6.64–6.58 (1H, m), 6.50–6.47 (1H, m), 3.48–3.42 (1H, m), 3.02 (1H, dd, J=8.6, 11.2 Hz), 2.93–2.83 (5H, m), 2.54–1.90 (11H, m), 1.55–1.51 (2H, m).

This oil (56.6 mg, 0.17 mmol) and citric acid (32.7 mg, 0.17 mmol) was dissolved in methanol (4 ml) and CH2Cl2 (1 ml), and the solution was stirred at room temperature for 2 h. The solvent was evaporated and the resulting residue was dissolved in hexane (5 ml) and $CH_2Cl_2$ (1 ml). The solvent was evaporated to give white solid which was washed with ether and dried (60° C., 1 d) to give 74.7 mg of citrate salt as white amorphous solid.

MS(ESI positive) m/z: 333.15(M+1)$^+$.

IR(KBr): 3395, 1742, 1607, 1587, 1501, 1477, 1212, 758 cm$^{-1}$

Anal. Calcd for $C_{23}H_{28}N_2—C_6H_8O_7$-1.5$H_2O$: C, 63.14; H, 7.13; N, 5.08. Found: C, 63.20; H, 6.97; N, 4.77.

Preparation 15
8-Methoxy-2-oxo-1,2,3,4-tetrahydroquinoline-3-carboxylic acid To a stirred solution of diethyl malonate (8.84 g, 55.2 mmol), 3-methoxy-2-nitrobenzaldehyde (5.00 g, 27.6 mmol) in pyridine (120 ml) was added piperidine (352.5 mg, 4.14 mmol) at room temperature, then the reaction mixture was warmed to reflux with stirring for 17 h. To the reaction mixture was added diethyl malonate (8.84 g, 55.2 mmol) and piperidine (352.5 mg, 4.14 mmol) and reflux was continued another 7 h. The reaction mixture was quenched with water (400 ml), extracted with ethyl acetate (300 ml×1). The extract was washed with water (300 ml), 1N HCl (200 ml), and saturated $NaHCO_3$ solution (300 ml), dried ($Na_2SO_4$), filtered, and concentrated to give 14.43 g of crude oil. This was purified by silica gel column chromatography (n-hexane/ethyl acetate: 3/1) to give 3.4896 g (39%) of diethyl (3-methoxy-2-nitrobenzylidene)malonate as brown color oil.

$^1$H NMR (270 MHz, $CDCl_3$) δ7.65 (1H, s), 7.42 (1H, dd, J=7.9, 8.4 Hz), 7.12–7.03 (2H, m), 4.30 (2H, q, J=7.5 Hz), 4.21 (2H, q, J=7.3 Hz), 3.93 (3H, s), 1.33 (3H, t, J=7.6 Hz), 1.18 (3H, t, J=7.1 Hz).

A mixture of diethyl (3-methoxy-2-nitrobenzylidene) malonate (2.03 g, 6.28 mmol) and 10% Pd/C (200 mg) in ethanol (150 ml) was stirred under hydrogen atmosphere at room temperature for 22 h. Then the reaction mixture was refluxed under nitrogen atmosphere for 1 d. After Celite filtration, the filtrate was concentrated to give 1.51 g of crude product, which was purified by silica gel column chromatography (n-hexane/ethyl acetate: 2/1 to 1/1) to give 0.74 g (47%) of ethyl 8-methoxy-2-oxo-1,2,3,4-tetrahydroquinoline-3- carboxylate.

$^1$H NMR (270 MHz, CDCl$_3$) δ7.84 (1H, br.s), 6.96 (1H, dd, J=7.9, 7.9 Hz), 6.83–6.75 (2H, m), 4.22 (2H, q, J=7.1 Hz), 3.86 (3H, s), 3.60 (1H, dd, J=6.1, 9.1 Hz), 3.38 (1H, dd, J=9.4, 15.7 Hz), 3.12 (1H, J=6.2, 16.0 Hz), 1.25 (3H, t, J=7.2 Hz).

To a stirred solution of ethyl 8-methoxy-2-oxo-1,2,3,4-tetrahydroquinoline-3-carboxylate (400 mg, 1.6 mmol) in methanol (10.5 ml) and THF (10.5 ml) was added 1N NaOH (3.2 ml) at 0° C. and resulting mixture was stirred at room temperature for 1 h. The reaction mixture was acidified with 1N HCl (30 ml), extracted with ethyl acetate (30 ml), dried (Na$_2$SO$_4$), filtered, and concentrated to give 319.3 mg (90.1%) of title compound as pale yellow solid.

$^1$H NMR (270 MHz, DMSO-d6) δ 12.69 (1H, br.s), 9.40 (1H, s), 6.95–6.78 (3H, m), 3.79 (3H, s), 3.46 (1H, t, J=7.3 Hz), 3.10 (1H, d, J=7.3 Hz).

Example 19

3-(2,3-Dihydro-1'H-spiro[indene-1,4'piperidin]-1'-ylmethyl)-1,2,3,4-tetrahydroquinolin-8-ol To a stirred solution of 2,3-dihydro-1'H-spiro[indene-1, 4'piperidin] hydrochloride (315.5 mg, 1.41 mmol), 8-methoxy-2-oxo-1,2,3,4-tetrahydroquinoline-3-carboxylic acid (312.9 mg, 1.41 mmol), and triethylamine (856.1 mg, 8.46 mmol) in CH$_2$Cl$_2$ (35 ml) was added hydroxybenztriazole (381.1 mg, 2.82 mmol) and WSC (856.1 mg, 2.82 mmol) at 0° C. and the resulting reaction mixture was stirred at room temperature for 18 h. The reaction mixture was quenched with saturated NaHCO$_3$ solution (50 ml) and extracted with CH$_2$Cl$_2$ (30 ml×3). The extracts combined were dried (Na$_2$SO$_4$), filtered, and concentrated to give 791.8 mg of crude product, which was purified by silica gel column chromatography (n-hexane/ethyl acetate: 1/2) to give 376.4 mg (68%) of amide compound as colorless oil. To a stirred solution of this amide derivative (50 mg, 0.128 mmol) in THF (2 ml) was added 1M solution of BH3-THF (1.2 ml, 1.2 mmol) at room temperature. After 2.5 h stirring at room temperature and 4.5 h with reflux, 6N HCl (0.78 ml, 4.66 mmol) was added to the reaction mixture and the resulting mixture was refluxed for 1 h. The reaction mixture was basified with 2N NaOH, extracted with CH$_2$Cl$_2$ (20 ml×3), dried (Na$_2$SO$_4$), filtered, and concentrated to give 96.4 mg of crude product, which was purified by preparative TLC (1 mm thick silica gel plate: CH$_2$Cl$_2$/methanol: 15/1) to afford 17.9 mg (40%) of title compound as pale yellow oil.

$^1$H NMR (300 MHz, CDCl$_3$) δ 7.24–7.13 (5H, m), 6.62–6.57 (3H, m), 3.49 (1H, m), 2.99–2.87 (6H, m), 2.48–2.12 (6H, m), 2.05–1.95 (5H, m), 1.56–1.50 (2H, m). This oil (14 mg, 0.04 mmol) and citric acid (7.7 mg, 0.04 mmol) was dissolved in methanol (2 ml) and CH$_2$Cl$_2$ (0.5 ml), and the solution was stirred at room temperature for 1.5 h. The solvent was evaporated and the resulting solid was dried (60° C., 1 d) to give 17 mg of citrate salt as white amorphous solid.

MS(ESI positive) m/z: 349.13 (M+1)$^+$.
IR(KBr): 3400, 1720, 1589, 1479, 1194, 762 cm$^{-1}$ Example 20

6-(2,3-Dihydro-1'H-spiro[indene-1,4'piperidin]-1'-ylmethyl)-6,7-dihydro-5H-[1,4]oxazino[2,3,4-ij]quinolin-3(2H)-one To a stirred mixture of 3-(2,3-dihydro-1'H-spiro[indene-1, 4'piperidin]-1'-ylmethyl) -1,2,3,4-tetrahydroquinolin-8-ol (this was prepared as Example 19, 39.3 mg, 0.113 mmol) and NaHCO$_3$ (28.5 mg, 0.339 mmol) in THF (4 ml) was added a solution of chloroacetyl chloride (15.4 mg, 0.136 mmol) in THF (2 ml) at room temperature and the resulting reaction mixture was stirred at room temperature for 1 h. The reaction mixture was quenched with saturated NaHCO$_3$ solution and extracted with CH2Cl2 (20 ml×3). The extracts combined were dried (Na$_2$SO$_4$), filtered, and concentrated to afford 45.8 mg of crude amide product as yellow oil.

$^1$H NMR (270 MHz, CDCl$_3$) δ 7.25–7.16 (5H, m), 6.94–6.77 (3H, m), 4.62 (2H, s), 4.38–4.32 (1H, m), 3.30 (1H, m), 3.01–2.88 (5H, m), 2.71–1.99 (10H, m), 1.60–1.55 (2H, m).

A mixture of this oil (45.8 mg, 0.108 mmol) and K2CO3 (44.8 mg, 0.324 mmol) in acetonitrile (4 ml) was stirred at room temperature for 15 h. The reaction mixture was diluted with water (20 ml), extracted with CH2Cl2 (20 ml×3), washed with brine (30 ml), dried (Na2SO4), filtered, and concentrated to give 36.3 mg of crude product, which was purified by preparative TLC (silica gel plate: n-hexane/acetone:3/1, 2 developed) to afford 23.4 mg (53% for 2 steps) of title compound as colorless oil.

$^1$H NMR (270 MHz, CDCl$_3$) δ 7.25–7.12 (4H, m), 6.93–6.79 (3H, m), 4.65 (1H, d, J=15.8 Hz), 4.59 (1H, d, J=15.3 Hz), 4.43 (1H, ddd, J=1.5, 3.8, 13.0 Hz), 3.18 (1H, dd, J=10.0, 13.2 Hz), 3.00–2.78 (5H, m), 2.55 (1H, dd, J=10.0, 16.3 Hz), 2.40–2.37 (2H, m), 2.24–2.15 (3H, m), 2.03–1.91 (4H, m), 1.54–1.50 (2H, m).

This oil (56.6 mg, 0.17 mmol) and citric acid (32.7 mg, 0.17 mmol) was dissolved in methanol (2 ml) and THF (0.5 ml), and the solution was stirred at room temperature for 2 h. The solvent was evaporated and the resulting residue was dissolved in hexane (5 ml) and CH$_2$Cl$_2$ (0.5 ml). The solvent was evaporated to give white solid which was washed with ether and dried (60° C., 1 d) to give 22.9 mg of citrate salt as white amorphous solid.

MS(ESI positive) m/z: 389.15(M+1)$^+$.
Anal. Calcd for C$_{25}$H$_{28}$N$_2$O$_2$—C$_6$H$_8$O$_7$—1.5H$_2$O: C, 61.28; H, 6.47; N, 4.61. Found: C, 60.90; H, 6.29; N, 4.34.

Example 21

5-(2,3-Dihydro-1'H-spiro[indene-1,4'piperidin]-1'-ylmethyl)-5,6-dihydro-4H-[1,3]oxazolo[5,4,3-ij]quinolin-2-one To a stirred solution of 3-(2,3-dihydro-1'H-spiro[indene-1, 4'piperidin]-1'-ylmethyl)-1,2,3,4-tetrahydroquinolin-8-ol (this was prepared as Example 19, 33.8 mg, 0.097 mmol) in THF (3 ml) was added 1,1'-carbonyldiimidazole (18.8 mg, 0.116 mmol) at 0 ° C. and the resulting reaction mixture was stirred at room temperature for 7 h. The reaction mixture was quenched with water (15 ml) and extracted with CH$_2$Cl$_2$ (15 ml×3). The extracts combined were dried (Na$_2$SO$_4$), filtered, and concentrated to afford 39.2 mg of crude product, which was purified by preparative TLC (silica gel plate: n-hexane/acetone:2/1, 2 developed) to afford 27.4 mg (75%) of title compound as colorless oil.

$^1$H NMR (270 MHz, CDCl$_3$) δ 7.25–7.13 (4H, m), 7.02–6.95 (3H, m), 4.21 (1H, dd, J=2.6, 12.3 Hz), 3.50–3.40 (1H, m), 3.00–2.74 (5H, m), 2.63–2.38 (4H, m), 2.31–2.10 (2H, m), 2.03–1.88 (4H, m), 1.56–1.51 (2H, m).

This oil (27.3 mg, 0.073 mmol) and citric acid (14 mg, 0.073 mmol) was dissolved in methanol (2 ml) and CH2Cl2 (0.5 ml), and the solution was stirred at room temperature for 2 h. The solvent was evaporated and the resulting residue was dissolved in hexane (5 ml) and $CH_2Cl_2$ (0.5 ml). The solvent was evaporated to give white solid which was washed with ether and dried (60° C., 1 d) to give 27.6 mg of citrate salt as white amorphous solid.

MS(ESI positive) m/z : 375.14(M+1)$^+$.

Anal. Calcd for $C_{24}H_{26}N_2O_2$—$C_6H_8O_7$—$2H_2O$: C, 59.79; H, 6.36; N, 4.65. Found: C, 59.47; H, 6.00; N, 4.50

Example 22

6-(2,3-Dihydro-1'H-spiro[indene-1,4'piperidin]-1'-ylmethyl)-2,3,6,7-tetrahydro-1H,5H-pyrido[3,2,1-ij]quinolin-1,5-dione A mixture of 2,3-dihydro-1'-[(2-oxo-1,2,3,4-tetrahydro-3-quinolinyl)methyl]spiro[1H-indene-1,4'-piperidine] (this was prepared as Example 7, 200 mg, 0.577 mmol), benzyltriethylammonium chloride (65.8 mg, 0.289 mmol), $K_2CO_3$ (199.4 mg, 1.443 mmol), and ethyl 3-bromopropionate (177.6 mg, 0.981 mmol) in acetonitrile (20 ml) was refluxed for 18 h. To this reaction mixture was added benzyltriethylammonium chloride (65.8 mg, 0.289 mmol), $K_2CO_3$ (199.4 mg, 1.443 mmol), and ethyl 3-bromopropionate (177.6 mg, 0.981 mmol) in acetonitrile (3 ml) and resulting mixture was refluxed for 24 h. The reaction mixture was quenched with water (50 ml) and extracted with $CH_2Cl_2$ (30 ml×3). The extracts combined were dried ($Na_2SO_4$), filtered, and concentrated to give 319.5 mg of crude product, which was purified by silica gel column chromatography ($CH_2Cl_2$/methanol: 30/1) to give 214.9 mg (83%) of ester derivative as yellow oil. To a stirred solution of this oil (214.9 mg, 0.481 mmol) in methanol (2.5 ml) and THF (2.5 ml) was added 2N NaOH (1 ml) at room temperature. After 2 h stirring, the reaction mixture was acidified with 1N HCl (20 ml), extracted with $CH_2Cl_2$ (20 ml×2), dried ($Na_2SO_4$), filtered, and concentrated to give 231.4 mg of crude carboxylic acid. A mixture of this acid derivative (231.4 mg, 0.481 mmol) and polyphospholic acid (4.6 g) was stirred at 100° C. for 1 h. The reaction mixture was quenched with ice water (50 ml), basified with 2N NaOH, and extracted with $CH_2Cl_2$ (30 ml×3). The extracts combined were dried ($Na_2SO_4$), filtered, and concentrated to give 189 mg of crude product, which was purified by silica gel column chromatography ($CH_2Cl_2$/methanol: 20/1) to give 139.1 mg (72%) of title compound as yellow oil.

$^1$H NMR (270 MHz, CDCl$_3$) δ7.89 (1H, dd, J=1.5, 7.9 Hz), 7.44 (1H, br.d, J=7.4 Hz), 7.24–7.14 (4H, m), 7.10 (1H, dd, J=7.4, 7.7 Hz), 4.50 (1H, ddd, J=5.4, 6.9, 13.8 Hz), 4.11 (1H, ddd, J=6.6, 7.6, 14.0 Hz), 3.27–3.12 (1H, m), 2.98–2.72 (9H, m), 2.64–2.51 (1H, m), 2.44–2.30 (1H, m), 2.24–2.10 (1H, m), 2.01 (2H, t, J=7.4 Hz), 1.97–1.80 (2H, m), 1.58–1.48 (2H, m).

This oil (11.4 mg, 0.028 mmol) and citric acid (5.4 mg, 0.028 mmol) was dissolved in methanol (2 ml) and $CH_2Cl_2$ (0.5 ml), and the solution was stirred at room temperature for 1.5 h. The solvent was evaporated and the resulting residue was dissolved in hexane (5 ml) and $CH_2Cl_2$ (0.5 ml). The solvent was evaporated and dried (60° C., 1 d) to give 10.9 mg of citrate salt as white amorphous solid.

MS(ESI positive) m/z : 401.18(M+1)$^+$.

Example 23

6-(2,3-Dihydro-1'H-spiro[indene-1,4'piperidin]-1'-ylmethyl)-1-hydroxy-2,3,6,7-tetrahydro-1H,5H-pyrido[3,2,1-ij]quinolin-5-one To a stirred solution of 6-(2,3-dihydro-1'H-spiro[indene-1,4'piperidin]-1'-ylmethyl)-2,3,6,7-tetrahydro-1H,5H-pyrido[3,2,1-ij]quinolin-1,5-dione (30 mg, 0.075 mmol) in ethanol (3 ml) was added sodium borohydride (7.1 mg, 0.188 mmol) at 0° C. After 10 min stirring, the reaction mixture was diluted with water (20 ml), extracted with $CH_2Cl_2$ (20 ml×3), dried (Na2SO4), filtered, and concentrated to give 32 mg of crude product, which was purified by preparative TLC (silica gel plate, $CH_2Cl_2$/methanol/triethylamine: 200/10/1, 2 developed) to give 9.7 mg (32%) of title compound as colorless oil.

$^1$H NMR (270 MHz, CDCl$_3$) δ 7.33–7.12 (6H, m), 7.06–6.99 (1H, m), 4.88–4.80 (1H, m), 4.41–4.30 (0.7H, m), 4.25–4.13 (0.3H, m), 3.88–3.75 (0.3H, m), 3.72–3.60 (0.7H, m), 3.18–3.05 (0.7H, m), 3.00–2.70 (7.3H, m), 2.63–2.25 (1H, m), 2.25–1.85 (9H, m), 1.58–1.48 (2H, m).

This oil (12 mg, 0.03 mmol) and citric acid (5.8 mg, 0.03 mmol) was dissolved in methanol (1.5 ml) and $CH_2Cl_2$ (0.5 ml), and the solution was stirred at room temperature for 2 h. The solvent was evaporated and the resulting residue was dissolved in hexane (3 ml) and $CH_2Cl_2$ (0.5 ml). The solvent was evaporated and dried (60° C., 1 d) to give 8.6 mg of citrate salt as white amorphous solid.

MS(ESI positive) m/z : 403.22(M+1)$^+$.

Preparation 16

7-Bromo-1-[2-({[tert-butyl(diphenyl)silyl]oxy}methyl)acryloyl]indoline

To a stirred solution of methyl 2-(hydroxymethyl)acrylate (2.00 g, 17.2 mmol, this was prepared according to the reported method by J. I. Borrell et al, *J. Med. Chem.*, 1998, 41, 3539) and tert-butyldiphenylsiliyl chloide (5.20 g, 18.9 mmol) in CH2Cl2 (20 ml) were added triethylamine (2.88 ml, 20.6 mmol) and 4-dimethylaminopyridine (220 mg, 1.7 mmol) at room temperature and the resulting mixture was stirred for 14 h. The reaction mixture was quenched with aqueous solution of NaOCH3, dried (Na2SO4), filtered, concentrated, and purified by silica gel column chromatography (n-hexane/ethyl acetate:20/1) to afford 3.27 g (54%) of TBDPS ether compound as colorless oil.

$^1$H NMR (300 MHz, CDCl$_3$) δ 7.69–7.66 (4H, m), 7.44–7.35 (6H, m), 6.33 (1H, td, J=1.8, 3.7 Hz), 6.12 (1H, td, J=2.0, 4.1 Hz), 4.42 (2H, dd, J=2.0, 2.2 Hz), 3.70 (3H, s), 1.08 (9H, s).

A mixture of this oil (1.10 g, 3.10 mmol), 2N NaOH (4.7 ml, 9.3 mmol), and mixed solvent of THF(8 ml) and methanol (6 ml) was stirred at room temperature for 2.5 h. After evaporation of the solvent, the residue was acidified with 10% citric acid and extracted with $CH_2Cl_2$. The extracts combined were dried ($Na_2SO_4$), filtered, and concentrated to give 1.06 g (crude 100%) of acid derivative as colorless oil. A mixture of this acid derivative (1.40 g, 4.11 mmol) and thionyl chloride (3 ml) was stirred at room temperature for 45 min. After concentaration, the residue was dissolved in toluene and concentrated to give crude acid chloride derivative. To a solution of this acid chloride derivative in $CH_2Cl_2$ (10 ml) was added a solution of 7-bromoindoline (0.45 g, 2.27 mmol, this was prepared according to the reported method by A. I. Meyers et al, *Tet. Lett.*, 1993, 34, 6185) and triethylamine (0.95 ml, 6.8 mmol) in $CH_2Cl_2$ (3 ml) at 0° C. After 1 h stirring at 0° C., the mixture was quenched with aqueous solution of NaOCH$_3$ and extracted with $CH_2Cl_2$. The extracts combined were dried (Na$_2$SO$_4$), filtered, concentrated, and purified by silica gel column chromatography (n-hexane/ethyl acetate:10/1) to afford 894 mg (76%) of title compound as colorless oil.

1H NMR (270 MHz, CDCl$_3$) δ 7.71–7.66 (4H, m), 7.44–7.33 (7H, m), 7.19–7.14 (1H, m), 6.94 (1H, dd, J=7.4, 7.9 Hz), 5.88–5.84 (1H, m), 5.66–5.64 (1H, m), 4.53 (2H, dd, J=1.5, 1.7 Hz), 4.10 (2H, t, J=7.6 Hz), 3.00 (2H, t, J=7.6 Hz), 1.08 (9H, s).

MS (ESI positive) m/z: 520.02 (M+H)$^+$.

Preparation 17
5-(Hydroxymethyl)-1,2-dihydro-4H-pyrrolo[3,2,1-ij]quinolin-4-one

To a stirred solution of 7-bromo-1-[2-({[tert-butyl(diphenyl)silyl]oxy}methyl)acryloyl]indoline (0.78 g, 1.5 mmol) in THF (8 ml) was added a 1 M THF solution of tetrabutylammonium fluoride (2.25 ml, 2.25 mmol) at room temperature. After 1 h stirring, the reaction mixture was quenched with water and extracted with CH$_2$Cl$_2$. The extracts combined were dried (Na$_2$SO$_4$), filtered, concentrated, and purified by silica gel column chromatography (n-hexane/acetone:2/1) to afford 360 mg (85%) of hydroxyl derivative as a white solid. To a stirred solution of this hydroxyl derivative (0.31 g, 1.10 mmol) in acetonitrile (10 ml) were added triethylamine (0.31 ml, 2.2 mmol), tri-o-tolylphosphine (0.13 g, 0.44 mmol), palladium acetate (49 mg, 0.22 mmol) at room temperature. After 20 min reflux, the reaction mixture was cooled, diluted with ethyl acetate, washed with aqueous solution of NaHCO$_3$ and brine, dried (Na$_2$SO$_4$), filtered, concentrated, and purified by preparative TLC (1 mm thick silica gel plate: n-hexane/acetone:1/1) to afford 132 mg (60%) of title compound as a white solid.

$^1$H NMR (270 MHz, CDCl$_3$) δ 7.69 (1H, s), 7.43–7.38 (1H, m), 7.37–7.32 (1H, m), 7.17 (1H, dd, J=7.4, 7.8 Hz), 4.70 (2H, dd, J=0.8, 6.4 Hz), 4.51–4.44 (2H, m), 3.60 (1H, t, J=6.4 Hz), 3.50–3.42 (2H, m).

Example 24
5-(1'H,3H-spiro[2-benzofuran-1,4'piperidin]-1'-ylmethyl)-1,2,5,6-tetrahydro-4H-pyrrolo[3,2,1-ij]quinolin-4-one To a stirred solution of 5-(hydroxymethyl)-1,2-dihydro-4H-pyrrolo[3,2,1-ij]quinolin-4-one (80 mg, 0.398 mmol) and triethylamine (0.11 ml, 0.796 mmol) in CH$_2$Cl$_2$ (10 ml) was added methanesulfonyl chloride (54.8 mg, 0.478 mmol) at 0° C. After 0.5 h stirring at 0° C., the reaction mixture was quenched with aqueous solution of NaHCO$_3$ (20 ml), and extracted with CH$_2$Cl$_2$. The extracts combined were dried (Na$_2$SO$_4$), filtered, concentrated to give 111.7 mg of crude mesylate as yellow solid. A mixture of this crude mesylate (111.4 mg, 0.398 mmol), 3H-spiro[2-benzofuran-1,4'-piperidine] hydrochloride (89.8 mg, 0.398 mmol), and diisopropylethylamine (0.21 ml, 1.194 mmol) in THF (10 ml) was refluxed for 16 h. After cooling down, the reaction mixture was quenched with aqueous solution of NaHCO$_3$ (15 ml), and extracted with CH$_2$Cl$_2$ (15 ml×3). The extracts combined were dried (Na$_2$SO$_4$), filtered, and concentrated to give 190.6 mg of crude product, which was purified by silica gel column chromatography (CH$_2$Cl$_2$/methanol: 20/1) to give 108.4 mg (73%) of coupling product as yellow oil.

$^1$H NMR (270 MHz, CDCl$_3$) δ 7.86 (1H, s), 7.44–7.10 (7H, m), 5.07 (2H, s), 4.51–4.44 (2H, m), 3.72 (2H, s), 3.48–3.38 (2H, m), 3.02–2.90 (2H, m), 2.72–2.55 (2H, m), 2.18–2.00 (2H, m), 1.86–1.74 (2H, m).

To a stirred solution of this coupling product (108.4 mg, 0.291 mmol) in toluene (3.2 ml) was added a 1M solution of L-selectride in THF(0.87 ml, 0.87 mmol) at −78° C. After 4.5 h stirring at −50° C., the reaction mixture was quenched with aqueous solution of NaHCO$_3$ (15 ml), and extracted with CH$_2$Cl$_2$ (15 ml×3). The extracts combined were dried (Na$_2$SO$_4$), filtered, and concentrated to give 190.6 mg of crude product, which was purified by preparative TLC (1 mm thick silica gel plate: n-hexane/acetone/triethylamine:30/10/1, then n-hexane/acetone/triethylamine:30/10/1 3 developed, then n-hexane/acetone/triethylamine:20/10/1) to afford 26 mg (24%) of title compound.

$^1$H NMR (270 MHz, CDCl$_3$) δ 7.32–7.01 (6H, m), 6.93 (1H, dd, J=7.4, 7.4 Hz), 5.06 (2H, s), 4.13–4.02 (2H, m), 3.25–3.15 (2H, m), 3.14–2.35 (9H, m), 2.08–1.69 (4H, m). This compound (26 mg, 0.069 mmol) and citric acid (13.3 mg, 0.069 mmol) was dissolved in methanol (2 ml) and CH$_2$Cl$_2$ (0.5 ml), and the solution was stirred at room temperature for 3 h. The solvent was evaporated and the resulting residue was dissolved in hexane (5 ml) and CH$_2$Cl$_2$ (0.5 ml). The solvent was evaporated to give white solid which was washed with ether and dried (50° C.) to give 30 mg of citrate salt as pale yellow amorphous solid.

MS(ESI positive) m/z: 375.16(M+1)$^+$.

IR(KBr): 3420, 1742, 1660, 1634, 1595, 1487, 1412, 1196, 764 cm$^{-1}$

Anal. Calcd for C$_{24}$H$_{26}$N$_2$O$_2$—C$_6$H$_8$O$_7$·4H$_2$O: C, 59.79; H, 6.36; N, 4.65. Found: C, 59.71; H, 6.29; N, 4.36.

Preparation 18
3-(Hydroxymethyl)-8-methoxyquinolin-2(1H)-one

A mixture of diethyl malonate (34.5 g, 215 mmol), 3-methoxy-2-nitrobenzaldehyde (19.50 g, 108 mmol), and piperidine (1.40 g, 16 mmol) in pyridine (150 ml) was refluxed with stirring for 18 h. After cooling down to room temperature, the reaction mixture was concentrated, diluted with ethyl acetate (200 ml), washed with 2N HCl, saturated NaHCO$_3$ solution (300 ml), and brine, dried (MgSO$_4$), filtered, and concentrated. Resulting crude product was purified by silica gel column chromatography (n-hexane/ethyl acetate: 3/1 then 7/3) to give 12.64 g (36%) of diethyl (3-methoxy-2-nitrobenzylidene)malonate as brown color oil.

$^1$H NMR (270 MHz, CDCl$_3$) δ 7.65 (1H, s), 7.42 (1H, dd, J=7.9, 8.4 Hz ), 7.12–7.03 (2H, m), 4.30 (2H, q, J=7.5 Hz), 4.21 (2H, q, J=7.3 Hz), 3.93 (3H, s), 1.33 (3H, t, J=7.6Hz), 1.18 (3H, t, J=7.1Hz).

To a stirred solution of diethyl (3-methoxy-2-nitrobenzylidene)malonate (14.17 g, 43.8 mmol) in acetic acid (200 ml) was added Fe powder (14.7 g, 263 mmol) at room temperature. Then the reaction mixture was stirred at 80° C. under nitrogen atmosphere for 7 h. After Celite filtration, the filtrate was concentrated, diluted with CH$_2$Cl$_2$, washed with saturated NaHCO$_3$ and brine, dried (MgSO$_4$), filtered, and concentrated. Resulting crude product was purified by silica gel column chromatography (CH$_2$Cl$_2$/methanol: 30/1) to give 6.80 g (63%) of ethyl 8-methoxy-2-oxo-1,2-dihydroquinoline-3-carboxylate.

$^1$H NMR (270 MHz, CDCl$_3$) δ 9.42 (1H, br.s), 8.49, (1H, s), 7.28–7.02 (3H, m), 4.43 (2H, q, J=7.1 Hz), 3.99 (3H, s), 1.42 (3H, t, J=7.1Hz).

To a stirred solution of ethyl 8-methoxy-2-oxo-1,2-dihydroquinoline-3-carboxylate (4.00 g, 16.2 mmol) in THF (100 ml) was dropwisely added a 1.0 M toluene solution of DIBAL (40.5 ml, 40.5 mmol) at −78° C. and resulting mixture was stirred at −78° C. to −30° C. for 3 h. The reaction mixture was quenched with 2N HCl (150 ml), then warmed to room temperature, and stirred for 20 min. The reaction mixture was concentrated, diluted with 2N HCl and ethyl acetate. The organic layer was separated and aqueous layer was extracted with ethyl acetate. The extracts and organic layer were cobined, dried (MgSO$_4$), filtered, and concentrated to give 1.50 g of crude product. Aqueous layer was extracted again with CH$_2$Cl$_2$ for 4 times. The extracts combined were dried (MgSO$_4$), filtered, and concentrated. Combined crude product solidified was washed with CH$_2$Cl$_2$, collected by filtration to give 1.38 g (41%) of title compound as pale brown solid. The filtrate was concentrated and purified by silica gel column chromatography (CH$_2$Cl$_2$/methanol: 20/1) to give 1.24 g (37%) of title compound as white solid.

$^1$H NMR (270 MHz, DMSO-d6) δ 9.27 (1H, br.s), 7.72 (1H, s ), 7.20–7.12 (2H, m), 7.02–6.94 (1H, m), 4.69 (2H, d, J=6.3 Hz), 3.99 (3H, s), 3.36 (1H, t, J=6.2 Hz), 1.60 (1H, s).

Preparation 19
3-(2,3-Dihydroxy-1'H-spiro[indene-1,4'-piperidin]-1'-ylmethyl)-8-methoxyquinolin-2(1H)-one To a stirred suspension of 3-(hydroxymethyl)-8-methoxyquinolin-2(1H)-one (2.12 g, 10.3 mmol) and triethylamine (2.15 ml, 15.5 mmol) in CH$_2$Cl$_2$ (80 ml) was added methanesulfonyl chloride (1.12 ml, 14.5 mmol) at 0° C. and the resulting reaction mixture was stirred at 0° C. for 60 min. The reaction mixture was quenched with saturated aqueous NaHCO$_3$ solution and extracted with CH$_2$Cl$_2$. The extracts combined were dried (MgSO$_4$), filtered, and concentrated to give 3.00 g of crude mesylate.

$^1$H NMR (270 MHz, CDCl$_3$) δ9.22 (1H, br.s), 7.93 (1H, t, J=0.9 Hz), 7.21 (1H, dd, J=2.0, 8.1 Hz), 7.18 (1H, dd, J=7.0, 8.1 Hz), 7.02 (1H, dd, J=2.0, 7.1 Hz), 5.27 (2H, d, J=1.1 Hz), 4.00 (3H, s), 3.15 (3H, s).

A mixture of this mesylate (3.00 g, 10.3 mmol), 2,3-dihydrospiro[1H-indene-1,4'-piperidine]hydrochloride (3.69 g, 16.5 mmol) and N,N-diisopropylethylamine (5.4 ml, 30.9 mmol) in THF (100 ml) was refluxed with stirring for 18 h. The reaction mixture was quenched with saturated aqueous NaHCO$_3$ solution and extracted with ethyl acetate. The extracts combined were washed with brine, dried (MgSO$_4$), filtered, and concentrated. The residue was purified by silica gel column chromatography (CH$_2$Cl$_2$/methanol: 30/1) to give 2.83 g (73%) of title compound as white solid.

$^1$H NMR (270 MHz, CDCl$_3$) δ 9.14 (1H, br.s), 7.90 (1H, s), 7.28–7.11 (6H, m), 6.98–6.93 (1H, m), 3.98 (3H, s), 3.63 (2H, s), 3.00–2.87 (4H, m), 2.44–2.32 (2H, m), 2.09–1.96 (4H, m), 1.62–1.53 (2H, m).

Example 25
3-(2,3-Dihydro-1'H-spiro[indene-1,4'piperidin]-1'-ylmethyl)-8-methoxy-1-methyl-3,4- dihydroquinolin-2(1H)-one To a stirred solution of 3-(2,3-dihydroxy-1'H-spiro[indene-1,4'-piperidin]-1'-ylmethyl)-8-methoxyquinolin-2(1H)-one (0.30 g, 0.80 mmol) in DMF (6 ml) was added sodium hydride (60% oil suspension, 48 mg, 1.2 mmol) and iodomethane (75 μl, 1.2 mmol) at 0° C. After 1 h stirring at room temperature, the reaction mixture was quenched with aqueous solution of NaHCO$_3$ and extracted with ethyl acetate. The extracts combined were washed with water and brine, dried (MgSO$_4$), filtered, and concentrated. Resulting crude product was purified by silica gel column chromatography (CH$_2$Cl$_2$/methanol: 30/1) to give 118 mg (38%) of N-methyl derivative as colorless amorphous solid.

$^1$H NMR (270 MHz, CDCl$_3$) δ 7.79 (1H, s), 7.28–7.11 (6H, m), 7.03 (1H, dd, J=1.7, 7.7 Hz), 4.01 (3H, s), 3.90 (3H, s), 3.64 (2H, s), 3.00–2.85 (4H, m), 2.42–2.32 (2H, m), 2.10–1.97 (4H, m), 1.62–1.52 (2H, m).

To a stirred solution of N-methyl derivative (220 mg, 0.566 mmol) in toluene (6 ml) was added a 1.0 M THF solution of L-selectride (1.7 ml, 1.7 mmol) at −78° C. After 2 h stirring at −78° C. to −30° C., the reaction mixture was quenched with aqueous solution of NaHCO$_3$ and extracted with CH$_2$Cl$_2$. The extracts combined were dried (MgSO$_4$), filtered, and concentrated. Resulting crude product was purified by silica gel column chromatography (CH$_2$Cl$_2$/methanol: 20/1) to give 169 mg (77%) of title compound as pale yellow amorphous solid.

$^1$H NMR (270 MHz, CDCl$_3$) δ 7.05–7.02 (4H, m), 7.02 (1H, dd, J=7.8, 7.8 Hz), 6.85 (2H, d, J=7.9 Hz), 3.84 (3H, s), 3.39 (3H, s), 3.10–2.65 (8H, m), 2.60–2.30 (2H, m), 2.20–2.10 (1H, m), 2.05–1.85 (5H, m), 1.60–1.45 (2H, m).

This compound (9 mg, 0.023 mmol) and citric acid (4.4 mg, 0.023 mmol) was dissolved in methanol (1 ml) and CH$_2$Cl$_2$ (1 ml), and the solution was stirred at room temperature for 3 h. The solvent was evaporated and the resulting residue was dissolved in hexane (5 ml) and CH$_2$Cl$_2$ (0.5 ml). The solvent was evaporated to give white solid which was washed with ether and dried (50° C.) to give 10.9 mg of citrate salt as white amorphous solid.

MS(ESI positive) m/z: 391.20(M+)$^+$.

Example 26
3-(2,3-Dihydro-1'H-spiro[indene-1,4'piperidin]-1'-ylmethyl)-8-hydroxy-1-methyl-3,4-dihydroquinolin-2(1H)-one To a stirred solution of 3-(2,3-dihydro-1'H-spiro[indene-1,4'piperidin]-1'-ylmethyl)-8-methoxy-1-methyl-3,4-dihydroquinolin-2(1H)-one (169 mg, 0.433 mmol) in CH$_2$Cl$_2$ (4 ml) was added a 1 M CH$_2$Cl$_2$ solution of BBr3 (1.73 ml, 1.73 mmol) at 0° C. After 1 h stirring at 0° C. and 30 min stirring at room temperature, the reaction mixture was quenched with aqueous solution of NaHCO$_3$ and extracted with CH$_2$Cl$_2$. The extracts combined were dried (MgSO$_4$), filtered, and concentrated. The crude product was purified by silica gel column chromatography (CH$_2$Cl2/methanol: 30/1) to give 127 mg (78%) of title compound as pale brown amorphous solid.

$^1$H NMR (270 MHz, CDCl$_3$) δ 7.25–7.07 (4H, m), 6.94–6.68 (3H, m), 5.29 (1H, s), 3.44 (3H, s), 3.07–2.65 (8H, m), 2.55–2.12 (3H, m), 2.05–1.85 (4H, m), 1.58–1.45 (2H, m).

This compound (127 mg, 0.337 mmol) and citric acid (65 mg, 0.337 mmol) was dissolved in methanol (2 ml) and CH$_2$Cl$_2$ (2 ml), and the solution was stirred at room temperature for 3 h. The solvent was evaporated and the resulting residue was dissolved in hexane (5 ml) and CH$_2$Cl$_2$ (0.5 ml). The solvent was evaporated to give white solid which was washed with ether and dried (50° C.) to give 173 mg of citrate salt as white amorphous solid.

MS(ESI positive) m/z: 377.16(M+1)$^+$.

IR(KBr): 1728, 1641, 1612, 1593, 1479, 1427, 1367, 1282, 1207, 764 cm$^{-1}$

Anal. Calcd for $C_{24}H_{28}N_2O_2$—$C_6H_8O_7$-$2H_2O$-0.35CH2Cl2: C, 57.46; H, 6.47;N, 4.42. Found: C, 59.95; H, 6.23; N, 4.25.

Example 27
3-(2,3-Dihydro-1'H-spiro[indene-1,4'piperidin]-1'-ylmethyl)-8-methoxy-3,4-dihydroquinolin-2(1H)-one To a stirred solution of 3-(2,3-dihydroxy-1'H-spiro[indene-1,4'-piperidin]-1'-ylmethyl)-8-methoxyquinolin-2(1H)- one (0.50 g, 1.34 mmol) in DMF (5 ml) was added sodium hydride (60% oil suspension, 59 mg, 1.47 mmol) at 0° C. After 0.5 h stirring at 0° C., benzyl bromide (175 μl, 1.47 mmol) was added to the reaction mixture at 0° C. After 20 min stirring at 0° C. followed by 1 h stirring at room temperature, the reaction mixture was quenched with aqueous solution of NaHCO$_3$ and extracted with ethyl acetate. The extracts combined were washed with water and brine, dried (MgSO$_4$), filtered, and concentrated. Resulting crude product was purified by silica gel column chromatography (n-hexane/ethyl acetate: 1/1, then 1/4) to give 328 mg (53%) of N-benzyl derivative as colorless amorphous solid.

$^1$H NMR (270 MHz, CDCl$_3$) δ 7.85 (1H, s), 7.29–7.08 (11H, m), 6.93 (1H, dd, J=1.5, 7.9 Hz), 5.93 (2H, s), 3.66 (2H, d, J=0.8 Hz), 3.56 (3H, s), 3.02–2.85 (4H, m), 2.44–2.32 (2H, m), 2.10–1.98 (4H, m), 1.62–1.52 (2H, m).

To a stirred solution of N-benzyl derivative (314 mg, 0.676 mmol) in toluene (8 ml) was added a 1.0 M THF solution of L-selectride (2 ml, 2 mmol) at –78° C. After 3 h stirring at –78° C. to –40° C., the reaction mixture was quenched with aqueous solution of NaHCO$_3$ and extracted with ethyl acetate. The extracts combined were dried (MgSO$_4$), filtered, and concentrated. Resulting crude product was purified by silica gel column chromatography (CH$_2$Cl$_2$/methanol: 50/1) to give 300 mg (95%) of tetrahydroquinolin-2-one compound as pale yellow amorphous solid.

$^1$H NMR (270 MHz, CDCl$_3$) δ 7.25–7.10 (10H, m), 6.99 (1H, dd, J=7.6, 8.1 Hz), 6.85–6.73 (2H, m), 5.42 (1H, d, J=15.3 Hz), 5.21 (1H, d, J=15.0 Hz), 3.71 (3H, s), 3.08 (1H, dd, J=4.1, 14.7 Hz), 3.00–2.50 (7H, m), 2.50–1.85 (5H, m), 1.60–1.48 (2H, m).

To a stirred dark blue solution prepared from liquid ammonia and sodium was added a solution of tetrahydroquinolin-2-one derivative (180 mg, 0.39 mmol) in THF (2 ml) at –78° C. After 30 min stirring at –78° C., the reaction mixture was quenched with NH$_4$Cl and warmed to room temperature. The residue was dissolved in aqueous solution of NaHCO$_3$, extracted with CH$_2$Cl$_2$. The extracts combined were dried (MgSO$_4$), filtered, and concentrated. Resulting crude product was purified by silica gel column chromatography (CH$_2$Cl$_2$/methanol: 30/1) to give 110 mg (53%) of title compound.

$^1$H NMR (300 MHz, CDCl$_3$) δ 7.79 (1H, br.s), 7.24–7.12 (4H, m), 6.95 (1H, dd, J=7.7, 8.0 Hz), 6.86–6.74 (2H, m), 3.86 (3H, s), 3.15 (1H, dd, J=5.9, 15.8 Hz), 2.98–2.73 (6H, m), 2.56 (1H, dd, J=8.8, 11.7 Hz), 2.40–2.30 (1H, m), 2.20–2.10 (1H, m), 2.03–1.84 (4H, m), 1.57–1.48 (2H, m).

This compound (30 mg, 0.08 mmol) and citric acid (15 mg, 0.08 mmol) was dissolved in methanol (2 ml) and CH$_2$Cl$_2$ (2 ml), and the solution was stirred at room temperature for 3 h. The solvent was evaporated and the resulting residue was dissolved in hexane (5 ml) and CH$_2$Cl$_2$ (0.5 ml). The solvent was evaporated to give white solid which was washed with ether and dried (50° C.) to give 38 mg of citrate salt as white amorphous solid.

MS(ESI positive) m/z: 377.20(M+1)$^+$.

IR(KBr): 3408, 1720, 1674, 1597, 1501, 1414, 1265, 1082, 764 cm$^{-1}$

Anal. Calcd for C$_{24}$H$_{28}$N$_2$O$_2$—C$_6$H$_8$O$_7$-1.5H$_2$O-0.2CH$_2$Cl$_2$: C, 59.21; H, 6.48; N, 4.57, Found: C, 59.00; H, 6.22; N, 4.19.

Example 28

3-(2,3-Dihydro-1'H-spiro[indene-1,4'piperidin]-1'-ylmethyl)-8-methoxy-3,4-dihydroquinolin-2(1H)-one To a stirred solution of 3-(2,3-dihydro-1'H-spiro[indene-1,4'piperidin]-1'-ylmethyl)-8-methoxy-3,4-dihydroquinolin-2(1H)-one (80 mg, 0.21 mmol) in CH$_2$Cl$_2$ (3 ml) was added a 1 M CH$_2$Cl$_2$ solution of BBr$_3$ (0.85 ml, 0.85 mmol) at 0° C. After 1 h stirring at 0°, the reaction mixture was diluted with CH$_2$Cl$_2$ (5 ml) and warmed to room temperature. After 3 h stirring, the reaction mixture was quenched with aqueous solution of NaHCO$_3$ and extracted with CH$_2$Cl$_2$. The extracts combined were dried (MgSO$_4$), filtered, and concentrated. The crude product was purified by silica gel column chromatography (CH$_2$Cl$_2$/methanol: 10/1) to give 38 mg (50%) of title compound as pale yellow amorphous solid.

$^1$H NMR (270 MHz, CDCl$_3$) δ 8.36 (1H, br.s), 7.22–7.07 (4H, m), 6.90–6.69 (3H, m), 3.18–2.80 (8H, m), 2.58–2.48 (1H, m), 2.42–2.18 (2H, m), 2.10–1.85 (4H, m), 1.60–1.45 (2H, m).

This compound (38 mg, 0.105 mmol) and citric acid (20 mg, 0.105 mmol) was dissolved in methanol (2 ml) and CH$_2$Cl$_2$ (2 ml), and the solution was stirred at room temperature for 3 h. The solvent was evaporated and the resulting residue was dissolved in hexane (5 ml) and CH$_2$Cl$_2$ (0.5 ml). The solvent was evaporated to give white solid which was washed with ether and dried (50° C.) to give 50 mg of citrate salt as pale brown amorphous solid.

MS(ESI positive) m/z: 363.19(M+1)$^+$.

IR(KBr): 1719, 1666, 1599, 1479, 1390, 1277, 764 cm$^{-1}$

Anal. Calcd for C$_{23}$H$_{26}$N$_2$O$_2$—C$_6$H$_8$O$_7$—H$_2$O-0.45CH$_2$Cl$_2$: C, 57.91; H, 6.09; N, 4.59. Found: C, 58.28; H, 5.78; N, 4.45.

Example 29

3-(2,3-Dihydroxy-1'H-spiro[indene-1,4'-piperidin]-1'-ylmethyl)-6-fluoro-1-methyl-3,4-dihydroquinolin-2(1H)-one To a stirred suspension of 3-(hydroxymethyl)-6-fluoroquinolin-2(1H)-one (110 mg, 0.57 mmol,. this was prepared according to the reported method by A. Claesson et al, *Bioorg. Med. Chem. Lett.*, 1996, 6, 1635) and triethylamine (119 μl, 0.86 mmol) in CH$_2$Cl$_2$ (8 ml) was added methanesulfonyl chloride (62 μl, 0.8 mmol) at 0° C. and the resulting reaction mixture was stirred at 0° C. for 20 min. The reaction mixture was warmed to room temperature and THF (4 ml) and DMF (4 ml) was added to the reaction mixture and stirred for 30 min. To a stirred solution of this reaction mixture was added triethylamine (119 μl, 0.86 mmol) and methanesulfonyl chloride (62 μl, 0.8 mmol) and stirred for 30 min. The reaction mixture was quenched with saturated aqueous NaHCO$_3$ solution and extracted with CH$_2$Cl$_2$. The extracts combined were dried (MgSO$_4$), filtered, and concentrated to give crude mesylate.

A mixture of this mesylate, 2,3-dihydrospiro[1H-indene-1, 4'-piperidine]hydrochloride (204 mg, 0.91 mmol) and N,N-diisopropylethylamine (0.3 ml, 1.71 mmol) in THF was refluxed with stirring for 16 h. The reaction mixture was quenched with aqueous NaHCO$_3$ solution and extracted with CH$_2$Cl$_2$. The extracts combined were washed with water, dried (MgSO$_4$), filtered, and concentrated. The residue was purified by silica gel column chromatography (n-hexane/acetone: 1/1) to give 38 mg, which was purified again by preparative TLC (CH$_2$Cl$_2$/methanol: 20:1, then 10/1) to give 28 mg (14%) of coupling product as yellow solid.

$^1$H NMR (300 MHz, CDCl$_3$) δ 2.31 (1H, br.s), 8.00 (1H, br.s), 7.54–7.14 (7H, m), 3.98 (3H, s), 3.74 (2H, br.s), 3.10–2.88 (4H, m), 2.56–2.38 (2H, m), 2.16–2.02 (4H, m), 1.66–1.54 (2H, m).

To a stirred solution of 3-(2,3-dihydroxy-1'H-spiro[indene-1,4'-piperidin]-1'-ylmethyl)-6-fluoroquinolin-2(1H)-one (27 mg, 0.074 mmol) in DMF (1 ml) was added sodium hydride (60% oil suspension, 3.3 mg, 0.082 mmol) and iodomethane (5.1 μl, 0.082 mmol) at room temperature. After 0.5 h stirring at room temperature, the reaction mixture was quenched with aqueous solution of NaHCO$_3$ and extracted with ethyl acetate. The extracts combined were washed with water and brine, dried (MgSO$_4$), filtered, and concentrated. Resulting crude product was purified by preparative TLC (CH$_2$Cl$_2$/methanol: 20:1) to give 20 mg (72%) of N-methyl derivative as pale yellow oil.

$^1$H NMR (270 MHz, CDCl$_3$) δ 8.02 (1H, s), 7.36–7.13 (7H, m), 3.76 (3H, s), 3.63 (2H, br.d, J=1.0 Hz), 3.00–2.87 (4H, m), 2.46–2.32 (2H, m), 2.10–1.97 (4H, m), 1.64–1.53 (2H, m).

To a stirred solution of N-methyl derivative (20 mg, 0.053 mmol) in toluene (2 ml) was added a 1.0 M THF solution of L-selectride (0.16 ml, 0.16 mmol) at −78° C. After 3 h stirring at −78° C. to −30° C., the reaction mixture was quenched with aqueous solution of NaHCO$_3$ and extracted with CH$_2$Cl$_2$. The extracts combined were dried (MgSO$_4$), filtered, and concentrated. Resulting crude product was purified by preparative TLC (CH$_2$Cl$_2$/methanol: 20:1) to give 15 mg (75%) of title compound as pale brown oil.

$^1$H NMR (270 MHz, CDCl$_3$) δ 7.25–7.13 (4H, m), 7.00–6.86 (3H, m), 3.35 (3H, s), 3.14–3.06 (1H, m), 2.94–2.68 (7H, m), 2.58–2.30 (2H, m), 2.20–2.08 (1H, m), 2.04–1.82 (5H, m), 1.58–1.46 (2H, m).

This compound (15 mg, 0.040 mmol) and citric acid (7.6 mg, 0.040 mmol) was dissolved in methanol (1 ml) and CH$_2$Cl$_2$ (1 ml), and the solution was stirred at room temperature for 3 h. The solvent was evaporated and the resulting residue was dissolved in hexane (5 ml) and CH$_2$Cl$_2$ (0.5 ml). The solvent was evaporated to give white solid which was washed with ether and dried (50° C.) to give 15 mg of citrate salt as pale brown amorphous solid.

MS(ESI positive) m/z: 379.15 (M+1)$^+$.

IR(KBr): 3410, 1728, 1663, 1506, 1477, 1377, 1240, 1161, 762 cm$^{-1}$

Example 30
8-Hydroxy-1-methyl-3-(1'H-spiro[indene-1,4'-piperidin]-1'-ylmethyl)-3,4-dihydroquinolin-2(1H)-one To a stirred suspension of 3-(hydroxymethyl)-8-methoxyquinolin-2(1H)-one (400 mg, 1.949 mmol, this was prepared in Preparation 18) and triethylamine (408 μl, 2.924 mmol) in CH$_2$Cl$_2$ (15 ml) was added methanesulfonyl chloride (211 μl, 2.729 mmol) at 0° C. and the resulting reaction mixture was stirred at 0° C. for 1 h. The reaction mixture was quenched with saturated aqueous NaHCO$_3$ solution and extracted with CH$_2$Cl$_2$. The extracts combined were dried (Na$_2$SO$_4$), filtered, and concentrated to give 0.5774 g of crude mesylate as a white solid.

A mixture of this mesylate, spiro[indene-1,4'-piperidine] hydrochloride (691.5 mg, 3.119 mmol) and N,N-diisopropylethylamine (0.019 ml, 5.848 mmol) in THF (30 ml) was refluxed with stirring for 20 h. The reaction mixture was cooled down, quenched with aqueous NaHCO$_3$ solution, and extracted with CH$_2$Cl$_2$. The extracts combined were washed with water, dried (Na$_2$SO$_4$), filtered, and concentrated. The residue was purified by silica gel column chromatography (n-hexane/acetone: 1/1, then CH$_2$Cl$_2$/methanol: 10/1) to give 550 mg (75.8%) of coupling product as white solid.

$^1$H NMR (300 MHz, CDCl$_3$) δ 9.16 (1H, br.s), 7.93 (1H, s), 7.46–7.40 (1H, m), 7.35–7.28 (1H, m), 7.28–7.20 (1H, m), 7.15 (1H, dd, J=7.9, 7.9 Hz), 6.96 (1H, dd, J=1.3, 7.9 Hz), 6.90 (1H, d, J=5.8 Hz), 6.75 (1H, d, J=5.8 Hz), 3.98 (3H, s), 3.71 (2H, d, J=1.2 Hz), 3.08 (2H, br.d, J=11.9 Hz), 2.55 (2H, dt, J=2.5, 12.0 Hz), 2.27 (2H, dt, J=3.6, 13.2Hz), 1.39 (2H, d, J=13.2Hz).

To a stirred solution of the above coupling product (550 mg, 1.477 mmol) in DMF (12 ml) was added sodium hydride (60% oil suspension, 88.6 mg, 2.216 mmol) at 0° C. After 0.5 h stirring iodomethane (138 μl, 2.216 mmol) was added to the reaction mixture at 0° C. After 1.5 h stirring at room temperature, the reaction mixture was quenched with aqueous solution of NaHCO$_3$ and extracted with CH$_2$Cl$_2$. The extracts combined were dried (Na$_2$SO$_4$), filtered, and concentrated. Resulting crude product was purified by silica gel column chromatography (CH$_2$Cl$_2$/methanol: 20/1 then 10/1) to give 541.3 mg (75.8%) of N-methyl product as yellow sirup. This was purified again by silica gel column chromatography (CH2Cl$_2$/methanol: 30/1) to give 339.7 mg (59.5%) of N-methyl product as yellow sirup.

$^1$H NMR (300 MHz, CDCl$_3$) δ 7.87 (1H, br.s), 7.47–7.40 (1H, m), 7.35–7.27 (1H, m), 7.27–7.13 (4H, m), 7.05 (1H, dd, J=1.7, 7.8 Hz), 6.90 (1H, d, J=5.6 Hz), 6.75 (1H, d, J=5.6 Hz), 4.02 (3H, s), 3.91 (3H, s), 3.76 (2H, s), 3.12 (2H, d, J=11.5 Hz), 2.61 (2H, t, J=11.0 Hz), 2.32 (2H, t, J=9.9 Hz), 1.40 (2H, d, J=13.2 Hz).

To a stirred solution of the above N-methyl derivative (288.2 mg, 0.7457 mmol) in toluene (8 ml) was added a 1.0 M THF solution of L-selectride (2.24 ml, 2.24 mmol) at −78° C. After 3 h stirring at −78° C. to −30° C., the reaction mixture was quenched with aqueous solution of NaHCO$_3$ and extracted with CH$_2$Cl$_2$. The extracts combined were dried (Na$_2$SO$_4$), filtered, and concentrated. Resulting crude product was purified by silica gel column chromatography (CH$_2$Cl$_2$/methanol: 20/1) followed by NH-silica gel column chromatography (n-hexane/ethyl acetate: 10/1 to 5/1) to give 212.5 mg (73.4%) of N-methyl product as colorless form.

$^1$H NMR (270 MHz, CDCl$_3$) δ 7.42–7.16 (4H, m), 7.04 (1H, t, J=7.9 Hz), 6.90–6.82 (3H, m), 6.72 (1H, d, J=5.8 Hz), 3.85 (3H, s), 3.41 (3H, s), 3.07 (1H, d, J=10.4 Hz), 3.02–2.65 (5H, m), 2.60–2.45 (2H, m), 2.35–2.05 (3H, m), 1.32 (2H, d, J=13.0 Hz).

To a stirred solution of the above 8-methoxy-1-methyl-3-(1'H-spiro[indene-1,4'piperidin]-1'-ylmethyl)-3,4-dihydroquinolin-2(1H)-one (212.5 mg, 0.547 mmol) in CH$_2$Cl$_2$ (5 ml) was added a 1 M CH$_2$Cl$_2$ solution of BBr$_3$ (2.19 ml, 2.19 mmol) at 0° C. After 1 h stirring at 0° then 1 h stirring at room temperature, the reaction mixture was quenched with aqueous solution of NaHCO$_3$ and extracted with CH$_2$Cl$_2$. The extracts combined were dried (Na$_2$SO$_4$), filtered, and concentrated. The crude product was purified by silica gel column chromatography (CH$_2$Cl$_2$/methanol: 20/1) followed by preparative TLC (CH$_2$Cl$_2$/methanol: 10/1, 2 developed) to give 22.1 mg (10.4%) of title compound as pale yellow amorphous solid.

$^1$H NMR (300 MHz, CDCl$_3$) δ 7.35–7.13 (4H, m), 6.91 (1H, t, J=8.1 Hz), 6.87–6.70 (4H, m), 3.45 (3H, s), 3.10–2.95 (4H, m), 2.90–2.68 (2H, m), 2.64–2.47 (2H, m), 2.44–2.10 (3H, m), 1.40–1.25 (2H, m).

This compound (22.1 mg, 0.059 mmol) and citric acid (11.3 mg, 0.059 mmol) was dissolved in methanol (2 ml) and CH$_2$Cl$_2$ (2 ml), and the solution was stirred at room temperature for 1 h. The solvent was evaporated and the resulting residue was dissolved in CH$_2$Cl$_2$ (2 ml) and methanol (3 drops). To this solution was added ether and the precipitated solid was collected, washed with ether and dried (50° C. for 3 h) to give 19.6 mg of citrate salt as white amorphous solid.

MS(ESI positive) m/z: 375.20 (M+1)$^+$.

IR(KBr): 1728, 1645, 1612, 1593, 1427, 1375, 1281, 1215, 1130, 785 cm$^{-1}$

Anal. Calcd for $C_{24}H_{26}N_2O_2$—$C_6H_8O_7$·$4H_2O$: C, 59.79; H, 6.36; N, 4.65. Found: C, 59.44; H, 6.30; N, 4.25.

Preparation 20

8-Methoxy-3-[(1-methyl-1,2-dihydro-1'H-spiro[indole-3,4'-piperidin]-1'-yl)methyl]-quinolin-2(1H)-one To a stirred suspension of 3-(hydroxymethyl)-8-methoxyquinolin-2(1H)-one (400 mg, 1.949 mmol, this was prepared in Preaparation 18) and triethylamine (0.408 ml, 2.924 mmol) in $CH_2Cl_2$ (15 ml) was added methanesulfonyl chloride (0.211 ml, 2.729 mmol) at 0° C. and the resulting reaction mixture was stirred at 0° C. for 60 min. The reaction mixture was quenched with saturated aqueous $NaHCO_3$ solution and extracted with $CH_2Cl_2$. The extracts combined were dried ($Na_2SO_4$), filtered, and concentrated to give 0.8075 g of crude mesylate.

A mixture of this mesylate (0.8075 g), 1-methyl-1,2-dihydrospiro[indole-3,4'-piperidine] (0.473 g, 2.339 mmol) and N,N-diisopropylethylamine (0.679 ml, 3.898 mmol) in THF (30 ml) was refluxed with stirring for 2 days. The reaction mixture was cooled down and concentrated. The residue was purified by silica gel column chromatography ($CH_2Cl_2$/methanol: 20/1) to give 0.5030 g (66.3%) of title compound.

$^1$H NMR (270 MHz, $CDCl_3$) δ 9.17 (1H, br.s), 7.90 (1H, s), 7.24–7.06 (4H, m), 6.95 (1H, dd, J=1.1, 7.7 Hz), 6.71 (1H, dd, J=0.9, 7.3 Hz), 6.48 (1H, dd, J=0.9, 7.5 Hz), 3.98 (3H, s), 3.62 (2H, s), 3.23 (3H, s), 2.96 (2H, br.d, J=11.9 Hz), 2.77 (3H, s), 2.31 (2H, br.t, J=10.1 Hz), 2.02 (2H, dt, J=3.7, 13.2 Hz), 1.76 (2H, d, J=12.7 Hz).

Example 31

8-Hydroxy-3-[(1-methyl-1,2-dihydro-1'H-spiro[indole-3,4'-piperidin]-1'-yl)methyl]-3,4-dihydroquinolin-2(1H)-one This was prepared according to the procedure descrived in Example 27 using 8-methoxy-3-[(1-methyl-1,2-dihydro-1'H-spiro[indole-3,4'-piperidin]-1'-yl)methyl]-quinolin-2(1H)-one instead of 3-(2,3-dihydro-1'H-spiro[indene-1,4'piperidin]-1'-ylmethyl)-8-methoxy-3,4-dihydroquinolin-2(1H)-one. Three steps total yield was 31.7%.

$^1$H NMR (300 MHz, $CDCl_3$) δ 8.34 (1H, br.s), 7.12 (1H, dt, J=1.3, 7.7 Hz), 6.97 (1H, d, J=6.6 Hz), 6.88–6.75 (2H, m), 6.75–6.64 (2H, m), 6.47 (1H, d, J=7.9 Hz), 3.18 (2H, s), 3.10 (1H, dd, J=8.8, 18.7 Hz), 3.00–2.80 (5H, m), 2.75 (3H, s), 2.60–2.48 (1H, m), 2.30 (1H, br.t, J=10.5 Hz), 2.18 (1H, br.t, J=10.6 Hz), 2.05–1.84 (2H, m), 1.70 (2H, d, J=13.4 Hz).

This compound (31.2 mg, 0.0827 mmol) and citric acid (15.9 mg, 0.0827 mmol) was dissolved in methanol (2 ml) and $CH_2Cl_2$ (2 ml), and the solution was stirred at room temperature for 1 h. The solvent was evaporated and the resulting residue was dissolved in methanol (3 drops) and $CH_2Cl_2$ (2 ml). To this solution was added ether and the precipitated solid was collected, washed with ether and dried (50° C. for 3 h) to give 28.7 mg of citrate salt as yellow powder.

MS(ESI positive) m/z: 378.18 (M+1)$^+$.

IR(KBr): 1720, 1668, 1601, 1491, 1435, 1383, 1339, 1277, 1119, 756 cm$^{-1}$

Anal. Calcd for $C_{23}H_{27}N_3O_2$—$C_6H_8O_7$·$4.5H_2O$·$0.3CH_2Cl_2$: C, 56.46; H, 6.65; N, 6.55. Found: C, 56.86; H, 6.48; N, 6.14.

Examples 32 and 33

8-Hydroxy-1-(3-hydroxypropyl)-3-[(1-methyl-1,2-dihydro-1'H-spiro[indole-3,4'-piperidin]-1'-yl)methyl]-3,4-dihydroquinolin-2(1H)-one and 7-[(1-methyl-1,2-dihydro-1'H-spiro[indole-3,4'-piperidin]-1'-yl)methyl]-3,4,7,8-H,6H-[1,4]oxazepino[2,3,4-ij]quinolin-6-one To a stirred solution of 8-methoxy-3-[(1-methyl-1,2-dihydro-1'H-spiro[indole-3,4'-piperidin]-1'-yl)methyl]-quinolin-2(1H)-one (0.20 g, 0.5135 mmol) in DMF (4 ml) was added sodium hydride (60% oil suspension, 24.6 mg, 0.6162 mmol) at 0° C. After 0.5 h stirring, (3-bromopropoxy)-tert-butyldimethylsilane (0.178 ml, 0.7702 mmol) was added to the reaction mixture at 0° C. and the resulting mixture was stirred at 0° C. for 2 h, at room temperature for 20 h, and at 60° C. for 20 h. The reaction mixture was quenched with aqueous solution of $NaHCO_3$ and extracted with $CH_2Cl_2$. The extracts combined were dried ($MgSO_4$), filtered, and concentrated. Resulting crude product was purified by silica gel column chromatography (n-hexane/ethyl acetate: 2/1 then $CH_2Cl_2$/methanol: 20/1) to give 169.7 mg (58.8%) of N-alkyl derivative as yellow syrup.

$^1$H NMR (270 MHz, $CDCl_3$) δ 7.76 (1H, s), 7.23–7.00 (5H, m), 6.71 (1H, t, J=7.3 Hz), 6.48 (1H, d, J=7.4 Hz), 4.70–4.60 (2H, m), 3.94 (3H, s), 3.78 (2H, t, J=6.3 Hz), 3.60 (2H, s), 3.23 (2H, s), 3.00–2.87 (2H, m), 2.28 (2H, br.t, J=9.9 Hz), 2.12–1.95 (2H, m), 1.74 (4H, d, J=13.5 Hz), 0.91 (9H, s), 0.07 (6H, s).

To a stirred solution of the above N-alkyl derivative (169.7 mg, 0.302 mmol) in toluene (4 ml) was added a 1.0 M THF solution of L-selectride (0.906 ml, 0.906 mmol) at −78° C. After 3 h stirring at −78° C. to −30° C., the reaction mixture was quenched with aqueous solution of $NaHCO_3$ and extracted with $CH_2Cl_2$. The extracts combined were dried ($Na_2SO_4$), filtered, and concentrated. Resulting crude product was purified by silica gel column chromatography ($CH_2Cl_2$/methanol: 20/1) to give 201.2 mg of yellow syrup, which was purified again by preparative TLC ($CH_2Cl_2$/methanol: 10/1) to give 106.1 mg (62.3%) of title compound as yellow syrup.

$^1$H NMR (270 MHz, $CDCl_3$) δ 7.15–7.00 (3H, m), 6.90–6.80 (2H, m), 6.70 (1H, t, J=6.6 Hz), 6.47 (1H, d, J=7.8 Hz), 4.20–4.00 (2H, m), 3.86 (3H, s), 3.61 (2H, t, J=6.3 Hz), 3.19 (2H, s), 3.10–2.95 (1H, m), 2.92–2.60 (8H, m, including 3H, s, at 2.76 ppm), 2.55–2.43 (1H, m), 2.29 (1H, t, J=11.0 Hz), 2.15–1.75 (5H, m), 1.69 (2H, d, J=12.5 Hz), 0.87 (9H, s), 0.01 (6H, s).

To a stirred solution of this syrup (106.1 mg, 0.1882 mmol) in $CH_2Cl_2$ (3 ml) was added a 1 M $CH_2Cl_2$ solution of $BBr_3$ (0.94 ml, 0.94 mmol) at 0° C. After 1 d stirring at room temperature, the reaction mixture was quenched with aqueous solution of $NaHCO_3$ and extracted with $CH_2Cl_2$. The extracts combined were dried ($Na_2SO_4$), filtered, and concentrated to give 0.1084 g of brown oil. To a stirred solution of this oil in THF was added 1.0 M THF solution of tetrabutylammonium fluoride (0.565 ml) at 0° C. After 3 h stirring at room temperature, the reaction mixture was quenched with aqueous solution of $NaHCO_3$ and extracted with $CH_2Cl_2$. The crude product was purified by preparative TLC ($CH_2Cl_2$/methanol: 10/1) to give 30.8 mg of 7-membered title compound(Example 33) and 60.1 mg alcohol derivative.

Example 33

$^1$H NMR (270 MHz, $CDCl_3$) δ 7.16–7.03 (2H, m), 6.97–6.81 (3H, m), 6.70 (1H, dt, J=0.8, 12.4 Hz), 6.48 (1H, d, J=7.8 Hz ), 4.43–4.13 (3H, m), 4.00–3.85 (1H, m), 3.20

(2H, s), 3.09 (1H, d, J=10.9 Hz), 2.95–2.68 (8H, m, including 3H, s, at 2.76 ppm), 2.60–2.46 (1H, m), 2.30 (1H, t, J=11.5 Hz), 2.20–1.80 (5H, m), 1.70 (2H, d, J=13.4 Hz).

This compound (25.2 mg, 0.0604 mmol) and citric acid (11.6 mg, 0.0604 mmol) was dissolved in methanol (2 ml) and $CH_2Cl_2$ (2 ml), and the solution was stirred at room temperature for 1 h. The solvent was evaporated and the resulting residue was dissolved in methanol (2 drops) and $CH_2Cl_2$ (2 ml). To this solution was added ether and resulting precipitate was collected by filtration, washed with ether, and dried (50° C.) to give 20.2 mg of citrate salt as white amorphous solid.

MS(ESI positive) m/z: 418.31(M+1)$^+$.

IR(KBr): 3422, 1719, 1655, 1605, 1508, 1474, 1383, 1200, 1119, 961, 793, 754 cm$^{-1}$

A mixture of alcohol derivative (39.4 mg, 0.0905 mmol) and acetic anhydride (0.1 ml) in pyridine (1 ml) was stirred at room temperature for 2 h. After evaporation of the solvent, the residue was dissolved in $CH_2Cl_2$, washed with $NaHCO_3$ solution, dried ($Na_2SO_4$), filtered, and concentrated. The crude product was purified by preparative TLC ($CH_2Cl_2$/methanol: 10/1) to give 24.5 mg of yellow syrup as di-acetate derivative.

To a stirred solution of this di-acetate derivative (24.5 mg, 0.0471 mmol) in methanol (1.5 ml) was added 1.0 M methanol solution of sodium methoxide (9.4 μl, 9.4 μM) at room temperature. After 1 day stirring, 1.0 M methanol solution of sodium methoxide (47 μl, 47 μM) was added to the reaction mixture. After 3 days stirring at room temperature, the reaction mixture was poured into saturated aqueous solution of $NaHCO_3$ and extracted with $CH_2Cl_2$. The extracts combined were dried ($Na_2SO_4$), filtered, and concentrated. The crude product was purified by preparative TLC ($CH_2Cl_2$/methanol: 10/1) to give 17.6 mg of title compound (Example 32) as yellow syrup.

Example 32

$^1$H NMR (270 MHz, CDCl$_3$) δ 7.09 (1H, t, J=7.4 Hz), 6.98 (1H, d, J=7.3 Hz), 6.91 (1H, t, J=7.7 Hz), 6.78 (1H, d, J=7.1 Hz ), 6.75–6.63 (2H, m), 6.47 (1H, d, J=7.9 Hz), 4.19 (2H, t, J=6.3 Hz), 3.68–3.50 (2H, m), 3.17 (2H, s), 3.02 (1H, d, J=14.5 Hz), 2.96–2.60 (8H, m, including 3H, s, at 2.75 ppm), 2.57–2.38 (1H, m), 2.25 (1H, t, J=10.7 Hz), 2.12 (1H, t, J=11.7 Hz), 2.04–1.80 (4H, m), 1.68 (2H, d, J=11.2 Hz).

This compound (17.6 mg, 0.0404 mmol) and citric acid (7.8 mg, 0.0404 mmol) was dissolved in methanol (1 ml) and $CH_2Cl_2$ (1 ml), and the solution was stirred at room temperature for 1 h. The solvent was evaporated and the resulting residue was dried (50° C.) for 3 h to give 22.8 mg of citrate salt as white amorphous solid.

MS(ESI positive) m/z: 436.27(M+1)$^+$.

Example 34

1-Ethyl-8-hydroxy-3-[(1-methyl-1,2-dihydro-1'H-spiro[indole-3,4'-piperidin]-1'-yl)methyl]-3,4-dihydroquinolin-2(1H)-one This was prepared according to the procedure described in Example 32 using iodoethane instead of (3-bromopropoxy)-tert-butyldimethylsilane. The total yield (3 steps) was 9.8%.

$^1$H NMR (270 MHz, CDCl$_3$) δ 7.09 (1H, dt, J=1.2, 7.7 Hz), 7.00 (1H, d, J=6.8 Hz), 6.89 (1H, t, J=7.8 Hz), 6.78 (1H, d, J=7.9 Hz ), 6.75–6.64 (2H, m), 6.47 (1H, d, J=7.8 Hz), 4.10 (2H, q, J=6.9 Hz), 3.18 (2H, s), 3.06–2.84 (4H, m), 2.84–2.60 (5H, m, including 3H, s, at 2.75 ppm), 2.51 (1H, dd, J=7.6, 12.5 Hz), 2.33 (1H, t, J=11.2 Hz), 2.16 (1H, t, J=11.2 Hz), 2.07–1.85 (2H, m), 1.70 (2H, m) 1.16 (3H, t, J=6.9 Hz).

This compound was converted to citrate salt.

MS(ESI positive) m/z: 406.52(M+1)$^+$.

Preparation 21 tert-Butyl 3-(1'H, 3H-spiro[2-benzofuran-1,4'-piperidin]-1'-yl)propanoate

A mixture of 3H-spiro[2-benzofuran-1,4'-piperidine] hydrochloride (2.00 g, 8.86 mmol), tert-butyl acrylate (1.36 g, 10.6 mmol), and triethylamine (1.7 ml, 12.4 mmol) in THF (20 ml) was stirred at 70° C. for 16 h. The reaction mixture was quenched with saturated aqueous $NaHCO_3$ solution and extracted with ethyl acetate (20 ml×3). The extracts combined were washed with brine, dried (MgSO$_4$), filtered, and concentrated. The crude product was purified by silica gel column chromatography ($CH_2Cl_2$/methanol: 20/1) to give 2.77 g (98%) of title compound as colorless oil.

$^1$H NMR (270 MHz, CDCl$_3$) δ 7.30–7.10 (4H, m), 5.07 (2H, s), 2.89–2.72 (4H, m), 2.52–2.40 (4H, m), 2.04–1.90 (2H, m), 1.82–1.72 (2H, m), 1.46 (9H, s).

Example 35

8-Hydroxy-3-(1'H,3H-spiro[2-benzofuran-1,4'-piperidin]-1'-ylmethyl)-3,4-dihydroquinolin-2(1H)-one To a stirred solution of 3-benzyloxy-2-nitrobenzyl alcohol (0.58 g, 2.24 mmol, this was prepared according to the reported method: R. Zamboni et al, Can. J. Chem., 1978, 56, 2725) and carbon tetrabromide (1.11 g, 3.36 mmol) in $CH_2Cl_2$ (15 ml) was added triphenylphosphine (0.70 g, 2.68 mmol) at 0° C. and the resulting reaction mixture was stirred at room temperature for 2 h. Then triphenylphosphine (181 mg, 0.68 mmol) was added to the reaction mixture and stirred for 1 h. The reaction mixture was concentrated and purified by silica gel column chromatography (n-hexane/ethyl acetate:4/1) to afford 670 mg (93%) of bromomethyl derivative as an yellow oil.

$^1$H NMR (270 MHz, CDCl$_3$) δ 7.40–7.30 (6H, m), 7.08 (1H, br.d, J=7.8 Hz), 7.03 (1H, br.d, J=8.8 Hz), 5.19 (2H, s), 4.44 (2H, s).

To a stirred solution of tert-butyl 3-(1'H, 3H-spiro[2-benzofuran-1,4'-piperidin]-1'-yl)propanoate (0.10 g, 0.315 mmol)) in THF (2 ml) was added 1.0 M THF solution of lithium bis(trimethylsilyl)amide (0.41 ml, 0.41 mmol) at −78° C. After 25 min stirring, DMPU (50 μl, 0.41 mmol) was added to the reaction mixture at −78° C. After 25 min stirring, a solution of 3-benzyloxy-2-nitrobenzyl bromide (132 mg, 0.41 mmol) in THF (2 ml) was added to the reaction mixture at −78° C. and the resulting reaction mixture was stirred at −78° C. for 40 min and 0° C. for 20 min. The reaction mixture was quenched with aqueous solution of NH4Cl, extracted with $CH_2Cl_2$. The extracts combined were dried (MgSO$_4$), filtered, concentrated, and purified by silica gel column chromatography (n-hexane/ethyl acetate:5/1) to afford 135 mg (77%) of alkylated product as colorless amorphous solid.

$^1$H NMR (270 MHz, CDCl$_3$) δ 7.40–7.10 (10H, m), 6.95–6.89 (2H, m), 5.15 (2H, s), 5.05 (2H, s), 2.94–2.60 (6H, m), 2.52–2.37 (3H, m), 2.00–1.66 (4H, m), 1.39 (9H, s).

A suspension mixtutre of this alkylated product (135 mg, 0.242 mmol), 10% palladium on carbone (20 mg), and 2N HCl (2 ml) in methanol (6 ml) was stirred under hydrogen atmosphere at room temperature for 6 h. After Celite filtration, the filtrate was concentrated. The residue was basified with aqueous solution of $NaHCO_3$ and extracted with $CH_2Cl_2$. The extracts combined were dried (MgSO$_4$), filtetred, and concentrated. A mixture of this crude product, trifluoroacetic acid (1 ml), and $CH_2Cl_2$ (1 ml) was stirred at room temperature for 2 h. After evaporation of the solvent, the residue was dissolved in THF (6 ml). To this THF solution was added triethylamine (0.17 ml, 1.2 mmol). After 1 h stirring, the reaction mixture was diluted with ethyl acetate, washed with aqueous solution of $NaHCO_3$ and brine, dried ($MgSO_4$), filtered, and concentrated. The crude product was purified by preparative TLC (n-hexane/acetone:1/1 then ethyl acetate/isopropanol:10/1) to afford 57 mg (64%) of title compound as pale brown amorphous solid.

$^1$H NMR (300 MHz, $CDCl_3$) δ 8.40 (1H, br.s), 7.28–7.17 (3H, m), 7.07–7.02 (1H, m), 6.88–6.77 (2H, m), 6.70 (1H, dd, J=1.5, 7.1 Hz), 5.05 (2H, s), 3.17–2.80 (6H, m), 2.65–2.44 (3H, m), 2.12–1.90 (2H, m), 1.81–1.69 (2H, s). This solid (24 mg, 0.064 mmol) and citric acid (13 mg, 0.064 mmol) was dissolved in mixed solvent (1.0 ml of methanol and 1.0 ml of $CH_2Cl_2$), and the solution was stirred at room temperature for 1 h. The solvent was evaporated and resulting residue was solidified from $CH_2Cl_2$/n-hexane and collected by filtration, washed with ether, dried in vacuo (50° C.) to give 30 mg of citrate salt as pale brown amorphous solid.

MS(ESI positive) m/z: 365.03(M+1)$^+$.

IR(KBr): 1720, 1670, 1599, 1491, 1436, 1279, 1217, 766 cm$^{-1}$

Anal. Calcd for $C_{22}H_{24}N_2O_3$—$C_6H_8O_7$·2.2$H_2O$·0.2$CH_2Cl_2$: C, 55.24; H, 6.05; N, 4.57. Found: C, 55.24; H, 5.75; N, 4.17.

Preparation 22
tert-Butyl (2,3-dihydro-1'H-spiro[indene-1,4'-piperidin]-1'-yl)propanoate A mixture of 2,3-dihydrospiro[indene-1,4'-piperidine] hydrochloride (5.00 g, 22.3 mmol), tert-butyl acrylate (3.44 g, 26.8 mmol), and triethylamine (4.4 ml, 31.2 mmol) in THF (50 ml) was stirred at 80° C. for 20 h. tert-Butyl acrylate (1 g, 7.8 mmol), and triethylamine (2 ml, 14.2 mmol) was added to the reaction mixture and stirred at 80° C. for 1 d. The reaction mixture was quenched with saturated aqueous $NaHCO_3$ solution and extracted with ethyl acetate (20 ml×3). The extracts combined were washed with brine, dried ($MgSO_4$), filtered, and concentrated. The crude product was purified by silica gel column chromatography ($CH_2Cl_2$/methanol: 30/1) to give 6.50 g (92%) of title compound as brown oil.

$^1$H NMR (300 MHz, $CDCl_3$) δ 7.23–7.12 (4H, m), 2.92–2.83 (4H, m), 2.75–2.68 (2H, m), 2.50–2.43 (2H, m), 2.27–2.16 (2H, m), 2.03–1.86 (4H, m), 1.62–1.54 (2H, m), 1.46 (9H, s).

Preparation 23
Methyl 3-(2,3-dihydro-1'H-spiro[indene-1,4'-piperidine]-1'-ylmethyl)-2-oxo-1,2,3,4-tetrahydroquinoline-8-carboxylate To a stirred solution of tert-butyl (2,3-dihydro-1'H-spiro [indene-1,4'-piperidin]-1'-yl)propanoate (2.00 g, 6.34 mmol)) in THF (15 ml) was added 1.0 M THF solution of lithium bis(trimethylsilyl)amide (7.6 ml, 7.6 mmol) at −78° C. After 25 min stirring, DMPU (0.92 ml, 7.61 mmol) was added to the reaction mixture at −78° C. After 25 min stirring, a solution of methyl 3-bromomethyl-2-nitrobenzoate (2.09 g, 7.61 mmol, this was prepared according to the reported method: B. C. Soderberg et al, J. Org. Chem., 1997, 62, 5838) in THF (5 ml) was added to the reaction mixture at −78° C. and the resulting reaction mixture was stirred at −78° C. for 40 min and 0° C. for 20 min. The reaction mixture was quenched with aqueous solution of $NH_4Cl$, extracted with $CH_2Cl_2$. The extracts combined were dried ($MgSO_4$), filtered, concentrated, and purified by silica gel column chromatography (n-hexane/ethyl acetate:5/1) to afford 1.85 g (57%) of alkylated product as colorless oil.

$^1$H NMR (270MHz, $CDCl_3$) δ 7.89 (1H, dd, J=1.3, 7.5 Hz), 7.59 (1H, dd, J=1.5, 8.1 Hz), 7.46 (1H, dd, J=7.7, 7.7 Hz), 7.23–7.12 (4H, m), 3.90 (3H, s), 2.92–2.59 (8H, m), 2.48–2.38 (1H, m), 2.25–2.12 (2H, m), 2.02–1.78 (4H, m), 1.39 (9H, s).

A mixture of this alkylated product (2.09 g, 4.11 mmol), trifluoroacetic acid (10 ml), and $CH_2Cl_2$ (5 ml) was stirred at room temperature for 6 h. After evaporation of the solvent, the residue was dissolved in methanol (30 ml). To this solution was added 10% palladium on carbone (200 mg) and stirred under hydrogen atmosphere at room temperature for 5 h. After Celite filtration, the filtrate was concentrated. The residue was basified with aqueous solution of $NaHCO_3$ and extracted with $CH_2Cl_2$. The extracts combined were dried ($MgSO_4$), filtetred, and concentrated. The crude product was purified by silica gel column chromatography ($CH_2Cl_2$/methanol:20/1) to afford 0.80 g (48%) of title compound as colorless amorphous solid.

$^1$H NMR (300 MHz, $CDCl_3$) δ10.44 (1H, br.s), 7.88 (1H, br.d, J=7.1 Hz), 7.41 (1H, br.d, J=7.3 Hz), 7.24–7.12 (4H, m), 7.00 (1H, dd, J=7.5, 7.9 Hz), 3.92 (3H, s), 3.18 (1H, dd, J=5.7, 15.8 Hz), 3.02–2.70 (7H, m), 2.55 (1H, dd, J=9.0, 11.9 Hz), 2.42–2.30 (1H, m), 2.20–2.10 (1H, m), 2.40–1.81 (4H, m), 1.57–1.47 (2H, m).

Example 36
3-(2,3-Dihydro-1'H-spiro[indene-1,4'-piperidine]-1'-ylmethyl)-2-oxo-1,2,3,4-tetrahydroquinoline-8-carboxylic acid A mixture of methyl 3-(2,3-dihydro-1'H-spiro[indene-1,4'-piperidine]-1'-ylmethyl)-2-oxo-1,2,3,4-tetrahydroquinoline-8-carboxylate (70 mg, 0.173 mmol) and 2N NaOH (0.4 ml, 0.8 mmol) in THF (3 ml) and methanol (1.5 ml) was stirred at room temperature for 2 h. The reaction mixture was concentrated and the resulting residue was diluted with water, acidified with 10% citric acid aqueous solution, and extracted with $CH_2Cl_2$. The extracts combined were dried ($MgSO_4$), filtered, and concentrated to give 60 mg (89%) of title compound as colorless amorphous solid.

$^1$H NMR (300 MHz, $CDCl_3$) δ 11.64 (1H, br.s), 7.86 (1H, d, J=7.7 Hz), 7.22–7.08 (5H, m), 6.88 (1H, dd, J=7.5, 7.7 Hz), 3.97–3.70 (2H, m), 3.58 (1H, dd, J=6.8, 12.5 Hz), 3.35–2.80 (8H, m), 2.58–2.25 (2H, m), 2.15–2.00 (2H, m), 1.77–1.65 (2H, m).

MS (ESI positive) m/z: 391.04 (M+H)$^+$.

In the case that d-HCl was used for acidification after 2N NaOH hydrolysis, HCl salt was formed as white solid. Yield was 90.0%.

Example 37
3-(2,3-Dihydro-1'H-spiro[indene-1,4'-piperidine]-1'-ylmethyl)-N,N-dimethyl-2-oxo-1,2,3,4-tetrahydroquinoline-8-carboxamide A mixture of 3-(2,3-dihydro-1'H-spiro[indene-1,4'-piperidine]-1'-ylmethyl)-2-oxo-1,2,3,4-tetrahydroquinoline-8-carboxylic acid hydrochloride (45 mg, 0.105 mmol), dimethylamine hydrochloride (17 mg, 0.21 mmol), WSC (40 mg, 0.21 mmol), HOBt-$H_2O$ (32 mg, 0.21 mmol), and triethylamine (73 μl, 0.53 mmol) in DMF (3 ml) was stirred at room temperature for 1 d. The reaction mixture was quenched with saturated aqueous $NaHCO_3$ solution, and extracted with ethyl acetate. The extracts combined were washed with water and brine, dried ($MgSO_4$), filtered, and concentrated. The residue was purified by preparative TLC (silica gel plate: $CH_2Cl_2$/methanol:10/1) to afford 26 mg (59%) of title compound as colorless oil.

$^1$H NMR (300 MHz, $CDCl_3$) δ 8.58 (1H, br.s), 7.29–7.11 (6H, m), 6.99 (1H, dd, J=7.5, 7.7 Hz), 3.25–2.75 (14H, m), 2.56 (1H, dd, J=8.8, 12.1 Hz), 2.42–2.32 (1H, m), 2.22–2.10 (1H, m), 2.05–1.84 (4H, m), 1.58–1.48 (2H, m).

This oil (26 mg, 0.062 mmol) and citric acid (12 mg, 0.062 mmol) was dissolved in mixed solvent (1.0 ml of methanol and 1.0 ml of $CH_2Cl_2$), and the solution was stirred at room temperature for 1 h. The solvent was evaporated and resulting residue was solidified from $CH_2Cl_2$/n-hexane and collected by filtration, washed with ether, dried in vacuo (50° C.) to give 26 mg of citrate salt as white amorphous solid.

MS(ESI positive) m/z: 418.10 (M+1)$^+$.

Example 38

3-(2,3-Dihydro-1'H-spiro[indene-1,4'-piperidine]-1'-ylmethyl)-N,N-(2-hydroxyethyl)-2-oxo-1,2,3,4-tetrahydroquinoline-8-carboxamide A mixture of 3-(2,3-dihydro-1'H-spiro[indene-1,4'-piperidine]-1'-ylmethyl)-2-oxo-1,2,3,4-tetrahydroquinoline-8-carboxylic acid hydrochloride (45 mg, 0.105 mmol), ethanolamine (13 μl, 0.21 mmol), WSC (40 mg, 0.21 mmol), $HOBt-H_2O$ (32 mg, 0.21 mmol), and triethylamine (73 μl, 0.53 mmol) in DMF (4 ml) was stirred at room temperature for 1 d. Another ethanolamine (13 μl, 0.21 mmol), WSC (40 mg, 0.21 mmol), $HOBt-H_2O$ (32 mg, 0.21 mmol), and triethylamine (73 μl, 0.53 mmol) were added to the reaction mixture and stirred for 5 days. The reaction mixture was quenched with saturated aqueous $NaHCO_3$ solution, and extracted with ethyl acetate. The extracts combined were washed with water and brine, dried ($MgSO_4$), filtered, and concentrated. The residue was purified by preparative TLC (silica gel plate: ethyl acetate/isopropanol:10/1) to afford 9.3 mg (20%) of title compound as colorless amorphous solid.

$^1$H NMR (300 MHz, $CDCl_3$) δ 10.55 (1H, br.s), 7.39 (1H, d, J=7.7 Hz), 7.33 (1H, d, J=7.1 Hz), 7.24–7.12 (4H, m), 6.98 (1H, dd, J=7.5, 7.7 Hz), 6.85–6.75 (1H, m), 3.85 (2H, t, J=5.1 Hz), 3.66–3.58 (2H, m), 3.14 (1H, dd, J=6.0, 15.7 Hz), 2.98–2.652 (8H, m), 2.52 (1H, dd, J=9.0, 12.5 Hz), 2.42–2.30 (1H, m), 2.20–2.10 (1H, m), 2.06–1.82 (4H, m), 1.58–1.48 (2H, m).

This oil (9.3 mg, 0.021 mmol) and citric acid (4.1 mg, 0.021 mmol) was dissolved in mixed solvent (1.0 ml of methanol and 1.0 ml of $CH_2Cl_2$), and the solution was stirred at room temperature for 1 h. The solvent was evaporated and resulting residue was solidified from $CH_2Cl_2$/n-hexane and collected by filtration, washed with ether, dried in vacuo (50° C.) to give 9 mg of citrate salt as white amorphous solid.

MS(ESI positive) m/z: 434.10 (M+1)$^+$.

Example 39

3-(2,3-Dihydro-1'H-spiro[indene-1,4'-piperidine]-1'-ylmethyl)-N,N-dimethyl-2oxo-1,2,3,4-tetrahydroquinoline-8-carboxamide A mixture of 3-(2,3-dihydro-1'H-spiro[indene-1,4'-piperidine]-1'-ylmethyl)-2-oxo-1,2,3,4-tetrahydroquinoline-8-carboxylic acid (70 mg, 0.18 mmol) and 1,1'-carbonyldiimidazole (58 mg, 0.36 mmol) in acetonitrile (4 ml) was refluxed with stirring for 2 h. To this reaction mixture was added 25% ammonium hydroxide (1 ml) and refluxed another 2 h. The reaction mixture was quenched with saturated aqueous $NaHCO_3$ solution, and extracted with $CH_2Cl_2$. The extracts combined were dried ($MgSO_4$), filtered, and concentrated. The residue was purified by preparative TLC (silica gel plate: $CH_2Cl_2$/methanol:10/1) to afford 47 mg (67%) of title compound as white solid.

$^1$H NMR (300 MHz, $CDCl_3$) δ 10.73 (1H, br.s), 7.43–7.36 (2H, m), 7.24–7.14 (4H, m), 7.00 (1H, dd, J=7.5, 7.7 Hz), 6.07 (2H, br.s), 3.19 (1H, dd, J=5.7, 15.9 Hz), 3.02–2.72 (7H, m), 2.63–2.52 (1H, m), 2.43–2.32 (1H, m), 2.23–2.10 (1H, m), 2.05–1.83 (4H, m), 1.58–1.48 (2H, m).

This solid (47 mg, 0.12 mmol) and citric acid (23 mg, 0.12 mmol) was dissolved in mixed solvent (2.0 ml of methanol and 2.0 ml of $CH_2Cl_2$), and the solution was stirred at room temperature for 1 h. The solvent was evaporated and resulting residue was solidified from $CH_2Cl_2$/n-hexane and collected by filtration, washed with ether, dried in vacuo (50° C.) to give 71 mg of citrate salt as white amorphous solid.

MS(ESI positive) m/z: 390.07 (M+1)$^+$.

Anal. Calcd for $C_{24}H_{27}N_3O_2$—$C_6H_8O_7$-$2H_2O$-$0.2CH_2Cl_2$: C, 57.16; H, 6.26; N, 7.22. Found: C, 57.16; H, 5.92; N, 6.43.

Example 40

8-Chloro-3-(2,3-dihydro-1'H-spiro[indene-1,4'-piperidin]-1'-ylmethyl)-3,4-dihydroquinolin-2(1H)-one This was prepared according to the procedure described in preparation 23 using 2-bromomethyl-6-chloronitrobenzene (this was prepared according to the reported method: A. L. Davis et al, *J. Med. Chem.*, 1975, 18, 752) instead of methyl 3-bromomethyl-2-nitrobenzoate, and Fe in acetic acid at 80° C. condition instead of hydrogenation condition using 10% Pd/C. The total yield (3 steps) was 36.8%.

$^1$H NMR (270 MHz, $CDCl_3$) δ 7.80 (1H, br.s), 7.25–7.10 (6H, m), 6.94 (1H, t, J=7.8 Hz), 3.20 (1H, dd, J=5.6, 16.0 Hz), 3.05–2.70 (7H, m, including 2H, t, J=7.4 Hz at 2.89 ppm), 2.65–2.50 (1H, m), 2.58 (1H, br.t, J=10.4 Hz), 2.18 (1H, br.t, J=11.7 Hz), 2.07–1.80 (4H, m,, including 2H, t, J=7.4 Hz at 2.00 ppm), 1.53 (2H, d, J=13.4 Hz.)

This compound was converted to citrate salt (white solid).

MS(ESI positive) m/z: 381.04(M+1)$^+$.

IR(KBr): 3400, 2936, 1686, 1483, 1396, 1188, 762 cm$^{-1}$

Anal. Calcd for $C_{23}H_{25}ClN_2O$—$C_6H_8O_7$-$2.5H_2O$: C, 58.49; H, 6.01; N, 4.70. Found: C, 58.43; H, 6.18; N, 4.36.

Example 41

3-(2,3-Dihydro-1'H-spiro[indene-1,4'-piperidin]-1'-ylmethyl)-7-methoxy-3,4-dihydroquinolin-2(1H)-one This was prepared according to the procedure described in example 40 using 2-bromomethyl-5-methoxynitrobenzene (this was prepared according to the reported method: J. L. Neumeyer et al, *J. Med. Chem.*, 1976, 19, 25) instead of 2-bromomethyl-6-chloronitrobenzene. The total yield (3 steps) was 16.1%.

$^1$H NMR (270 MHz, $CDCl_3$) δ 8.50–8.30 (1H, m), 7.25–7.08 (5H, m), 6.54 (1H, dd, J=2.5, 8.2 Hz), 6.36 (1H, m), 3.78 (3H, s), 3.18–3.03 (1H, m), 3.00–2.74 (7H, m), 2.62–2.50 (1H, m), 2.36 (1H, br.t, J=10.2 Hz), 2.18 (1H, br.t, J=10.6 Hz), 2.07–1.83 (4H, m,, including 2H, t, J=7.3 Hz at 2.00 ppm), 1.52 (2H, d, J=13.8 Hz).

This compound was converted to citrate salt (white solid).

MS(ESI positive) m/z: 377.09(M+1)$^+$.

IR(KBr): 3425, 2939, 1717, 1680, 1626, 1597, 1520, 1394, 1267, 1198, 1163, 1034, 760 cm$^{-1}$

Anal. Calcd for $C_{24}H_{28}N_2O_2$—$C_6H_8O_7$-$3H_2O$: C, 60.49; H, 6.60; N, 4.70. Found: C, 60.22; H, 6.62; N, 4.40.

Example 42

3-(2,3-Dihydro-1'H-spiro[indene-1,4'-piperidin]-1'-ylmethyl)-7-hydroxy-3,4-dihydroquinolin-2(1H)-one This was prepared according to the procedure described in example 26. The yield was 90.9%.

$^1$H NMR (270 MHz, CDCl$_3$ and DMSO-d6(2 drops)) δ 8.81 (1H, br.s), 7.31–7.10 (4H, m), 6.99 (1H, d, J=8.1 Hz), 6.47 (1H, dd, J=2.3, 8.1 Hz), 6.39 (1H, d, J=1.5 Hz), 3.15–2.65 (8H, m), 2.65–2.48 (1H, m), 2.36 (1H, br.t, J=11.5 Hz), 2.17 (1H, br.t, J=12.5 Hz), 2.10–1.85 (4H, m, including 2H, t, J=7.3 Hz at 2.00 ppm), 1.52 (2H, d, J=13.4 Hz).

This compound was converted to citrate salt (white solid).
MS(ESI positive) m/z: 363.08(M+1)$^+$.
IR(KBr): 3410, 2936, 1670, 1605, 1524, 1398, 1296, 1227, 1178, 831, 762 cm$^{-1}$ Anal. Calcd for C$_{23}$H$_{26}$N$_2$O$_2$—C$_6$H$_8$O$_7$-3H$_2$O: C, 59.89; H, 6.41; N, 4.82. Found: C, 59.96; H, 6.37; N, 4.89.

Example 43

3-(2,3-Dihydro-1'H-spiro[indene-1,4'-piperidin]-1'-ylmethyl)-7-fluoro-3,4-dihydroquinolin-2(1H)-one This was prepared according to the procedure described in example 41 using 2-bromomethyl-5-fluoronitrobenzene (this was prepared according to the reported method: T. J. McCord et al, *J. Heterocycl. Chem.*, 1982, 19, 401) instead of 2-bromomethyl-5-methoxynitrobenzene. In this case, reduction condition (Fe in acetic acid at 80° C.) gave not the desired compound but N-hydroxyl derivative in 95.6% yield. This N-hydroxyl derivative was converted to the title compound using TiCl$_3$ in THF according to the reported procedure (*Bull. Chem. Soc. Jpn.*, 1994, 67, 2542). The total yield (4 steps) was 25.9%.

$^1$H NMR (270 MHz, CDCl$_3$) δ 8.91 (1H, br.s), 7.25–7.10 (5H, m), 6.69 (1H, dt, J=2.5, 8.4 Hz), 6.58 (1H, br.d, J=9.4 Hz), 3.12 (1H, dd, J=4.5, 14.7 Hz), 2.96–2.73 (7H, m), 2.61–2.48 (1H, m), 2.36 (1H, br.t, J=12.7 Hz), 2.17 (1H, br.t, J=10.25 Hz), 2.06–1.82 (4H, m, including 2H, t, J=7.3 Hz at 2.00 ppm), 1.53 (2H, d, J=13.0 Hz).

This compound was converted to citrate salt (white solid).
MS(ESI positive) m/z: 365.09(M+1)$^+$.
IR(KBr): 3400, 2949, 2858, 1690, 1611, 1516, 1479, 1387, 1259, 1150, 822, 758 cm$^{-1}$ Anal. Calcd for C$_{23}$H$_{25}$FN$_2$O—C$_6$H$_8$O$_7$-3H$_2$O: C, 59.68; H, 6.22; N, 4.80. Found: C, 59.67; H, 6.25; N, 4.57.

Example 44

5-Chloro-3-(2,3-Dihydro-1'H-spiro[indene-1,4'-piperidin]-1'-ylmethyl)-3,4-dihydroquinolin-2(1H)-one This was prepared according to the procedure described in example 41 using 2-bromomethyl-3-chloronitrobenzene (this was prepared according to the reported method: A. L. Davis et al, *J. Med. Chem.*, 1975, 18, 752) instead of 2-bromomethyl-5-methoxynitrobenzene. The total yield (3 steps) was 9.6%.

$^1$H NMR (300 MHz, CDCl$_3$) δ 8.81–8.64 (1H, m), 7.25–7.03 (6H, m), 6.72 (1H, dd, J=1.5, 7.3 Hz), 3.27 (3H, 1H, dd, J=6.1, 16.7 Hz), 3.09 (1H, dd, J=8.3, 16.7 Hz), 2.95–2.75 (6H, m), 2.61–2.50 (1H, m), 2.36 (1H, br.t, J=9.92 Hz), 2.21 (1H, t, J=10.3 Hz), 2.05–1.83 (4H, m,, including 2H, t, J=7.3 Hz at 2.00 ppm), 1.51 (2H, d, J=13.2 Hz).

This compound was converted to citrate salt (white solid).
MS(ESI positive) m/z: 381.00(M+1)$^+$.
IR(KBr): 3418, 2937, 1717, 1682, 1585, 1474, 1390, 1203, 777, 760 cm$^{-1}$ Anal. Calcd for C$_{23}$H$_{25}$ClN$_2$O—C$_6$H$_8$O$_7$-5H$_2$O: C, 56.35; H, 6.20; N, 4.53. Found: C, 56.59; H, 5.93; N, 4.20.

Example 45

3-(2,3-Dihydro-1'H-spiro[indene-1,4'-piperidin]-1'-ylmethyl)-5-methoxy-3,4-dihydroquinolin-2(1H)-one This was prepared according to the procedure described in example 41 using 2-bromomethyl-3-methoxynitrobenzene (this was prepared according to the reported method: J. L. Neumeyer et al, *J. Med. Chem.*, 1976, 19, 190) instead of 2-bromomethyl-5-methoxynitrobenzene. The total yield (3 steps) was 54.6%.

$^1$H NMR (300 MHz, CDCl$_3$) δ 8.36–8.15 (1H, m), 7.25–7.08 (5H, m), 6.59 (1H, d, J=7.9 Hz), 6.43 (1H, 1H, d, J=7.9 Hz), 3.86 (3H, s), 3.30–3.14 (1H, m), 2.96–2.72 (7H, m), 2.63–2.53 (1H, m), 2.35 (1H, t, J=11.2 Hz), 2.21 (1H, t, J=11.0 Hz), 2.06–1.85 (4H, m, , including 2H, t, J=7.5 Hz at 2.00 ppm), 1.51 (2H, d, J=13.4 Hz).

This compound was converted to citrate salt (white solid).
MS(ESI positive) m/z: 377.06(M+1)$^+$.
IR(KBr): 2939, 1724, 1676, 1601, 1481, 1429, 1394, 1332, 1269, 1204, 1196, 1109, 952, 777, 762 cm$^{-1}$ Anal. Calcd for C$_{243}$H$_{28}$N$_2$O$_2$—C$_6$H$_8$O$_7$-4.5H$_2$O: C, 59.15; H, 6.70; N, 4.60. Found: C, 59.18; H, 6.46; N, 4.15.

Example 46

3-(2,3-Dihydro-1'H-spiro[indene-1,4'-piperidin]-1'-ylmethyl)-5-hydroxy-3,4-dihydroquinolin-2(1H)-one This was prepared according to the procedure described in example 26. The yield was 87.5%.

$^1$H NMR (300 MHz, CDCl$_3$) δ 8.66–8.40 (1H, m), 7.23–7.08 (4H, m), 6.99 (1H, t, J=8.3 Hz), 6.58 (1H, d, J=8.1 Hz), 6.35 (1H, d, J=7.7 Hz), 4.05–3.30 (2H, m), 3.30–3.13 (1H, m), 3.05–2.75 (6H, m), 2.70–2.58 (1H, m), 2.38 (1H, t, J=11.9 Hz), 2.25 (1H, t, J=11.7 Hz), 2.10–1.90 (4H, m), 1.60–1.45 (2H, m).

This compound was converted to citrate salt (white amorphous solid).
MS(ESI positive) m/z: 363.08(M+1)$^+$.
IR(KBr): 3200, 2939, 1717, 1670, 1605, 1524, 1485, 1393, 1332, 1229, 1055, 781, 760 cm$^{-1}$ Anal. Calcd for C$_{23}$H$_{26}$N$_2$O$_2$—C$_6$H$_8$O$_7$-4.5H$_2$O: C, 58.53; H, 6.52; N, 4.71. Found: C, 58.59; H, 6.26; N, 4.26.

Example 47

3-(2,3-Dihydro-1'H-spiro[indene-1,4'-piperidin]-1'-ylmethyl)-5-fluoro-3,4-dihydroquinolin-2(1H)-one This was prepared according to the procedure described in example 43 using 2-bromomethyl-4-fluoronitrobenzene (this was prepared according to the reported method: T. J. McCord et al, *J. Heterocycl. Chem.*, 1982, 19, 401) instead of 2-bromomethyl-5-fluoronitrobenzene. In this case, reduction condition (hydrogenation using 10% Pd/C in methanol instead of Fe in acetic acid at 80° C.) gave the mixture of desired compound and N-hydroxyl derivative. This mixture was converted to the title compound using TiCl$_3$ in THF according to the reported procedure (*Bull. Chem. Soc. Jpn.*, 1994, 67, 2542). The total yield (4 steps) was 13.9%.

$^1$H NMR (300 MHz, CDCl$_3$) δ 8.90–8.50 (1H, m), 7.30–7.12 (4H, m), 6.95 (1H, dd, J=2.6, 8.6 Hz), 6.88 (1H, dt, J=2.6, 8.4 Hz), 6.81–6.73 (1H, m), 3.14 (1H, dd, J=5.7, 15.8 Hz), 3.00–2.74 (7H, m, including 2H, t, J=7.3 Hz at 2.89 ppm), 2.62–2.48 (1H, m), 2.37 (1H, br.t, J=11.0 Hz), 2.17 (1H, br.t, J=11.6 Hz), 2.07–1.83 (4H, m, including 2H, t, J=7.3 Hz at 2.00 ppm), 1.53 (2H, d, J=13.4 Hz).

This compound was converted to citrate salt (white solid).
MS(ESI positive) m/z: 365.20(M+1)$^+$.
IR(KBr): 2939, 1722, 1684, 1585, 1506, 1385, 1236, 1147, 1110, 968, 760 cm$^{-1}$ Anal. Calcd for C$_{23}$H$_{25}$FN$_2$O—C$_6$H$_8$O$_7$-2.5H$_2$O: C, 60.15; H, 6.18; N, 4.84. Found: C, 60.02; H, 6.28; N, 4.46.

Example 48

3-(2,3-Dihydro-1'H-spiro[indene-1,4'-piperidin]-1'-ylmethyl)-8-(hydroxymethyl)-3,4-dihydroquinolin-2(1H)-one To a stirred suspension of 3-(2,3-dihydro-1'H-spiro[indene-1,4'-piperidine]-1'-ylmethyl)-2-oxo-1,2,3,4-tetrahydroquinoline-8-carboxylic acid (220 mg, 0.563 mmol, this was prepared as example 36) in CH$_2$Cl$_2$ (9 ml) was added oxalyl chloride (0.20 ml, 2.25 mmol) at room temperature and the resulting mixture was refluxed for 5 h. The reaction mixture was concentrated to give yellow solid. To a stirred suspension of this solid in CH$_2$Cl$_2$ (12 ml) was added dropwise a solution of tetrabutylammonium borohydride (159 mg, 0.619 mmol) in CH$_2$Cl$_2$ (2 ml) at −78° C. After 1 h stirring at −78° C., the reaction mixture was quenched with saturated aqueous NaHCO$_3$ solution (40 ml) and extracted with CH$_2$Cl$_2$. The extracts combined were dried (MgSO$_4$), filtered, and concentrated. The resulting crude product was purified by silica gel column chromatography (n-hexane/ethyl acetate: 1/2) to give 110 mg (52%) of title compound as pale yellow amorphous solid.

$^1$H NMR (270 MHz, CDCl$_3$) δ 9.40 (1H, br.s), 7.25–7.04 (5H, m), 7.06 (1H, br.d, J=7.5 Hz), 6.94 (1H, dd, J=7.4, 7.6 Hz), 4.78 (1H, d, J=12.5 Hz), 4.72 (1H, d, J=12.7 Hz), 3.88 (1H, br.s), 3.15–3.05 (1H, m), 2.92–2.72 (7H, m), 2.48 (1H, dd, J=7.4, 12.0 Hz), 2.37–2.25 (1H, m), 2.22–2.10 (1H, m), 2.05–1.85 (4H, m), 1.56–1.46 (2H, m).

This compound was converted to citrate salt (pale yellow solid).

MS(ESI positive) m/z: 377.04(M+1)$^+$.

Example 49

3-(2,3-Dihydro-1'H-spiro[indene-1,4'-piperidin]-1'-ylmethyl)-8-[(dimethylamino)methyl]-3,4-dihydroquinolin-2(1H)-one To a stirred solution of 3-(2,3-dihydro-1'H-spiro[indene-1,4'-piperidin]-1'-ylmethyl)-8-(hydroxymethyl)-3,4-dihydroquinolin-2(1H)-one (106 mg, 0.282 mmol, this was prepared in example 48) in CH2Cl2 (4 ml) was added triethylamine (0.059 ml, 0.423 mmol) and methanesulfonyl chloride (0.028 ml, 0.366 mmol) at 0° C. and the resulting reaction mixture was stirred at 0° C. for 2.5 hn. The reaction mixture was quenched with saturated aqueous NaHCO$_3$ solution and extracted with CH$_2$Cl$_2$. The extracts combined were dried (MgSO$_4$), filtered, and concentrated to give 0.11 g of crude chloride derivative. A mixture of this chloride (35 mg, 0.089 mmol), dimethylamine hydrochloride (91.44 mg, 1.12 mmol) and triethylamine (0.248 ml, 1.78 mmol) in THF (6 ml) was refluxed for 2 days. The reaction mixture was quenched with saturated aqueous NaHCO$_3$ solution and extracted with ethyl acetate. The extracts combined were washed with brine, dried (MgSO$_4$), filtered, and concentrated. The residue was purified by preparative TLC (silica gel plate, ethyl acetate/isopropanol: 10/1) to give 11.3 mg (31%) of title compound.

$^1$H NMR (270 MHz, CDCl$_3$) δ 10.25 (1H, br.s), 7.25–7.11 (5H, m), 6.98–6.86 (2H, m), 3.57 (1H, d, J=13.2 Hz), 3.40 (1H, d, J=13.2 Hz), 3.16 (1H, dd, J=5.4, 15.5 Hz), 2.97–2.74 (7H, m), 2.62–2.52 (1H, m), 2.44–2.33 (1H, m), 2.22 (6H, s), 2.22–2.12 (1H, m), 2.01 (2H, t, J=7.2 Hz), 1.98–1.85 (3H, m), 1.60–1.48 (2H, m).

This compound was converted to citrate salt (brown solid).

MS(ESI positive) m/z: 404.13(M+1)$^+$.

Example 50

8-(Aminomethyl)-3-(2,3-dihydro-1'H-spiro[indene-1,4'-piperidin]-1'-ylmethyl)-3,4-dihydroquinolin-2(1H)-one To a stirred solution of 3-(2,3-dihydro-1'H-spiro[indene-1,4'-piperidin]-1'-ylmethyl)-8-(hydroxymethyl)-3,4-dihydroquinolin-2(1H)-one (106 mg, 0.282 mmol, this was prepared in example 48) in CH$_2$Cl$_2$ (4 ml) was added triethylamine (0.059 ml, 0.423 mmol) and methanesulfonyl chloride (0.028 ml, 0.366 mmol) at 0° C. and the resulting reaction mixture was stirred at 0° C. for 2.5 h. The reaction mixture was quenched with saturated aqueous NaHCO$_3$ solution and extracted with CH$_2$Cl$_2$. The extracts combined were dried (MgSO$_4$), filtered, and concentrated to give 0.11 g of crude chloride derivative. A mixture of this chloride (75 mg, 0.19 mmol), sodium azide (32 mg, 0.49 mmol) and in DMF (2 ml) was stirred at 80° C. for 16 h. Then sodium azide (74.1 mg, 1.14 mmol) was added to the reaction mixture. The reaction mixture was quenched with saturated aqueous NaHCO$_3$ solution and extracted with ethyl acetate. The extracts combined were washed with water and brine, dried (MgSO$_4$), filtered, and concentrated. The residue was purified by preparative TLC (silica gel plate, CH$_2$Cl$_2$/methanol: 10/1) to give 50 mg (66%) of azide derivative. A mixture of this azide derivative (50 mg, 0.125 mmol) and 10% palladium on carbon (12 mg) in methanol (4 ml) was stirred under hydrogen atmosphere at room temperature for 5 h. After usual workup, this reaction condition was repeated with prolonged reaction time (1 day). Then catalyst was changed to palladium black (15 mg) and hydrogenated for 4 h. After removal of catalyst by filtration, the filtrate was concentrated. The residue was purified by preparative TLC (silica gel plate, ethyl acetate/isopropanol: 10/1) to give 15.4 mg (33%) of title compound as an yellow oil.

$^1$H NMR (270 MHz, CDCl$_3$) δ 7.25–7.11 (5H, m), 7.00 (1H, br.d, J=7.1 Hz), 6.90 (1H, dd, J=7.4, 7.4 Hz), 4.00 (2H, s), 3.16 (1H, dd, J=5.1, 15.0 Hz), 2.96–2.74 (7H, m), 2.56 (1H, dd, J=8.9, 12.4 Hz), 2.43–2.32 (1H, m), 2.25–2.12 (1H, m), 2.02–1.85 (5H, m, including 2H, t, J=7.4 Hz at 2.00 ppm), 1.58–1.47 (2H, m).

This compound was converted to citrate salt (brown solid).

MS(ESI positive) m/z: 376.10(M+1)$^+$.

Example 51

3-(2,3-Dihydro-1'H-spiro[indene-1,4'-piperidin]-1'-ylmethyl)-2-oxo-1,2,3,4-tetrahydroquinoline-8-carbonitrile To a stirred solution of 3-(2,3-dihydro-1'H-spiro[indene-1,4'-piperidine]-1'-ylmethyl)-N,N-dimethyl-2-oxo-1,2,3,4-tetrahydroquinoline-8-carboxamide (150 mg, 0.385 mmol, this was prepared in example 39) in DMF (4 ml) was added thionyl chloride (0.0565 ml, 0.771 mmol) at room temperature and the resulting reaction mixture was stirred for 7 h. The reaction mixture was quenched with saturated aqueous NaHCO$_3$ solution and extracted with CH$_2$Cl$_2$. The extracts combined were washed with water, dried (MgSO$_4$), filtered, and concentrated. The residue was purified by silica gel column chromatography (CH$_2$Cl$_2$/methanol: 50/1) to give 129 mg (90%) of title compound as colorless amorphous solid.

$^1$H NMR (270 MHz, CDCl$_3$) δ 7.88 (1H, br.s), 7.46 (2H, d, J=7.7 Hz), 7.25–7.13 (4H, m), 7.07 (1H, dd, J=7.6, 7.7 Hz), 3.21 (1H, dd, J=5.8, 16.0 Hz), 3.05–2.70 (7H, m), 2.56 (1H, dd, J=10.4, 13.7 Hz), 2.43–2.32 (1H, m), 2.23–2.12 (1H, m), 2.04–1.80 (5H, m, including 2H, t, J=7.4 Hz at 2.00 ppm), 1.58–1.48 (2H, m).

This compound was converted to citrate salt (white solid).

MS(ESI positive) m/z: 372.06(M+1)$^+$.

IR(KBr): 3400, 2928, 2228, 1693, 1595, 1491, 1472, 1398, 1280, 760 cm$^{-1}$

Anal. Calcd for $C_{24}H_{25}N_3O—C_6H_8O_7-2.5H_2O$: C, 59.20; H, 6.29; N, 6.90. Found: C, 59.41; H, 5.89; N, 6.51.

Example 52

6-(2,3-Dihydro-1'H-spiro[indene-1,4'-piperidin]-1'-ylmethyl)-1,2,6,7-tetrahydro-3H,5H-pyrido[3,2,1-ij]quinazolin-3-one To a stirred solution of 3-(2,3-dihydro-1'H-spiro[indene-1,4'-piperidin]-1'-ylmethyl)-2-oxo-1,2,3,4-tetrahydroquinoline-8-carbonitrile (95 mg, 0.26 mmol, this was prepared in example 51) in THF (3 ml) was added lithium aluminium hydride (19 mg, 0.51 mmol) at room temperature and the resulting reaction mixture was stirred for 30 min. Then lithium aluminium hydride (9.9 mg, 0.26 mmol) was added to the reaction mixture and heated at 80° C. for 3 h. Then lithium aluminium hydride (19 mg, 0.51 mmol) was added to the reaction mixture and heated at 90° C. for 2 h. Then lithium aluminium hydride (49 mg, 1.3 mmol) was added to the reaction mixture and heated at 90° C. for 1 h. The reaction mixture was cooled down, quenched with water (90 μl), 2N NaOH (90 μl), and water (270 μl). After 30 min stirring, the resulting solid formed was removed by filtration. The filtrate concentrated to give 90 mg of crude amine derivative as yellow oil. To a stirred solution of this oil (90 mg, 0.26 mmol) and triethylamine (0.181 ml, 1.3 mmol) in THF (3 ml) was added diphosgene (57 mg, 0.29 mmol) at room temperature. After 1.5 h stirring, the reaction mixture was quenched with aqueous $NaHCO_3$ solution and extracted with $CH_2Cl_2$. The extracts combined were dried ($MgSO_4$), filtered, and concentrated. The residue was purified by preparative TLC (silica gel plate: hexane/ethyl acetatel:1/2, 2 developed) to afford 16 mg (16%) of title compound as white solid.

$^1$H NMR (270 MHz, $CDCl_3$) δ 7.26–7.11 (4H, m), 7.08–7.02 (1H, m), 6.94–6.85/(2H, m), 5.16 (1H, br.s), 4.50–4.36 (2H, m), 4.34–4.26 (1H, m), 3.18 (1H, dd, J=9.7, 12.9 Hz), 2.96–2.80 (5H, m), 2.58–1.90 (10H, m, including 2H, t, J=7.4 Hz at 2.00 ppm), 1.608–1.47 (2H, m).

This was converted to citric acid salt (pale yellow solid).

MS (ESI positive) m/z: 388.04 (M+H)$^+$.

IR(KBr): 3296, 2934, 1719, 1655, 1601, 1448, 1229, 760 cm$^{-1}$

What is claimed is:

1. A compound of the following formula I

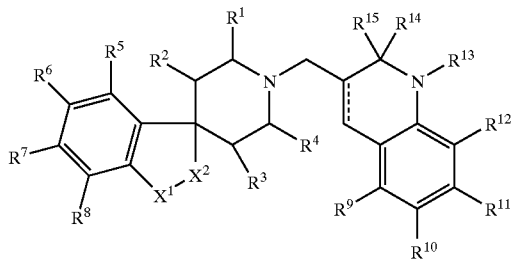

I or a pharmaceutically acceptable salt or solvate thereof, wherein $R^1$ through $R^{12}$ are independently selected from the group consisting of hydrogen; halo; hydroxy; cyano; $(C_1-C_6)$alkyl; $(C_1-C_6)$alkyl substituted with one to five halo which may be same or different; $(C_1-C_6)$alkyl substituted with one to five substituents independently selected from the group consisting of hydroxy, amino, $[(C_1-C_6)$alkyl]NH—, $[(C_1-C_6)$alkyl]$_2$N—, $H_2$NC(=O)—, $[(C_1-C_6)$alkyl]NHC(=O)—, $[(C_1-C_6)$alkyl]$_2$NC(=O)—, $(C-C_6)$alkoxy and a fully saturated five to six membered heterocyclyl containing one to two hetero atoms independently selected from nitrogen and oxygen; $(C_1-C_6)$alkoxy; $(C_1-C_6)$alkoxy substituted with one to five halo which may be same or different; $(C_1-C_6)$alkoxy substituted with one to five substituents independently selected from the group consisting of hydroxy, amino, $[(C_1-C_6)$alkyl]NH—, $[(C_1-C_6)$alkyl]$_2$N—, $H_2$NC(=O)—, $[(C_1-C_6)$alkyl] NHC(=O)— and , $[(C_1-C_6)$alkyl]$_2$NC(=O)—; amino; $[(C_1-C_6)$alkyl]NH—; $[(C_1-C_6)$alkyl]$_2$N—; carboxy; $[(C_1-C_6)$alkoxy]C(=O)—; $H_2$NC(=O)—; $[(C_1-C_6)$alkyl]NHC(=O)—; $[(C_1-C_6)$alkyl]NHC(=O)— wherein said $(C_1-C_6)$alkyl is substituted with one hydroxy; $[(C_1-C_6)$alkyl]$_2$NC(=O)—; $[(C_1-C_6)$alkyl]$_2$NC(=O)— wherein either or both of $(C_1-C_6)$ alkyl is substituted with one hydroxy; and aryl selected from phenyl and naphthyl;

$X^1$ and $X^2$ are each $CH_2$; or $X^1$ and $X^2$ taken together form CH=CH;

$R^{13}$ is selected from the group consisting of hydrogen; hydroxy; $(C_1-C_6)$alkyl; $(C_1-C_6)$alkyl substituted with one to five halo which may be same or different; and $(C_1-C_6)$alkyl substituted with one to five substituents independently selected from the group consisting of hydroxy, amino, $[(C_1-C_6)$alkyl]NH—, $[(C_1-C_6)$alkyl]$_2$N—, $H_2$NC(=O)—, $[(C_1-C_6)$alkyl]NHC(=O)—, $[(C_1-C_6)$alkyl]$_2$NC(=O)—, $(C_1-C_6)$alkoxy and a fully saturated five to six membered heterocyclyl containing one to two hetero atoms independently selected from nitrogen and oxygen; or $R^{12}$ and $R^{13}$ taken together with the three ring atoms of the dihydro- or tetrahydro-quinoline ring separating said substituents form a five to seven membered ring which is partially or fully unsaturated, wherein one or two of the carbon atoms not shared with the dihydro- or tetrahydro-quinoline ring are optionally substituted with substituents independently selected from oxo; hydroxy; $(C_1-C_6)$alkyl; $(C_1-C_6)$alkyl substituted with one to five halo which maybe same or different; $(C_1-C_6)$alkyl substituted with one to five substituents independently selected from the group consisting of hydroxy, amino, $[(C_1-C_6)$alkyl]NH—, $[(C_1-C_6)$alkyl]$_2$N—, $H_2$NC(=O)—, $[(C_1-C_6)$alkyl]NHC(=O)—, $[(C_1-C_6)$alkyl]$_2$NC(=O)—, $(C_1-C_6)$ alkoxy and a fully saturated five to six membered heterocyclyl containing one to two hetero atoms independently selected from nitrogen and oxygen; $(C_1-C_6)$alkoxy; $(C_1-C_6)$alkoxy substituted with one to five halo which may be same or different; $(C_1-C_6)$ alkoxy substituted with one to five substituents independently selected from the group consisting of hydroxy, amino, $[(C_1-C_6)$alkyl]NH—, $[(C_1-C_6)$ alkyl]$_2$N—, $H_2$NC(=O)—, $[(C_1-C_6)$alkyl]NHC(=O)— and $[(C_1-C_6)$alkyl]$_2$NC(=O)—; amino; $[(C_1-C_6)$alkyl]NH—; and $[(C_1-C_6)$alkyl]$_2$N—;

both $R^{14}$ and $R^{15}$ are hydrogen or taken together form oxo; and the dotted line represents a single or double bond.

2. A compound according to claim 1 wherein both $R^{14}$ and $R^{15}$ are hydrogen.

3. A compound according to claim 1 wherein $R^{14}$ and $R^{15}$ taken together form oxo.

4. A compound according to any one of claims 1 to 3 wherein $R^1$, $R^2$, $R^3$ and $R^4$ are all hydrogen.

5. A compound according to any one of claims 1 to 3 wherein $R^5$, $R^6$, $R^7$ and $R^8$ are all hydrogen.

6. A compound according to any one of claims 1 to 3 wherein $R^9$, $R^{10}$ and $R^{11}$ are independently selected from the group consisting of hydrogen; halo; hydroxy; cyano; $(C_1-C_6)$alkyl; $(C_1-C_6)$alkyl substituted with one to five halo which may be same or different; $(C_1-C_6)$alkyl substituted with one to five substituents independently selected from the group consisting of hydroxy, amino, $[(C_1-C_6)$alkyl]NH—, $[(C_1-C_6)$alkyl]$_2$N—, $H_2$NC(=O)—, $[(C_1-C_6)$alkyl]NHC(=O)—, $[(C_1-C_6)$alkyl]$_2$NC(=O)—, $(C_1-C_6)$alkoxy and a fully saturated five to six membered heterocyclyl containing one to two hetero atoms independently selected from nitrogen and oxygen; $H_2$NC(=O)—; $[(C_1-C_6)$alkyl]NHC(=O)— and $[(C_1-C_6)$alkyl]$_2$NC(=O)—.

7. A compound according to any one of claims 1 to 3 wherein $R^{12}$ is selected from the group consisting of hydrogen; halo; hydroxy; cyano; $(C_1-C_6)$alkyl; $(C_1-C_6)$alkyl substituted with one to five halo which may be same or different; $(C_1-C_6)$alkyl substituted with one to five substituents independently selected from the group consisting of hydroxy, amino, $[(C_1-C_6)$alkyl]NH—, $[(C_1-C_6)$alkyl]$_2$N—, $H_2$NC(=O)—, $[(C_1-C_6)$alkyl]NHC(=O)—, $[C_1-C_6)$alkyl]$_2$NC(=O)—, $C_1-C_6)$alkoxy and a fully saturated five to six membered heterocyclyl containing one to two hetero atoms independently selected from nitrogen and oxygen; $H_2$NC(=O)—; $[(C_1-C_6)$alkyl]NHC(=O)— and $[(C_1-C_6)$alkyl]$_2$NC(=O)—.

8. A compound according to any one of claims 1 to 3 wherein $R^{13}$ is selected from a group consisting of hydrogen; hydroxy; $(C_1-C_6)$alkyl; $(C_1-C_6)$alkyl substituted with one to five halo which may be same or different; and $(C_1-C_6)$alkyl substituted with one to five substituents independently selected from the group consisting of hydroxy, amino, $[(C_1-C_6)$alkyl]NH—, $[(C_1-C_6)$alkyl]$_2$N—, $H_2$NC(=O)—, $[(C_1-C_6)$alkyl]NHC(=O)—, $[(C_1-C_6)$alkyl]$_2$NC(=O)—, $(C_1-C_6)$alkoxy and a fully saturated five to six membered heterocyclyl containing one to two hetero atoms independently selected from nitrogen and oxygen.

9. A compound according to claim 1 selected from 2,3-dihydro-1'-[(2-oxo-1,2,3,4-tetrahydro-3-quinolinyl) methyl]spiro[1H-indene-1,4'-piperidine];

3-(2,3-dihydro-1'H-spiro[indene-1,4'piperidin]-1'-ylmethyl)-8-methoxy-3,4-dihydroquinolin-2(1H)-one;

3-(2,3-dihydro-1'H-spiro[indene-1,4'-piperidin]-1'-ylmethyl)-8-(hydroxymethyl)-3,4-dihydroquinolin-2(1H)-one;

8-chloro-3-(2,3-dihydro-1'H-spiro[indene-1,4'-piperidin]-1'-ylmethyl)-3,4-dihydroquinolin-2(1H)-one;

5-chloro-3-(2,3-Dihydro-1'H-spiro[indene-1,4'-piperidin]-1'-ylmethyl)-3,4-dihydroquinolin-2(1H)-one; and 8-(aminomethyl)-3-(2,3-dihydro-1'H-spiro[indene-1,4'-piperidin]-1'-ylmethyl)-3,4-dihydroquinolin-2(111)-one;

and pharmaceutically acceptable salts and solvates thereof.

10. A compound according to claim 1 selected from 6-(2,3-dihydro-1'H-spiro[indene-1,4'-piperidin]-1'-ylmethyl)-1,2,6,7-tetrahydro-3H,5H-pyrido[3,2,1-ij]quinazolin-3-one;

and pharmaceutically acceptable salts and solvates thereof.

11. A pharmaceutical compositon comprising an effective amount of a compound of claim 1 and a pharmaceutically acceptable carrier.

* * * * *